United States Patent
Singh et al.

(10) Patent No.: US 8,012,955 B2
(45) Date of Patent: Sep. 6, 2011

(54) N-SUBSTITUTED-HETEROCYCLO-ALKYLOXYBENZAMIDE COMPOUNDS AND METHODS OF USE

(75) Inventors: Rajinder Singh, Belmont, CA (US); Jiaxin Yu, San Carlos, CA (US); Hui Hong, Palo Alto, CA (US); Sambaiah Thota, Fremont, CA (US); Xiang Xu, South San Francisco, CA (US); Ihab S. Darwish, San Carlos, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 410 days.

(21) Appl. No.: 11/963,742

(22) Filed: Dec. 21, 2007

(65) Prior Publication Data

US 2009/0186894 A1    Jul. 23, 2009

Related U.S. Application Data

(60) Provisional application No. 60/882,312, filed on Dec. 28, 2006, provisional application No. 60/988,719, filed on Nov. 16, 2007.

(51) Int. Cl.
| | |
|---|---|
| A01N 43/00 | (2006.01) |
| A01N 43/40 | (2006.01) |
| A01N 43/36 | (2006.01) |
| A61K 31/5365 | (2006.01) |
| A61K 31/5383 | (2006.01) |
| A61K 31/55 | (2006.01) |
| A61K 31/445 | (2006.01) |
| A61K 31/40 | (2006.01) |
| C07D 223/00 | (2006.01) |
| C07D 211/40 | (2006.01) |
| C07D 211/54 | (2006.01) |
| C07D 211/00 | (2006.01) |
| C07D 207/00 | (2006.01) |
| C07D 207/06 | (2006.01) |
| C07D 295/02 | (2006.01) |
| C07D 205/00 | (2006.01) |

(52) U.S. Cl. .............. 514/210.07; 514/212.01; 514/327; 514/424; 540/484; 546/216; 546/217; 548/541; 548/579; 548/952; 548/953

(58) Field of Classification Search .............. 514/210.19, 514/217.03, 326, 327, 422, 424, 210.07, 514/212.01; 540/604, 484; 546/192, 216, 546/217; 548/416, 517, 952, 541, 579, 953
See application file for complete search history.

(56) References Cited

U.S. PATENT DOCUMENTS

| | | | |
|---|---|---|---|
| 5,332,732 A | 7/1994 | Scott et al. | |
| 5,438,064 A | 8/1995 | Mobilio et al. | |
| 5,665,719 A | 9/1997 | Bock et al. | |
| 5,958,945 A | 9/1999 | Imbert et al. | |
| 5,965,591 A | 10/1999 | Kojima et al. | |
| 6,096,771 A | 8/2000 | Kojima et al. | |
| 6,472,394 B1 | 10/2002 | McKittrick et al. | |
| 6,492,355 B1 | 12/2002 | Alcaraz et al. | |
| 6,821,965 B1 | 11/2004 | Brown et al. | |
| 7,001,900 B2 | 2/2006 | Jacobsen et al. | |
| 7,208,491 B2 | 4/2007 | Fertig et al. | |
| 7,273,868 B2 | 9/2007 | Yamada et al. | |
| 2003/0216582 A1 | 11/2003 | Nikolaides et al. | |
| 2004/0082542 A1 | 4/2004 | Mjalli et al. | |
| 2005/0038081 A1 | 2/2005 | Brown et al. | |
| 2005/0107399 A1 | 5/2005 | Boman et al. | |
| 2005/0131018 A1 | 6/2005 | Sendzik | |
| 2005/0182040 A1 | 8/2005 | Imazaki et al. | |
| 2005/0187261 A1 | 8/2005 | Verner et al. | |
| 2005/0234057 A1 | 10/2005 | Wook et al. | |
| 2005/0282864 A1 | 12/2005 | McArthur et al. | |
| 2006/0009449 A1 | 1/2006 | McArthur et al. | |
| 2006/0084679 A1 | 4/2006 | McArthur et al. | |
| 2006/0167053 A1 | 7/2006 | Lino et al. | |
| 2006/0205772 A1 | 9/2006 | Coppola et al. | |
| 2006/0270653 A1 | 11/2006 | Drutu et al. | |

(Continued)

FOREIGN PATENT DOCUMENTS

EP    0158380 A1    10/1985

(Continued)

OTHER PUBLICATIONS

Fan et. al., Bioorganic & Medicinal Chemistry Letters, 1997, Elsevier Science, vol. 7, No. 24, pp. 3107-3112.*

(Continued)

*Primary Examiner* — Shengjun Wang
*Assistant Examiner* — Sarah Pihonak
(74) *Attorney, Agent, or Firm* — Travis Young; McDonnell Boehnen Hulbert & Berghoff LLP

(57) ABSTRACT

The present invention provides N-substituted-heterocycloalkyloxybenzamide compounds, as well as pharmaceutical compositions and methods of use. One embodiment of the invention is a compound having the structure

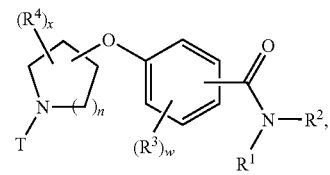

in which $R^1$, $R^2$, $R^3$, $R^4$, T, n, w and x are as described herein. In certain embodiments of the invention, a compound of the present invention activates the AMPK pathway, and can be used to treat metabolism-related disorders and conditions.

70 Claims, 5 Drawing Sheets

U.S. PATENT DOCUMENTS

| | | |
|---|---|---|
| 2007/0021386 A1 | 1/2007 | Mjalli et al. |
| 2007/0123515 A1 | 5/2007 | Nettekoven et al. |
| 2007/0123525 A1 | 5/2007 | Nettekoven et al. |
| 2007/0123526 A1 | 5/2007 | Nettekoven et al. |

FOREIGN PATENT DOCUMENTS

| | | |
|---|---|---|
| EP | 0254322 A1 | 1/1988 |
| WO | WO 96/06837 A1 | 3/1996 |
| WO | WO 99/59959 A1 | 11/1999 |
| WO | 00/12074 | 3/2000 |
| WO | WO0012074 | 3/2000 |
| WO | WO 01/64639 A2 | 9/2001 |
| WO | WO 02/34718 A1 | 5/2002 |
| WO | 03/015774 A1 | 2/2003 |
| WO | 03/018586 | 3/2003 |
| WO | WO 03/022856 A1 | 3/2003 |
| WO | WO03018586 | 3/2003 |
| WO | WO03022856 | 3/2003 |
| WO | WO 03/028641 A2 | 4/2003 |
| WO | WO03070732 | 8/2003 |
| WO | WO 03/072578 A1 | 9/2003 |
| WO | WO 03/097047 A1 | 11/2003 |
| WO | WO 2004/005295 A1 | 1/2004 |
| WO | WO 2004/022060 A2 | 3/2004 |
| WO | WO2004054974 | 7/2004 |
| WO | WO 2004/065351 A1 | 8/2004 |
| WO | WO 2004/099204 A1 | 11/2004 |
| WO | 2004/111003 | 12/2004 |
| WO | WO2004111003 | 12/2004 |
| WO | WO 2005/014533 A2 | 2/2005 |
| WO | WO 2005/023761 A2 | 3/2005 |
| WO | 2005/061442 | 7/2005 |
| WO | WO2005061442 | 7/2005 |
| WO | WO2005116000 | 12/2005 |
| WO | WO 2006/009054 A1 | 1/2006 |
| WO | WO 2006/020879 A1 | 2/2006 |
| WO | WO 2006/056848 A1 | 6/2006 |
| WO | WO 2006/066924 A2 | 6/2006 |
| WO | WO 2006/067139 A1 | 6/2006 |
| WO | WO 2006/091862 A2 | 8/2006 |
| WO | 2006/108965 | 10/2006 |
| WO | WO 2006/108965 A2 | 10/2006 |
| WO | WO 2007/003962 A2 | 1/2007 |
| WO | WO 2007/057329 A1 | 5/2007 |
| WO | WO 2007/065948 A1 | 6/2007 |
| WO | WO 2007/073935 A1 | 7/2007 |
| WO | WO2007075688 | 7/2007 |
| WO | 2007/098086 | 8/2007 |
| WO | WO2007098086 | 8/2007 |
| WO | 2007/143823 | 12/2007 |
| WO | 2007/143824 | 12/2007 |
| WO | 2007/149929 | 12/2007 |
| WO | WO 2007/149929 A1 | 12/2007 |
| WO | WO2007143823 | 12/2007 |
| WO | WO2007143824 | 12/2007 |
| WO | WO2008017685 | 2/2008 |
| WO | WO2008133975 | 11/2008 |

OTHER PUBLICATIONS

Kitamura et. al., Chem. Pharm. Bull., 2001, Pharmaceutical Society of Japan, vol. 49, issue 3, pp. 268-277.*

West, Solid State Chemistry and its Applications, 1987, John Wiley & Sons, pp. 358 & 365.*

Database Registry [Online] Chemical Abstract Service, Columbus, Ohio, USA; Dec. 20, 2007, XP002474728; retrieved from STN; CAS RF: 958939-37-2.

Database Registry [Online] Chemical Abstract Service, Columbus, Ohio, USA; Dec. 19, 2007, XP002474730; retrieved from STN; CAS RF: 958847-90-0.

Tudose et al., "Synthesis and Properties of dinitrobenzamido-TEMPO derivatives", ARKIVOC vi (2005). 225-237.

Bell et al., "Development of Orally Active Oxytocin Antagonists: Studies on 1-(1-{4-[1-(2-Methyl-1-oxidopyridin-3-ylmethyl)piperidin-4-yloxy]-2-methoxybenzoyl}piperidin-4-yl)-1,4-dihydrobenz[d] [1,3] oxazin-2-one (L-372,662) and Related Pyridines", Journal of Medicinal Chemistry (1998). 2146-2163, vol. 41, No. 12.

Copending U.S. Appl. No. 12/272,581, filed Nov. 17, 2008.

Copending U.S. Appl. No. 12/334,201, filed Dec. 12, 2008.

Copending U.S. Appl. No. 12/428,334, filed Apr. 22, 2009.

International Search Report and Written Opinion for PCT/US2007/088742, (Apr. 12, 2008).

* cited by examiner

N-SUBSTITUTED-HETEROCYCLO-ALKYLOXYBENZAMIDE COMPOUNDS AND METHODS OF USE

CROSS REFERENCE TO RELATED APPLICATIONS

This application claims priority under 35 U.S.C. §119(e) to U.S. Provisional Patent Applications Ser. Nos. 60/882,312, filed Dec. 28, 2006, and 60/988,719, filed Nov. 16, 2007, each of which is hereby incorporated herein by reference.

BACKGROUND OF THE INVENTION

1. Field of the Invention

The invention relates generally to compounds, pharmaceutical compositions and methods of use of the compounds and compositions containing them. The invention relates more particularly to N-substituted-heterocycloalkyloxybenzamide compounds and pharmaceutical compositions thereof, and to methods of treating and preventing disease states such as type II diabetes, atherosclerosis and cardiovascular disease using N-substituted-heterocycloalkyloxybenzamide compounds.

2. Technical Background

Adiponectin is a protein hormone exclusively expressed in and secreted from adipose tissue and is the most abundant adipose-specific protein. Adiponectin has been implicated in the modulation of glucose and lipid metabolism in insulin-sensitive tissues. Decreased circulating adiponectin levels have been demonstrated in some insulin-resistant states, such as obesity and type 2 diabetes mellitus and also in patients with coronary artery disease, atherosclerosis and hypertension. Adiponectin levels are positively correlated with insulin sensitivity, HDL (high density lipoprotein) levels and insulin stimulated glucose disposal and inversely correlated with adiposity and glucose, insulin and triglyceride levels. Thiazolidinedione drugs, which enhance insulin sensitivity through activation of the peroxisome proliferator-activated receptors, increase endogenous adiponectin production in humans.

Adiponectin binds its receptors in liver and skeletal muscle and thereby activates the 5'-AMP-activated protein kinase (AMPK) pathway. Adiponectin receptors 1 and 2 are membrane-bound proteins found in skeletal muscle and liver tissue. Being a multi-substrate enzyme, AMPK regulates a variety of metabolic processes, such as glucose transport, glycolysis and lipid metabolism. It acts as a sensor of cellular energy homeostasis and is activated in response to certain hormones and muscle contraction as well as to intracellular metabolic stress signals such as exercise, ischemia, hypoxia and nutrient deprivation. Once activated, AMPK switches on catabolic pathways (such as fatty acid oxidation and glycolysis) and switches off ATP-consuming pathways (such as lipogenesis). Adiponectin improves insulin sensitivity by directly stimulating glucose uptake in adipocytes and muscle and by increasing fatty acid oxidation in liver and muscle, resulting in reduced circulating fatty acid levels and reduced intracellular triglyceride contents. Moreover, adiponectin decreases glycogen concentration by reducing the activity of glycogen synthase. Adiponectin also plays a protective role against inflammation and atherosclerosis. It suppresses the expression of adhesion molecules in vascular endothelial cells and cytokine production from macrophages, thus inhibiting the inflammatory processes that occur during the early phases of atherosclerosis. What is needed are compounds, pharmaceutical compositions and methods of using them to treat disease states associated with circulating adiponectin levels, such as type II diabetes, atherosclerosis and cardiovascular disease.

SUMMARY OF THE INVENTION

A first aspect of the invention is a compound having structural formula (I)

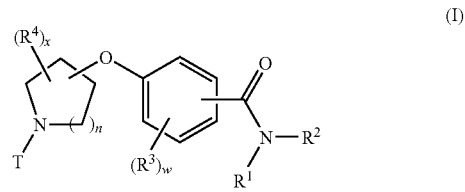

or a pharmaceutically acceptable salt, solvate, hydrate, or N-oxide thereof, wherein
  $R^1$ is H;
  $R^2$ is -Hca;
  each $R^3$ is independently selected from —($C_1$-$C_6$ alkyl), —($C_1$-$C_6$ fluoroalkyl), —($C_0$-$C_6$ alkyl)-Ar; —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-S(O)$_{0-2}R^{10}$, -halogen, —$NO_2$ and —CN;
  w is 0, 1, 2, or 3;
  n is 0, 1 2 or 3;
  each $R^4$ is independently selected from —($C_1$-$C_6$ alkyl), —($C_1$-$C_6$ fluoroalkyl), —($C_0$-$C_6$ alkyl)-Ar; —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-S(O)$_{0-2}R^{10}$, -halogen, —$NO_2$ and —CN, and two $R^4$ on the same carbon optionally combine to form oxo;
  x is 0, 1, 2, 3 or 4;
  T is —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-S(O)$_{0-2}R^{10}$; or

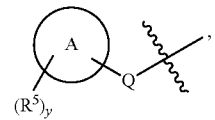

in which
  Q is —($C_0$-$C_3$ alkyl)-, in which each carbon of the —($C_0$-$C_3$ alkyl)- is optionally and independently substituted with one or two $R^{16}$;
  each $R^{16}$ is independently selected from —($C_1$-$C_6$ alkyl), —($C_1$-$C_6$ fluoroalkyl), —($C_0$-$C_6$ alkyl)-Ar; —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-S(O)$_{0-2}R^{10}$, -halogen, —$NO_2$ and —CN, and two $R^{16}$ on the same carbon optionally combine to form oxo;
  the ring system denoted by "A" is heteroaryl, aryl, cycloalkyl or heterocycloalkyl;
  each $R^5$ is independently selected from —($C_1$-$C_6$ alkyl), —($C_1$-$C_6$ fluoroalkyl), —($C_0$-$C_6$ alkyl)-Ar; —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —(C₀-C₆ alkyl)-OR¹⁰, —(C₀-C₆ alkyl)-S(O)₀₋₂R¹⁰, -halogen, —NO₂ and —CN; and y is 0, 1, 2, 3 or 4;

in which each L is independently selected from —NR⁹C(O)O—, —NR⁹C(O)—NR⁹—, —NR⁹C(O)S—, —NR⁹C(O)—, —NR⁹C(S)O—, —NR⁹C(S)—NR⁹—, —NR⁹C(S)S—, —NR⁹C(S)—, —OC(O)NR⁹—, —SC(O)NR⁹—, —C(S)NR⁹—, —OC(S)NR⁹—, —SC(S)NR⁹—, —C(S)NR⁹—, —S(O)₀₋₂—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR⁹C(NR²)NR⁹—, —NR⁹SO₂—, —SO₂NR⁹— and —NR⁹SO₂NR⁹—, each R⁶, R⁷, R⁸ and R¹⁰ is independently selected from H, —(C₁-C₆ alkyl), —(C₁-C₆ fluoroalkyl), —(C₀-C₆ alkyl)-Ar, —(C₀-C₆ alkyl)-Het, —(C₀-C₆ alkyl)-Cak, —(C₀-C₆ alkyl)-Hca, —(C₀-C₆ alkyl)-L-(C₀-C₆ alkyl), —(C₀-C₆ alkyl)-NR⁹(C₀-C₆ alkyl), —(C₀-C₆ alkyl)-O—(C₀-C₆ alkyl) and —(C₀-C₆ alkyl)-S(O)₀₋₂—(C₀-C₆ alkyl), each R⁹ is independently selected from —H, —(C₁-C₄ alkyl) and —C(O)—(C₁-C₄ alkyl), each Ar is an optionally substituted aryl, each Het is an optionally substituted heteroaryl, each Cak is an optionally substituted cycloalkyl, each Hca is an optionally substituted heterocycloalkyl, and each alkyl is optionally substituted, provided that the compound is not N-(1-benzylpiperidin-4-yl)-3-chloro-4-(1-(4-methoxybenzyl)piperidin-4-yloxy)benzamide;

N-(1-benzylpiperidin-4-yl)-4-(1-benzylpiperidin-4-yloxy)-3-methoxybenzamide;

N-(1-benzylpiperidin-4-yl)-4-(1-(furan-2-ylmethyl)piperidin-4-yloxy)benzamide;

N-(1-benzylpiperidin-4-yl)-4-(1-((1-methyl-1H-imidazol-5-yl)methyl)piperidin-4-yloxy)benzamide;

N-(1-benzylpiperidin-4-yl)-3-chloro-4-(1-((1-methyl-1H-imidazol-5-yl)methyl)piperidin-4-yloxy)benzamide;

N-(1-benzylpiperidin-4-yl)-3-chloro-4-(1-(pyridin-4-ylmethyl)piperidin-4-yloxy)benzamide;

N-(1-benzylpiperidin-4-yl)-3-methoxy-4-(1-(3-phenylpropyl)piperidin-4-yloxy)benzamide;

N-(1-benzylpiperidin-4-yl)-3-methoxy-4-(1-(thiophen-2-yl)piperidin-4-yloxy)benzamide;

N-(1-benzylpiperidin-4-yl)-3-methoxy-4-(1-(methylsulfonyl)piperidin-4-yloxy)benzamide;

N-(1-benzylpiperidin-4-yl)-3-chloro-4-(1-(thiophen-2-yl)piperidin-4-yloxy)benzamide;

N-(1-benzylpiperidin-4-yl)-3-chloro-4-(1-(furan-2-yl)piperidin-4-yloxy)benzamide;

N-(1-benzylpiperidin-4-yl)-3-methoxy-4-(1-(furan-2-yl)piperidin-4-yloxy)benzamide; or N-(1-benzylpiperidin-4-yl)-3-(1-benzylpiperidin-4-yloxy)benzamide.

Another aspect of the invention is a pharmaceutical composition comprising at least one pharmaceutically acceptable carrier, diluent or excipient; and a compound having structural formula (I)

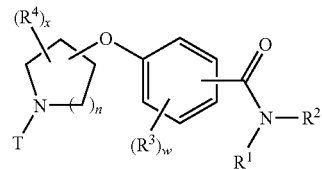

or a pharmaceutically acceptable salt, solvate, hydrate, or N-oxide thereof, wherein R¹ is H;

R² is -Hca;

each R³ is independently selected from —(C₁-C₆ alkyl), —(C₁-C₆ fluoroalkyl), —(C₀-C₆ alkyl)-Ar; —(C₀-C₆ alkyl)-Het, —(C₀-C₆ alkyl)-Cak, —(C₀-C₆ alkyl)-Hca, —(C₀-C₆ alkyl)-L-R⁷, —(C₀-C₆ alkyl)-NR⁸R⁹, —(C₀-C₆ alkyl)-OR¹⁰, —(C₀-C₆ alkyl)-S(O)₀₋₂R¹⁰, -halogen, —NO₂ and —CN;

w is 0, 1, 2 or 3;

n is 0, 1, 2 or 3;

each R⁴ is independently selected from —(C₁-C₆ alkyl), —(C₁-C₆ fluoroalkyl), —(C₀-C₆ alkyl)-Ar; —(C₀-C₆ alkyl)-Het, —(C₀-C₆ alkyl)-Cak, —(C₀-C₆ alkyl)-Hca, —(C₀-C₆ alkyl)-L-R⁷, —(C₀-C₆ alkyl)-NR⁸R⁹, —(C₀-C₆ alkyl)-OR¹⁰, —(C₀-C₆ alkyl)-S(O)₀₋₂R¹⁰, -halogen, —NO₂ and —CN, and two R⁴ on the same carbon optionally combine to form oxo;

x is 0, 1, 2, 3 or 4;

T is —(C₀-C₆ alkyl)-L-R⁷, —(C₀-C₆ alkyl)-NR⁸R⁹, —(C₀-C₆ alkyl)-OR¹⁰, —(C₀-C₆ alkyl)-S(O)₀₋₂R¹⁰; or

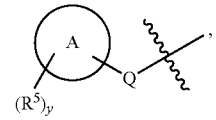

in which

Q is —(C₀-C₃ alkyl)-, in which each carbon of the (C₀-C₃ alkyl) is optionally and independently substituted with one or two R¹⁶;

each R¹⁶ is independently selected from —(C₁-C₆ alkyl), —(C₁-C₆ fluoroalkyl), —(C₀-C₆ alkyl)-Ar; —(C₀-C₆ alkyl)-Het, —(C₀-C₆ alkyl)-Cak, —(C₀-C₆ alkyl)-Hca, —(C₀-C₆ alkyl)-L-R⁷, —(C₀-C₆ alkyl)-NR⁸R⁹, —(C₀-C₆ alkyl)-OR¹⁰, —(C₀-C₆ alkyl)-S(O)₀₋₂R¹⁰, -halogen, —NO₂ and —CN, and two R¹⁶ on the same carbon optionally combine to form oxo;

the ring system denoted by "A" is heteroaryl, aryl, cycloalkyl or heterocycloalkyl;

each R⁵ is independently selected from —(C₁-C₆ alkyl), —(C₁-C₆ fluoroalkyl), —(C₀-C₆ alkyl)-Ar; —(C₀-C₆ alkyl)-Het, —(C₀-C₆ alkyl)-Cak, —(C₀-C₆ alkyl)-Hca, —(C₀-C₆ alkyl)-L-R⁷, —(C₀-C₆ alkyl)-NR⁸R⁹, —(C₀-C₆ alkyl)-OR¹⁰, —(C₀-C₆ alkyl)-S(O)₀₋₂R¹⁰, -halogen, —NO₂ and —CN; and y is 0, 1, 2, 3 or 4;

in which each L is independently selected from —NR⁹C(O)O—, —NR⁹C(O)—NR⁹—, —NR⁹C(O)S—, —NR⁹C(O)—, —NR⁹C(S)O—, —NR⁹C(S)—NR⁹—, —NR⁹C(S)S—, —NR⁹C(S)—, —OC(O)NR⁹—, —SC(O)NR⁹—, —C(S)NR⁹—, —OC(S)NR⁹—, —SC(S)NR⁹—, —C(S)NR⁹—, —S(O)₀₋₂—, —C(O)O, —OC(O)—, —C(S)O—, —OC(S)—,
—C(O)S—, —SC(O)—, —C(S)S—, —SC(S)—,
—OC(O)O—, —SC(O)O—, —OC(O)S—, —SC(S)
O—, —OC(S)S—, —NR$^9$C(NR$^2$)NR$^9$—,
—NR$^9$SO$_2$—, —SO$_2$NR$^9$— and —NR$^9$SO$_2$NR$^9$—,
each R$^6$, R$^7$, R$^8$ and R$^{10}$ is independently selected from H, —(C$_1$-C$_6$ alkyl), —(C$_1$-C$_6$ fluoroalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl) and —(C$_0$-C$_6$ alkyl)-S(O)$_{0-2}$—(C$_0$-C$_6$ alkyl),
each R$^9$ is independently selected from —H, —(C$_1$-C$_4$ alkyl) and —C(O)—(C$_1$-C$_4$ alkyl),
each Ar is an optionally substituted aryl,
each Het is an optionally substituted heteroaryl,
each Cak is an optionally substituted cycloalkyl,
each Hca is an optionally substituted heterocycloalkyl, and
each alkyl is optionally substituted.

Another aspect of the invention is a method for activating the AMPK pathway in a cell, the method comprising contacting the cell with an effective amount of a compound, pharmaceutically acceptable salt, prodrug, solvate, hydrate or N-oxide or composition described above.

Another aspect of the invention is a method for increasing fatty acid oxidation in a cell, the method comprising contacting the cell with an effective amount of a compound, pharmaceutically acceptable salt, prodrug, solvate, hydrate or N-oxide or composition described above.

Another aspect of the invention is a method for decreasing glycogen concentration in a cell, the method comprising contacting the cell with an effective amount of a compound, pharmaceutically acceptable salt, prodrug, solvate, hydrate or N-oxide or composition described above.

Another aspect of the invention is a method for reducing triglyceride levels in a subject, the method comprising administering to the subject an effective amount of a compound, pharmaceutically acceptable salt, prodrug, solvate, hydrate or N-oxide or composition described above.

Another aspect of the invention is a method for treating type II diabetes in a subject, the method comprising administering to the subject an effective amount of a compound, pharmaceutically acceptable salt, prodrug, solvate, hydrate or N-oxide or composition described above.

Another aspect of the invention is a method for treating or preventing atherosclerosis or cardiovascular disease in a subject, the method comprising administering to the subject an effective amount of a compound, pharmaceutically acceptable salt, prodrug, solvate, hydrate or N-oxide or composition described above.

DETAILED DESCRIPTION OF THE INVENTION

Figure 1:
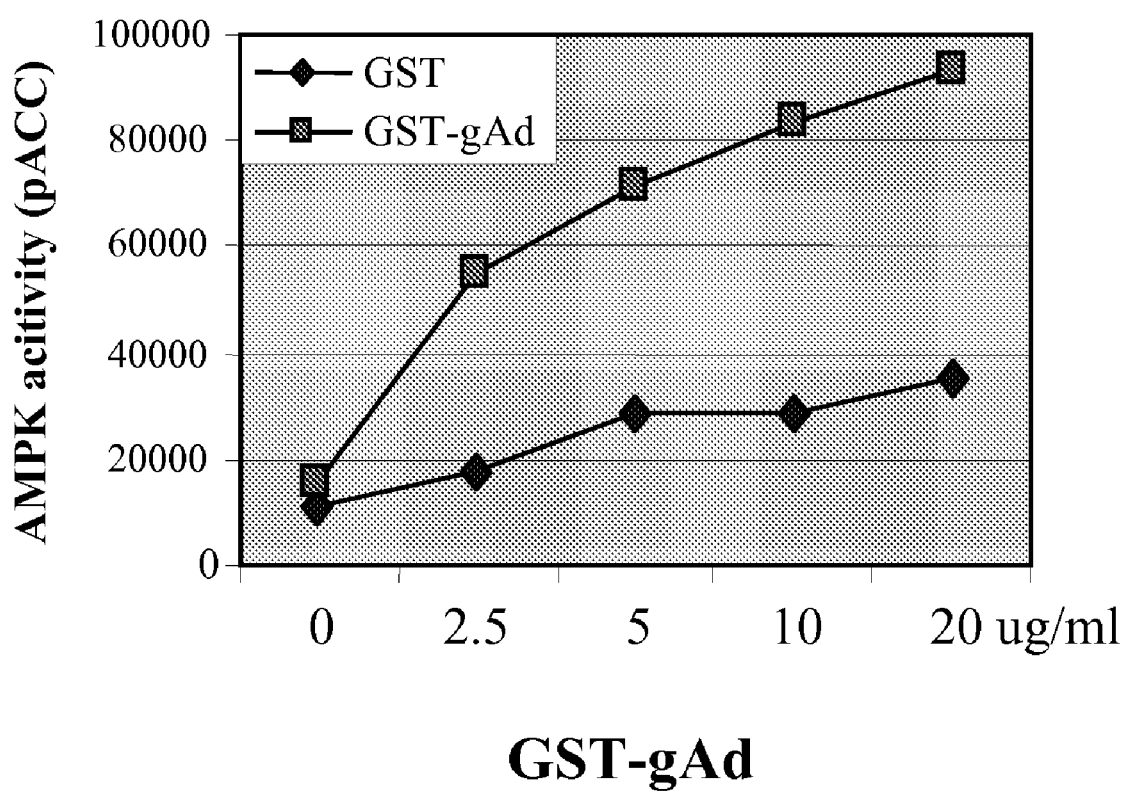
FIG. 1 is a plot of AMPK activity vs. concentration for both glutathione S-transferase and its fusion protein with globular adiponectin (gAd)

A first aspect of the invention provides compounds having structural formula (I):

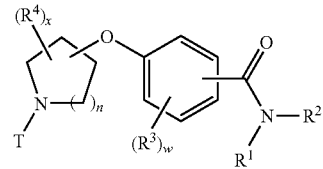

(I)

and pharmaceutically acceptable salts, solvates, hydrates, and N-oxides thereof, in which R$^1$ is H;
R$^2$ is -Hca;
each R$^3$ is independently selected from —(C$_1$-C$_6$ alkyl), —(C$_1$-C$_6$ fluoroalkyl), —(C$_0$-C$_6$ alkyl)-Ar; —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$, -halogen, —NO$_2$ and —CN;
w is 0, 1, 2, or 3;
n is 0, 1 2 or 3;
each R$^4$ is independently selected from —(C$_1$-C$_6$ alkyl), —(C$_1$-C$_6$ fluoroalkyl), —(C$_0$-C$_6$ alkyl)-Ar; —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$, -halogen, —NO$_2$ and —CN, and two R$^4$ on the same carbon optionally combine to form oxo;
x is 0, 1, 2, 3 or 4;
T is —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$; or

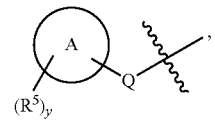

in which
Q is —(C$_0$-C$_3$ alkyl)-, in which each carbon of the —(C$_0$-C$_3$ alkyl)- is optionally and independently substituted with one or two R$^{16}$;
each R$^{16}$ is independently selected from —(C$_1$-C$_6$ alkyl), —(C$_1$-C$_6$ fluoroalkyl), —(C$_0$-C$_6$ alkyl)-Ar; —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$, -halogen, —NO$_2$ and —CN, and two R$^{16}$ on the same carbon optionally combine to form oxo;
the ring system denoted by "A" is heteroaryl, aryl, cycloalkyl or heterocycloalkyl;
each R$^5$ is independently selected from —(C$_1$-C$_6$ alkyl), —(C$_1$-C$_6$ fluoroalkyl), —(C$_0$-C$_6$ alkyl)-Ar; —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$, -halogen, —NO$_2$ and —CN; and
y is 0, 1, 2, 3 or 4;
in which
each L is independently selected from —NR$^9$C(O)O—, —NR$^9$C(O)—NR$^9$—, —NR$^9$C(O)S—, —NR$^9$C (O)—, —NR$^9$C(S)O—, —NR$^9$C(S)—NR$^9$—, —NR$^9$C(S)S—, —NR$^9$C(S)—, —OC(O)NR$^9$—, —SC(O)NR$^9$—, —C(S)NR$^9$—, —OC(S)NR$^9$—, —SC(S)NR$^9$—, —C(S)NR$^9$—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR$^9$C(NR$^2$)NR$^9$—, —NR$^9$SO$_2$—, —SO$_2$NR$^9$— and —NR$^9$SO$_2$NR$^9$—, each R$^6$, R$^7$, R$^8$ and R$^{10}$ is independently selected from H, —(C$_1$-C$_6$ alkyl), —(C$_1$-C$_6$ fluoroalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl) and —(C$_0$-C$_6$ alkyl)-S(O)$_{0-2}$—(C$_0$-C$_6$ alkyl), each R$^9$ is independently selected from —H, —(C$_1$-C$_4$ alkyl) and —C(O)—(C$_1$-C$_4$ alkyl), each Ar is an optionally substituted aryl, each Het is an optionally substituted heteroaryl, each Cak is an optionally substituted cycloalkyl, each Hca is an optionally substituted heterocycloalkyl, and each alkyl is optionally substituted, provided that the compound is not N-(1-benzylpiperidin-4-yl)-3-chloro-4-(1-(4-methoxybenzyl)piperidin-4-yloxy)benzamide;

N-(1-benzylpiperidin-4-yl)-4-(1-benzylpiperidin-4-yloxy)-3-methoxybenzamide;

N-(1-benzylpiperidin-4-yl)-4-(1-(furan-2-ylmethyl)piperidin-4-yloxy)benzamide;

N-(1-benzylpiperidin-4-yl)-4-(1-((1-methyl-1H-imidazol-5-yl)methyl)piperidin-4-yloxy)benzamide;

N-(1-benzylpiperidin-4-yl)-3-chloro-4-(1-((1-methyl-1H-imidazol-5-yl)methyl)piperidin-4-yloxy)benzamide;

N-(1-benzylpiperidin-4-yl)-3-chloro-4-(1-(pyridin-4-ylmethyl)piperidin-4-yloxy)benzamide;

N-(1-benzylpiperidin-4-yl)-3-methoxy-4-(1-(3-phenylpropyl)piperidin-4-yloxy)benzamide;

N-(1-benzylpiperidin-4-yl)-3-methoxy-4-(1-(thiophen-2-yl)piperidin-4-yloxy)benzamide;

N-(1-benzylpiperidin-4-yl)-3-methoxy-4-(1-(methylsulfonyl)piperidin-4-yloxy)benzamide;

N-(1-benzylpiperidin-4-yl)-3-chloro-4-(1-(thiophen-2-yl)piperidin-4-yloxy)benzamide;

N-(1-benzylpiperidin-4-yl)-3-chloro-4-(1-(furan-2-yl)piperidin-4-yloxy)benzamide;

N-(1-benzylpiperidin-4-yl)-3-methoxy-4-(1-(furan-2-yl)piperidin-4-yloxy)benzamide; or N-(1-benzylpiperidin-4-yl)-3-(1-benzylpiperidin-4-yloxy)benzamide.

In one embodiment according to the first aspect of the invention, the compound is a compound as described above with reference to structural formula (I), but is not 3-fluoro-N-(1-phenylpiperidin-4-yl)-4-(1-(4-(trifluoromethyl)phenyl)piperidin-4-yloxy)benzamide; or -(1-(4-cyanobenzyl)piperidin-4-yloxy)-N-(piperidin-4-yl)benzamide.

In one embodiment according to the first aspect of the invention, two R$^4$s combine to form an oxo. The oxo can be bound, for example, at the position alpha to the nitrogen of the azacycloalkyl.

In certain embodiments according to the first aspect of the invention, T is

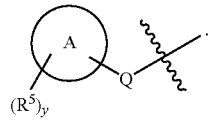

In these embodiments of the invention, Q is —(C$_0$-C$_3$ alkyl)-, in which each carbon of the (C$_0$-C$_3$ alkyl) is optionally and independently substituted with one or two R$^{16}$, in which each R$^{16}$ is independently selected from —(C$_1$-C$_6$ alkyl), —(C$_1$-C$_6$ fluoroalkyl), —(C$_0$-C$_6$ alkyl)-Ar; —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$, -halogen, —NO$_2$ and —CN, and two R$^{16}$ on the same carbon optionally combine to form an oxo. Q can be, for example, an unsubstituted (C$_1$-C$_3$ alkyl). In other embodiments of the invention, Q is a (C$_1$-C$_3$ alkyl) having as its only substitution a single oxo group. For example, in certain embodiments of the invention Q is —CH$_2$—; a single bond; or —C(O)— or —CH(CH$_3$)—.

The number of substituents on the ring system denoted by "A", y, in these embodiments is 0, 1, 2, 3 or 4. For example, in some embodiments of the invention, y is 0, 1, 2 or 3, for example 0, or 1. In one embodiment of the invention, y is not zero and at least one R$^5$ is halo, cyano, trifluoromethyl or trifluoromethoxy.

The ring system denoted by "A" is heteroaryl, aryl, cycloalkyl or heterocycloalkyl. For example, in one embodiment of the invention, the ring system denoted by "A" is an aryl or a heteroaryl. In one embodiment of the invention, the ring system denoted by "A" is an aryl. The ring system denoted by "A" can be, for example, a monocyclic aryl or heteroaryl.

For example, in one embodiment of the invention the ring system denoted by "A" is an aryl, such as a phenyl. In one embodiment of the invention, y is 1 and R$^5$ is attached to the phenyl para to Q. In another embodiment of the invention, y is 1 and R$^5$ is selected from the group consisting of halo, cyano, —(C$_1$-C$_4$ fluoroalkyl), —O—(C$_1$-C$_4$ fluoroalkyl), acyl, carboxylate, carboxamide and nitro. R$^5$ can be, for example, —Cl, —F, cyano, trifluoromethyl or trifluoromethoxy. In another embodiment of the invention, the

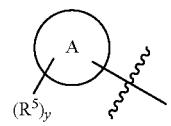

moiety is a 3,4-dihalophenyl.

In another embodiment of the invention, the ring system denoted by "A" is a heteroaryl. For example, in certain embodiments of the invention, the ring system denoted by "A" is a pyridiyl, a thienyl, or a furanyl.

In one embodiment according to the first aspect of the invention, the compound has structural formula (II):

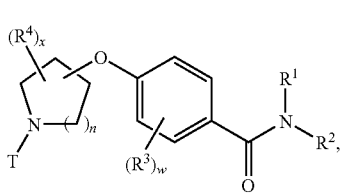
(II)

in which the variables are defined as described above with reference to formula (I).

In another embodiment according to the first aspect of the invention, the compound has the structural formula (III):

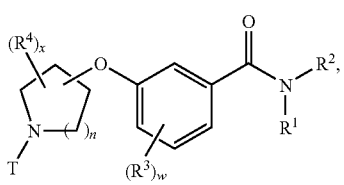
(III)

in which the variables are defined as described above with reference to formula (I).

For example, compounds according to certain embodiments of the first aspect of the invention have structural formula (IV):

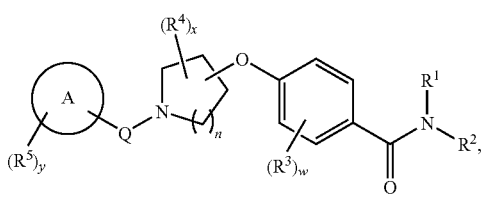
(IV)

in which the variables are defined as described above with reference to formula (I).

In other embodiments according to the first aspect of the invention, compounds of the present invention have structural formula (V):

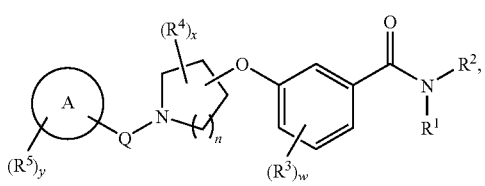
(V)

in which the variables are defined as described above with reference to formula (I).

In certain embodiments of the invention, n is 1 or 2. For example, in one embodiment according to the first aspect of the invention, n is 2.

In one embodiment according to the first aspect of the invention, the compound has structural formula (VI):

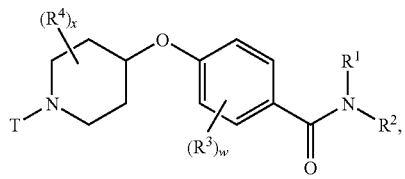
(VI)

in which the variables are defined as described above with reference to formula (I).

In another embodiment according to the first aspect of the invention, the compound has the structural formula (VII):

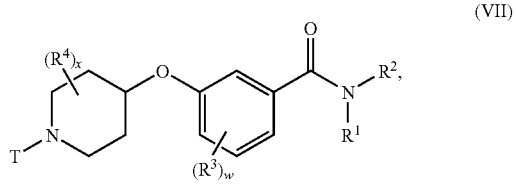
(VII)

in which the variables are defined as described above with reference to formula (I).

For example, compounds according to the first aspect of the invention can have structural formula (VIII):

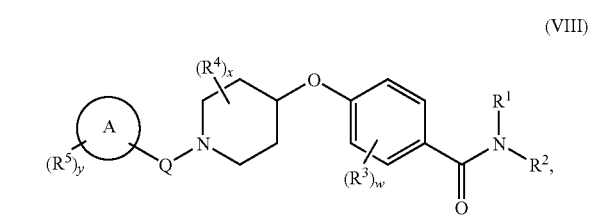
(VIII)

in which the variables are defined as described above with reference to formula (I).

In other embodiments according to the first aspect of the invention, compounds of the present invention have structural formula (IX):

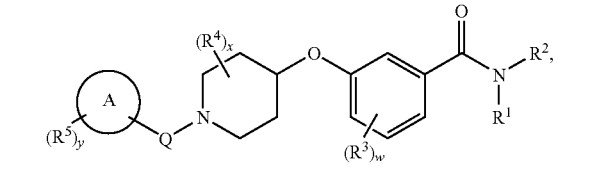
(IX)

in which the variables are defined as described above with reference to formula (I).

According to the first aspect of the invention, $R^1$ is —H and $R^2$ is -Hca. In certain embodiments according to the first aspect of the invention, $R^2$ is substituted with ($C_0$-$C_3$ alkyl)-Het or ($C_0$-$C_3$ alkyl)-Ar. In one embodiment according to the first aspect of the invention, $R^2$ is -(optionally-substituted azetidinyl), -(optionally-substituted pyrrolidinyl), -(optionally-substituted piperidinyl), or -(optionally-substituted azepanyl). For example, $R^2$ can be -(optionally substituted piperidinyl) or -(optionally substituted pyrrolidinyl).

In one embodiment according to the first aspect of the invention, $R^1$ is —H and $R^2$ is -(optionally-substituted azetidin-3-yl), -(optionally substituted piperidin-4-yl), -(optionally substituted pyrrolidin-3-yl) or -(optionally-substituted azepan-4-yl). For example, in one embodiment according to the first aspect of the invention, $R^2$ is -(optionally substituted piperidin-4-yl). In another embodiment according to the first aspect of the invention, $R^2$ is -(optionally substituted pyrrolidin-3-yl).

In certain embodiments of the invention, the azetidinyl, pyrrolidinyl, piperidinyl and azepanyl $R^2$ moieties described above are substituted at their 1-positions. For example, in one embodiment of the invention $R^2$ is substituted at its 1-position with ($C_0$-$C_3$ alkyl)-Ar or ($C_0$-$C_3$ alkyl)-Het. For example, in one embodiment of the invention the azetidinyl, pyrrolidinyl, piperidinyl or azepanyl $R^2$ moiety is substituted at its 1-position with an optionally substituted benzyl or an optionally substituted phenyl. In another embodiment of the invention, the azetidinyl, pyrrolidinyl, piperidinyl or azepanyl $R^2$ moiety is substituted at its 1-position with a benzyl substituted with an electron withdrawing group; or with a pyridinylmethyl substituted with an electron withdrawing group. For example, the benzyl or pyridinylmethyl can be substituted with an electron withdrawing group selected from the group consisting of halo, cyano, —($C_1$-$C_4$ fluoroalkyl), —O—($C_1$-$C_4$ fluoroalkyl), acyl groups, carboxylate groups, carboxamide groups, cyano groups, sulfonate groups, and nitro groups. In other embodiments of the invention, the azetidinyl, pyrrolidinyl, piperidinyl or azepanyl $R^2$ moiety is substituted at its 1-position with an unsubstituted benzyl or an unsubstituted phenyl.

In other embodiments of the invention, the azetidinyl, pyrrolidinyl, piperidinyl or azepanyl $R^2$ moiety is substituted at its 1-position with an optionally substituted pyridinylmethyl, an optionally substituted furanylmethyl or an optionally substituted thienylmethyl. For example, the azetidinyl, pyrrolidinyl, piperidinyl or azepanyl $R^2$ moiety can be substituted with an unsubstituted pyridinylmethyl, an unsubstituted furanylmethyl, or an unsubstituted thienylmethyl.

In other embodiments of the invention, the azetidinyl, pyrrolidinyl, piperidinyl or azepanyl $R^2$ moiety is substituted at its 1-position with —CO—O—($C_0$-$C_6$ alkyl), —CO-Het, —CO—Ar or —$SO_2$—($C_0$-$C_6$ alkyl).

According to the first aspect of the invention, the number of substituents on the central phenyl ring, w, is 0, 1, 2, 3 or 4. For example, in one embodiment of the invention, w is 0, 1 or 2. In another embodiment according to the first aspect of the invention, w is 0. In other embodiments according to the first aspect of the invention, w is at least 1, and at least one $R^3$ is selected from the group consisting of halo, cyano, —($C_1$-$C_4$ fluoroalkyl), —O—($C_1$-$C_4$ fluoroalkyl), acyl, carboxylate, carboxamide and nitro.

In certain embodiments according to the first aspect of the invention, $R^3$ is selected from the group consisting of halo, cyano, —($C_1$-$C_4$ fluoroalkyl), —O—($C_1$-$C_4$ fluoroalkyl), acyl, carboxylate, carboxamide and nitro. $R^3$ can be, for example, —Cl or —F. For example, compounds according to these embodiments of the invention can have structural formula (X):

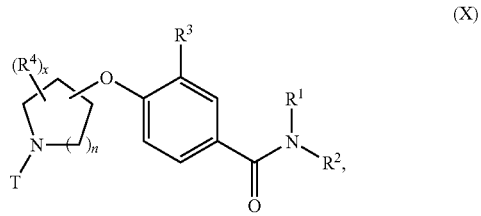

(X)

in which the remaining variables are defined as described above with reference to formula (I). Certain other compounds according to these embodiments of the invention have structural formula (XI):

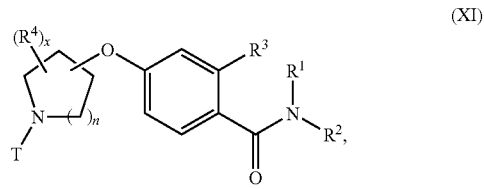

(XI)

in which the remaining variables are defined as described above with reference to formula (I).

According to the first aspect of the invention, the number of substituents on the ethereal azacycloalkane ring, x, is 0, 1, 2, 3 or 4. In one embodiment according to the first aspect of the invention, x is 0, 1, 2 or 3. For example, x can be 0, or can be 1 or 2.

Compounds according to one embodiment of the first aspect of the invention have the structural formula (XII):

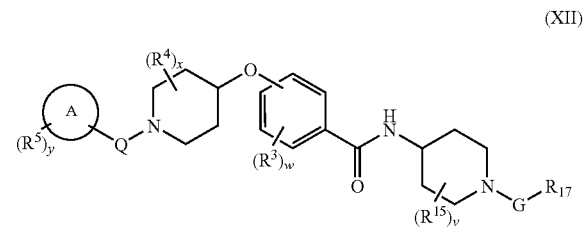

(XII)

in which Q and G are each independently a bond, —$CH_2$—, —$C(H)(R^{16})$— or —$C(R^{16})_2$—; v is 0, 1, 2, 3 or 4; each $R^{15}$ is independently selected from —($C_1$-$C_6$ alkyl), —($C_1$-$C_6$ fluoroalkyl), —($C_0$-$C_6$ alkyl)-Ar; —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-$S(O)_{0-2}R^{10}$, -halogen, —$NO_2$ and —CN, and two $R^{15}$ on the same carbon optionally combine to form oxo; $R^{17}$ is Het or Ar, and all other variables are defined as described above with reference to formula (I). In one embodiment of the invention, v is 0. In one embodiment of the invention, Q is a single bond. In another embodiment of the invention, G is —$CH_2$— or —CO—. For example, in one embodiment of the invention, Q is a single bond and G is —$CH_2$— or —CO—. The ethereal linkage of the piperidine to the benzamide can be at any aryl carbon. For example, the ether can be substituted at the 3-position or the 4-position of the benzamide. In one embodiment of the invention, two $R^{15}$s combine to form an oxo, which can be bound, for example, at a position alpha to the piperidine nitrogen. As described above, in certain embodiments of the invention the ring system denoted by "A" is aryl or heteroaryl. In one embodiment of the invention, the ring system denoted by "A" is substituted with one or more electron-withdrawing groups. In another embodiment of the invention, $R^{17}$ is substituted with one or more electron-withdrawing groups.

Compounds according to certain embodiments of the first aspect of the invention have the structural formula (XIII):

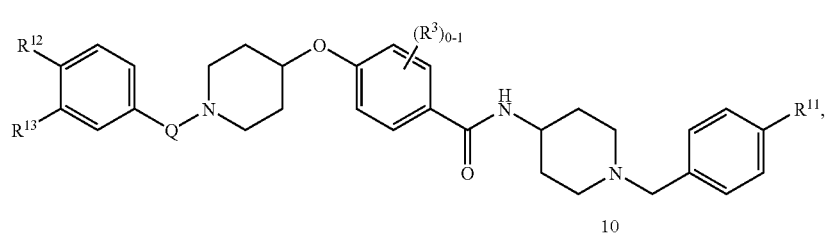

(XIII)

in which Q is —CH$_2$— or a single bond; R$^3$ is halo; R$^{11}$ is H, halo, cyano, or a carboxylate; and R$^{12}$ and R$^{13}$ are independently H, trifluoromethyl, trifluoromethoxy, halo or cyano.

Compounds according to other embodiments according to the first aspect of the invention have structural formula (XIV):

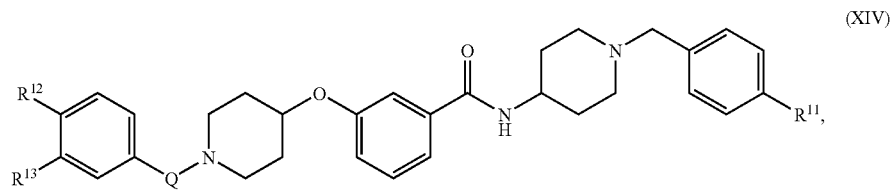

(XIV)

in which Q is —CH$_2$— or a single bond; R$^{11}$ is H, halo, cyano, or a carboxylate; and R$^{12}$ and R$^{13}$ are independently H, trifluoromethyl, trifluoromethoxy, halo or cyano.

Compounds according to certain embodiments according to the first aspect of the invention have the structural formula (XV):

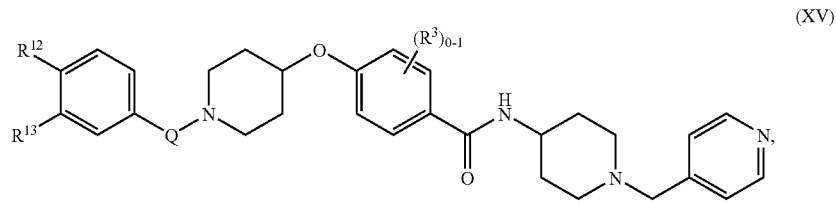

(XV)

in which Q is —CH$_2$— or a single bond; R$^3$ is halo; and R$^{12}$ and R$^{13}$ are independently H, trifluoromethyl, trifluoromethoxy, halo or cyano.

Compounds according to other embodiments according to the first aspect of the invention have the structural formula (XVI):

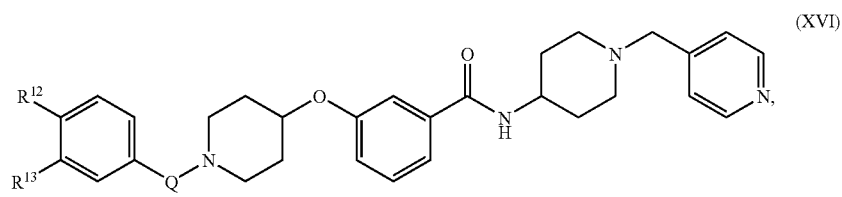

(XVI)

in which Q is —CH$_2$— or a single bond; and R$^{12}$ and R$^{13}$ are independently H, trifluoromethyl, trifluoromethoxy, halo or cyano.

Examples of compounds of the present invention according to structural formula (I) include those listed below in Table 1. These compounds can be made according to the general scheme described below, for example using a procedure similar to that described below in Example 1.

TABLE 1

| Cpd | Name | Structure |
|---|---|---|
| 14 | N-(1-benzylpiperidin-4-yl)-4-(1-benzylpiperidin-4-yloxy)-3-chlorobenzamide | 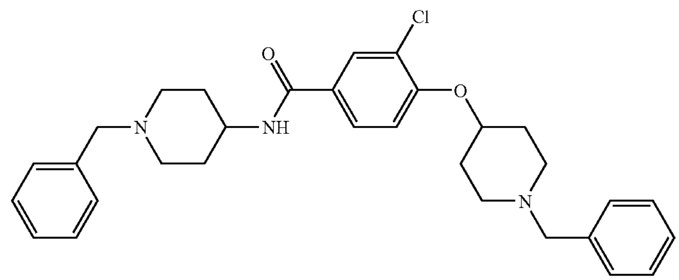 |
| 15 | N-(1-benzylpiperidin-4-yl)-3-chloro-4-(1-((2,3-dihydrobenzo[b][1,4]dioxin-6-yl)methyl)piperidin-4-yloxy)benzamide | 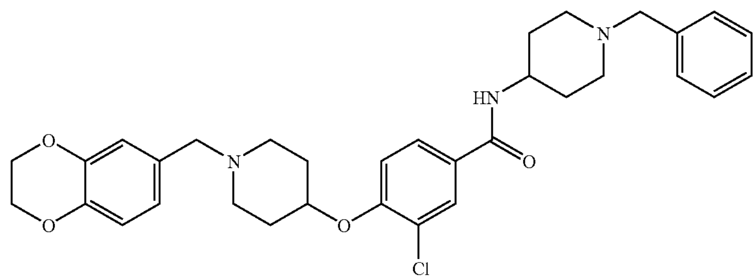 |
| 16 | N-(1-benzylpiperidin-4-yl)-4-(1-(4-tert-butylbenzyl)piperidin-4-yloxy)-3-chlorobenzamide | 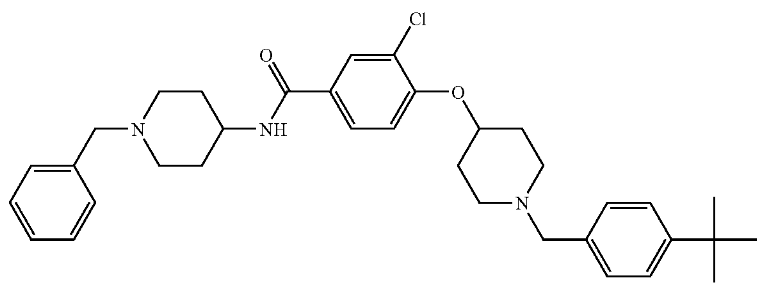 |
| 17 | N-(1-benzylpiperidin-4-yl)-3-chloro-4-(1-(4-(trifluoromethyl)phenyl)piperidin-4-yloxy)benzamide | 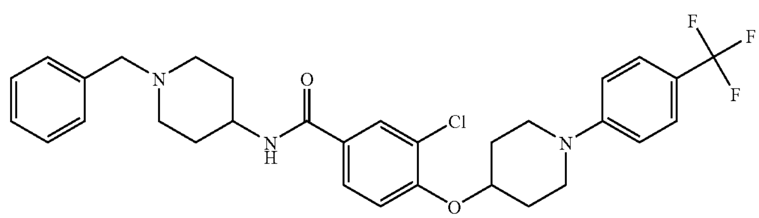 |
| 18 | N-(1-benzylpiperidin-4-yl)-3-chloro-4-(1-(4-(trifluoromethyl)benzoyl)piperidin-4-yloxy)benzamide | 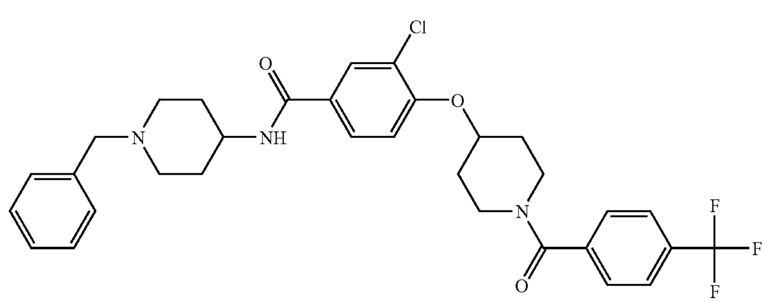 |

TABLE 1-continued

| Cpd | Name | Structure |
|---|---|---|
| 19 | N-(1-benzylpiperidin-4-yl)-3-chloro-4-(1-(4-fluorobenzyl)piperidin-4-yloxy)benzamide | 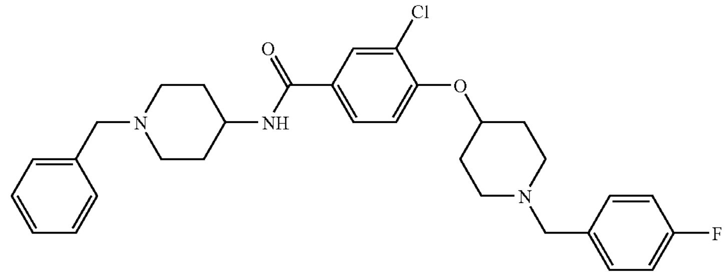 |
| 20 | N-(1-benzylpiperidin-4-yl)-3-fluoro-4-(1-(4-tert-butylbenzyl)piperidin-4-yloxy)benzamide | 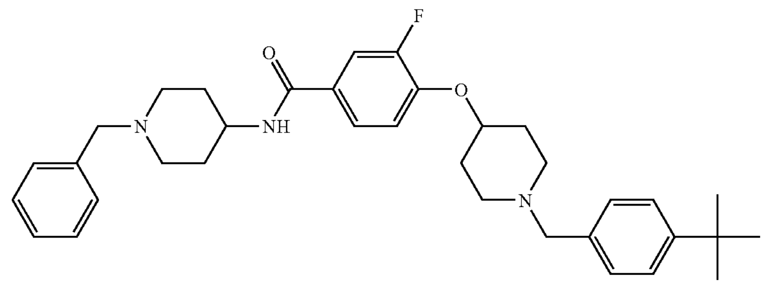 |
| 21 | N-(1-benzylpiperidin-4-yl)-3-fluoro-4-(1-(1-phenylethyl)piperidin-4-yloxy)benzamide | 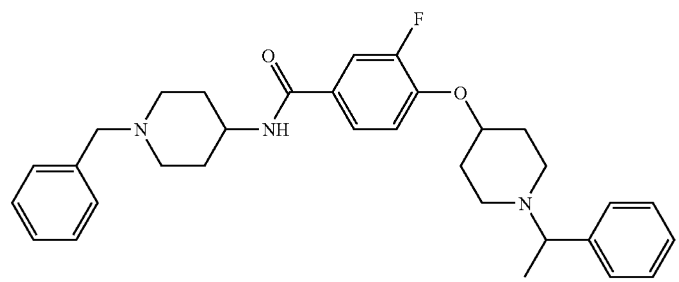 |
| 22 | N-(1-benzylpiperidin-4-yl)-3-chloro-4-(1-(4-fluorobenzoyl)piperidin-4-yloxy)benzamide | 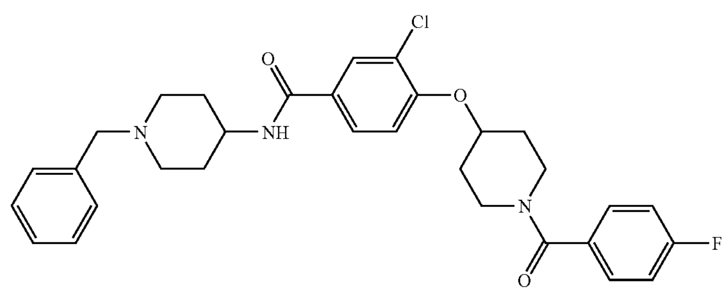 |
| 23 | N-(1-benzylpiperidin-4-yl)-3-fluoro-4-(1-(4-(trifluoromethyl)phenyl)piperidin-4-yloxy)benzamide | 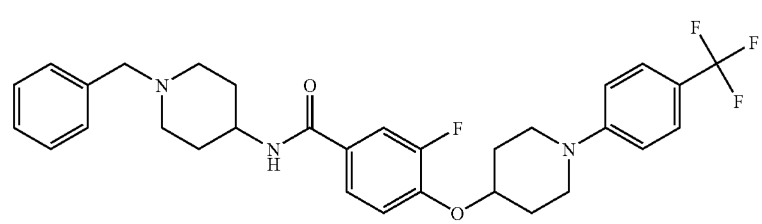 |
| 24 | N-(1-benzylpiperidin-4-yl)-3-chloro-4-(1-(2-(trifluoromethyl)benzyl)piperidin-4-yloxy)benzamide | 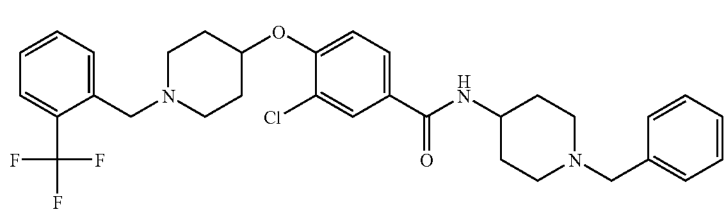 |

TABLE 1-continued

| Cpd | Name | Structure |
|---|---|---|
| 25 | 3-fluoro-N-(1-phenylpiperidin-4-yl)-4-(1-(4-(trifluoromethyl)phenyl)piperidin-4-yloxy)benzamide | 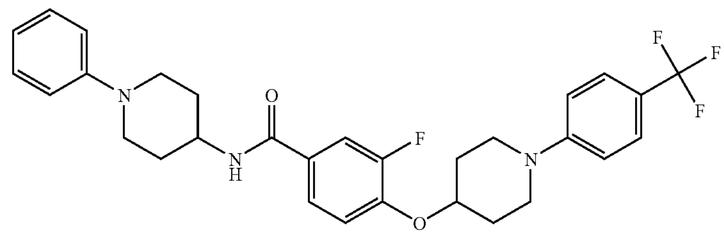 |
| 26 | tert-butyl 4-(3-fluoro-4-(1-(4-(trifluoromethyl)phenyl)piperidin-4-yloxy)benzamido)piperidine-1-carboxylate | 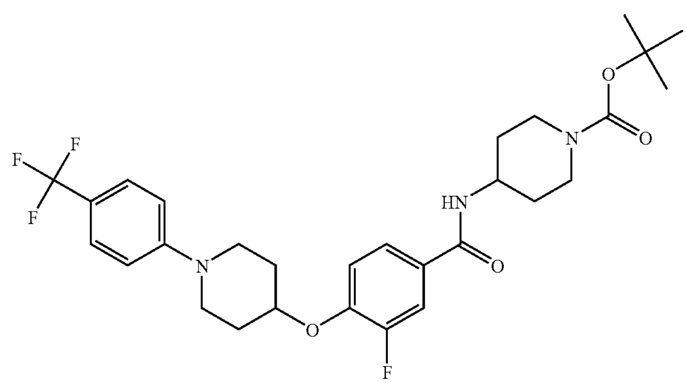 |
| 27 | 3-fluoro-N-(1-(4-fluorobenzyl)piperidin-4-yl)-4-(1-(4-(trifluoromethyl)phenyl)piperidin-4-yloxy)benzamide | 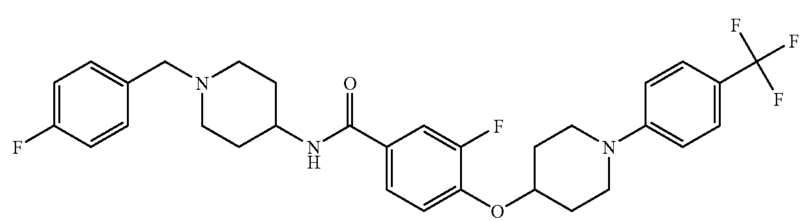 |
| 28 | 3-fluoro-N-(1-(pyridin-4-ylmethyl)piperidin-4-yl)-4-(1-(4-(trifluoromethyl)phenyl)piperidin-4-yloxy)benzamide | 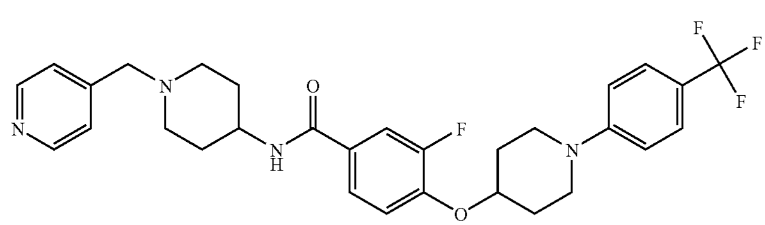 |
| 29 | 3-fluoro-N-(1-(pyridin-3-ylmethyl)piperidin-4-yl)-4-(1-(4-(trifluoromethyl)phenyl)piperidin-4-yloxy)benzamide | 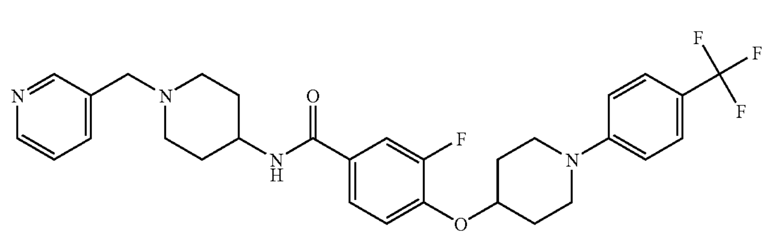 |

TABLE 1-continued

| Cpd | Name | Structure |
|---|---|---|
| 30 | 3-fluoro-N-(1-pivaloylpiperidin-4-yl)-4-(l-(4-(trifluoromethyl)phenyl)piperidin-4-yloxy)benzamide | 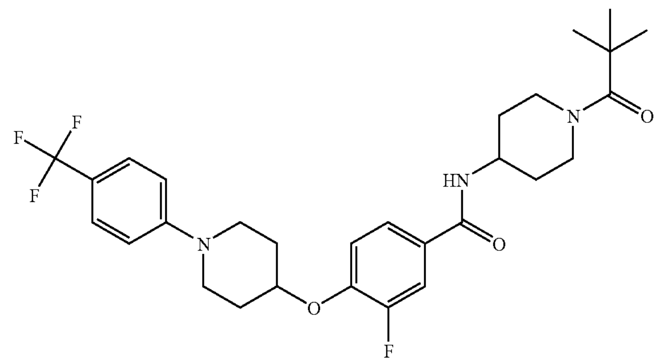 |
| 31 | 3-fluoro-N-(1-(4-fluorobenzoyl)piperidin-4-yl)-4-(1-(4-(trifluoromethyl)phenyl)piperidin-4-yloxy)benzamide | 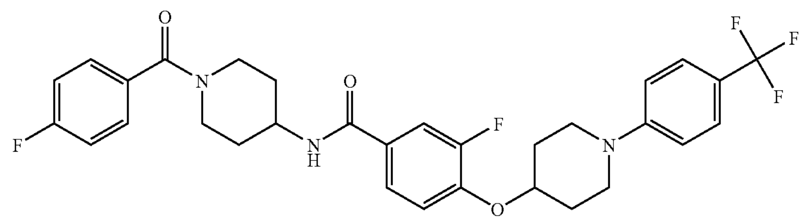 |
| 32 | 3-fluoro-N-(1-(pyridin-2-ylmethyl)piperidin-4-yl)-4-(1-(4-(trifluoromethyl)phenyl)piperidin-4-yloxy)benzamide | 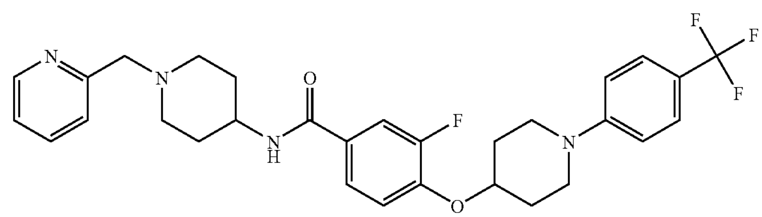 |
| 33 | methyl 4-((4-(3-fluoro-4-(1-(4-(trifluoromethyl)phenyl)piperidin-4-yloxy)benzamido)piperidin-1-yl)methyl)benzoate | 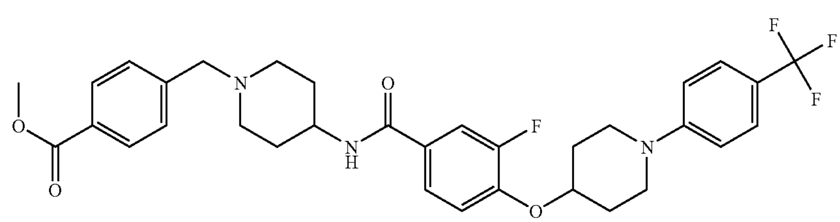 |
| 34 | 3-fluoro-N-(1-(isopropylsulfonyl)piperidin-4-yl)-4-(1-(4-(trifluoromethyl)phenyl)piperidin-4-yloxy)benzamide | 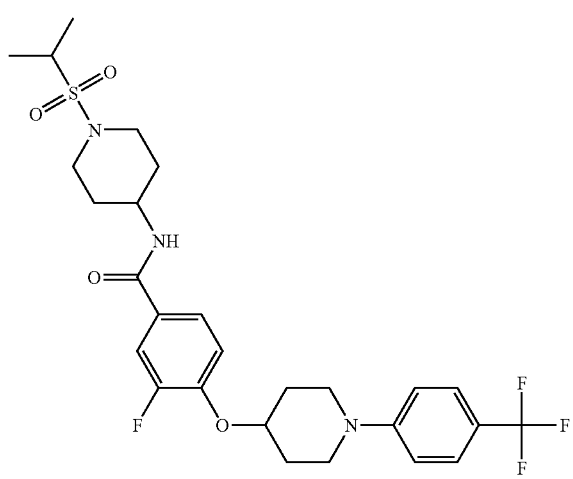 |

TABLE 1-continued

| Cpd | Name |
|---|---|
| 35 | 4-((4-(3-fluoro-4-(1-(4-(trifluoromethyl)phenyl)piperidin-4-yloxy)benzamido)piperidin-1-yl)methyl)benzoic acid |
| 36 | 4-(1-(4-tert-butylbenzyl)piperidin-4-yloxy)-3-fluoro-N-(1-phenylpiperidin-4-yl)benzamide |
| 37 | N-(1-benzylpiperidin-4-yl)-3-fluoro-4-(1-(pyridin-4-ylmethyl)piperidin-4-yloxy)benzamide |
| 38 | N-(1-benzylpiperidin-4-yl)-3-fluoro-4-(1-(pyridin-3-ylmethyl)piperidin-4-yloxy)benzamide |
| 39 | N-(1-benzylpiperidin-4-yl)-3-fluoro-4-(1-(pyridin-2-ylmethyl)piperidin-4-yloxy)benzamide |

TABLE 1-continued

| Cpd | Name | Structure |
|---|---|---|
| 40 | 3-fluoro-N-(1-isonicotinoylpiperidin-4-yl)-4-(1-(4-(trifluoromethyl)phenyl)piperidin-4-yloxy)benzamide | 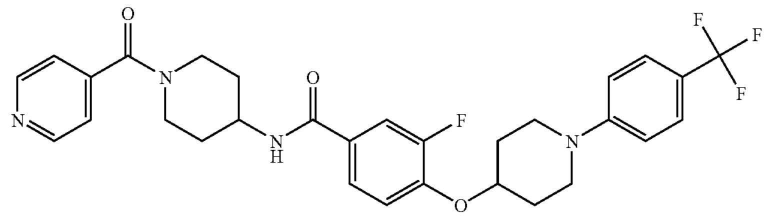 |
| 41 | N-(1-benzylpiperidin-4-yl)-4-(1-(4-cyanobenzyl)piperidin-4-yloxy)-3-fluorobenzamide | 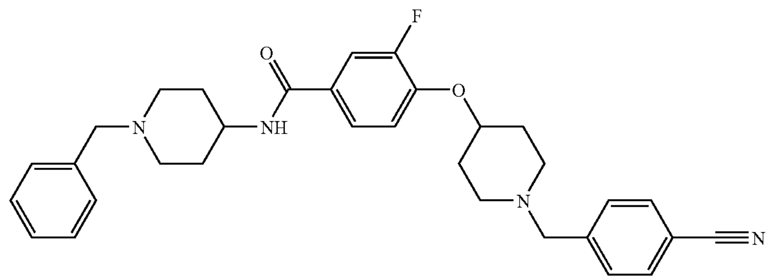 |
| 42 | N-(1-benzylpiperidin-4-yl)-3-fluoro-4-(1-(4-methylbenzyl)piperidin-4-yloxy)benzamide | 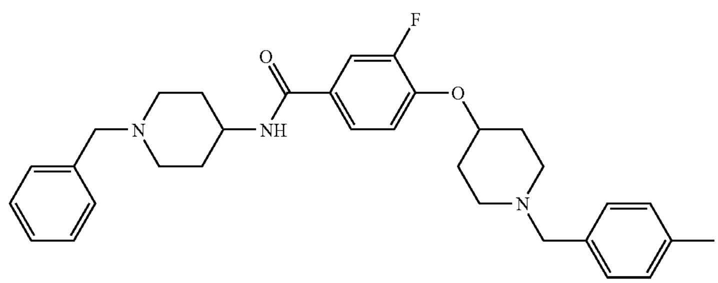 |
| 43 | N-(1-(4-cyanobenzyl)piperidin-4-yl)-3-fluoro-4-(1-(4-(trifluoromethyl)phenyl)piperidin-4-yloxy)benzamide | 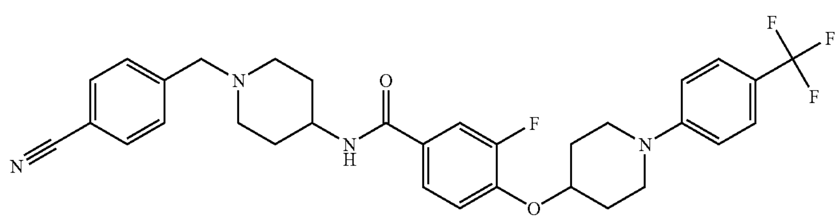 |
| 44 | 4-(1-(4-cyanophenyl)piperidin-4-yloxy)-3-fluoro-N-(1-(pyridin-4-ylmethyl)piperidin-4-yl)benzamide | 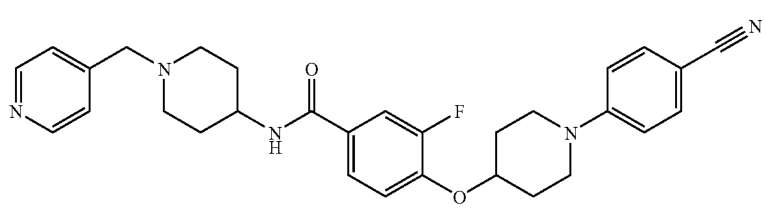 |
| 45 | N-(1-(4-cyanobenzyl)piperidin-4-yl)-4-(1-(4-cyanophenyl)piperidin-4-yloxy)-3-fluorobenzamide | 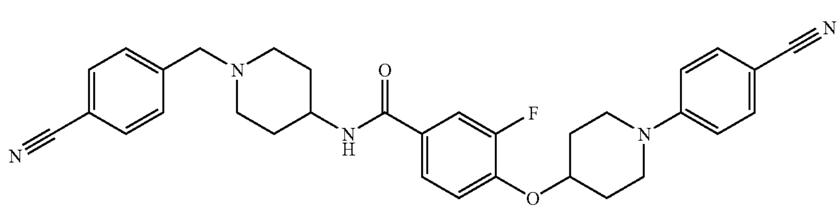 |

TABLE 1-continued

| Cpd | Name | Structure |
|---|---|---|
| 46 | N-(1-benzylpiperidin-4-yl)-3-(1-(4-(trifluoromethyl)phenyl)piperidin-4-yloxy)benzamide | 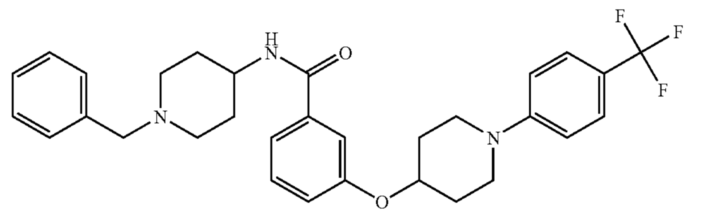 |
| 47 | N-(1-benzylpiperidin-4-yl)-2-chloro-4-(1-(4-(trifluoromethyl)phenyl)piperidin-4-yloxy)benzamide | 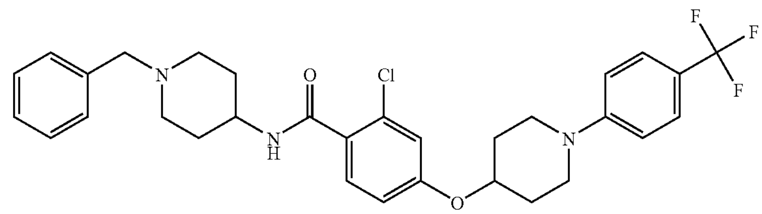 |
| 48 | N-(1-benzylpiperidin-4-yl)-3-(1-(4-cyanophenyl)piperidin-4-yloxy)benzamide | 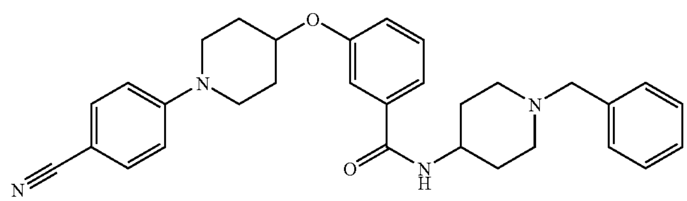 |
| 49 | N-(1-benzylpiperidin-4-yl)-2-chloro-4-(1-(4-cyanophenyl)piperidin-4-yloxy)benzamide | 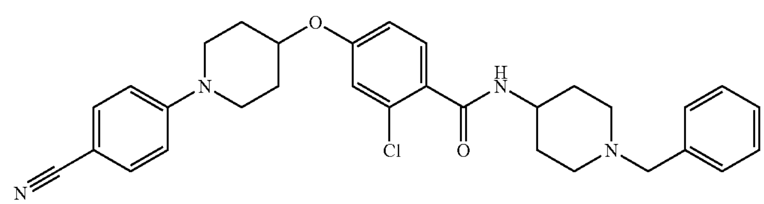 |
| 50 | N-(1-benzylpiperidin-4-yl)-3-(1-(4-cyanobenzyl)piperidin-4-yloxy)benzamide | 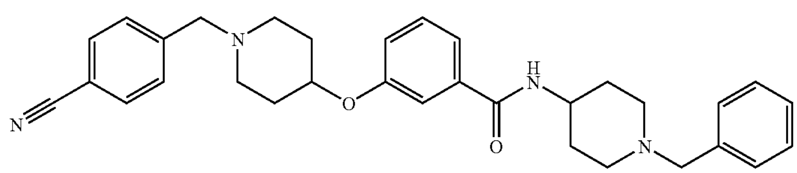 |
| 51 | N-(1-benzylpiperidin-4-yl)-2-chloro-4-(1-(4-cyanobenzyl)piperidin-4-yloxy)benzamide | 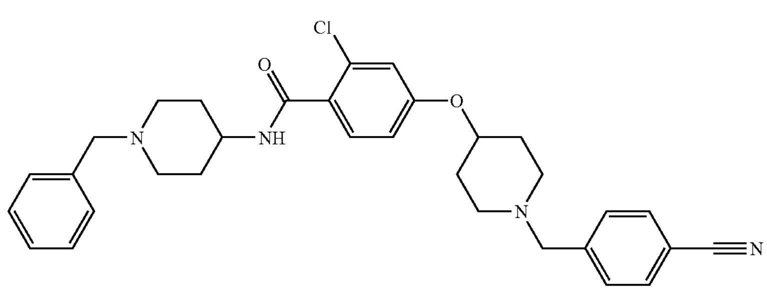 |
| 52 | N-(1-benzylpiperidin-4-yl)-3-(1-(4-(trifluoromethyl)benzyl)piperidin-4-yloxy)benzamide | 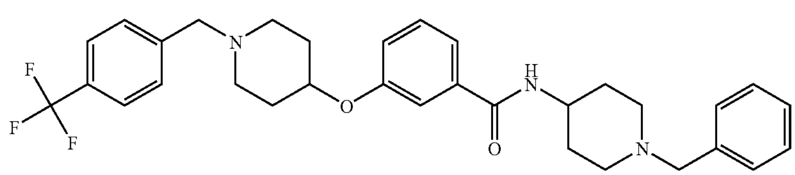 |

TABLE 1-continued

| Cpd | Name | Structure |
|---|---|---|
| 53 | N-(1-benzylpiperidin-4-yl)-3-(1-(pyridin-4-yl)piperidin-4-yloxy)benzamide | 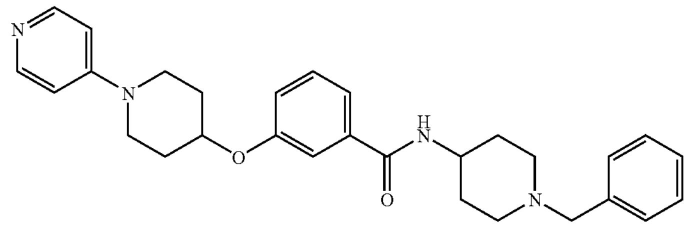 |
| 54 | N-(1-benzylpiperidin-4-yl)-3-chloro-4-(1-(4-(trifluoromethoxy)benzyl)piperidin-4-yloxy)benzamide | 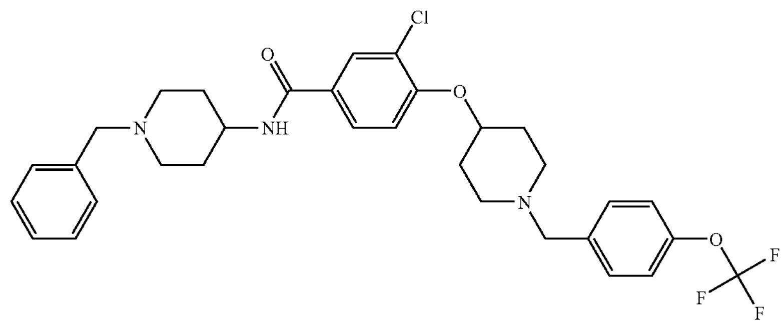 |
| 55 | N-(1-benzylpiperidin-4-yl)-3-fluoro-4-(1-(4-(trifluoromethyl)benzyl)piperidin-4-yloxy)benzamide | 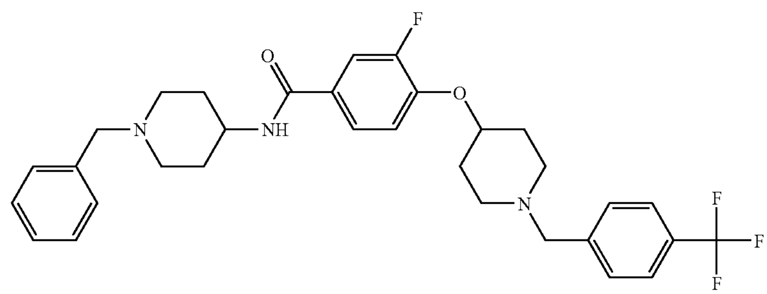 |
| 56 | N-(1-benzylpiperidin-4-yl)-3-chloro-4-(1-(4-(trifluoromethyl)benzyl)piperidin-4-yloxy)benzamide | 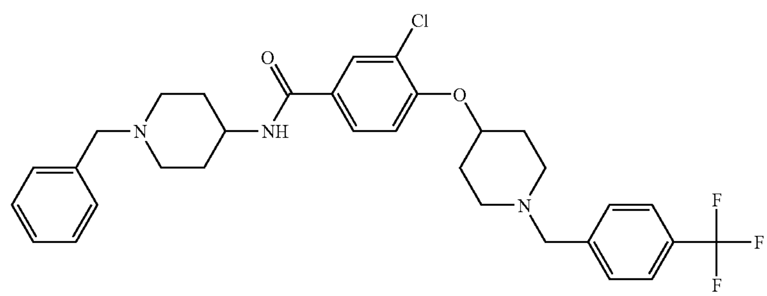 |
| 57 | N-(1-benzylpiperidin-4-yl)-3-fluoro-4-(1-(4-(trifluoromethoxy)benzyl)piperidin-4-yloxy)benzamide | 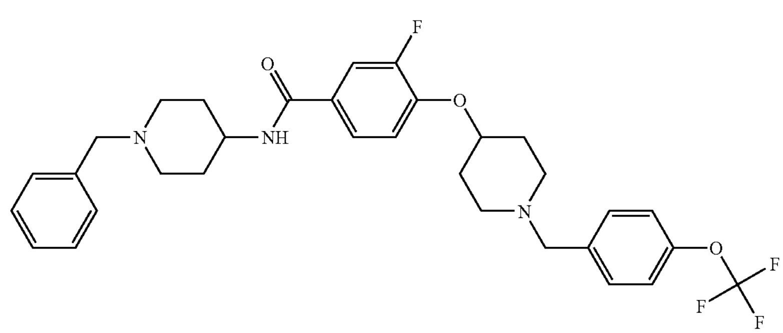 |

TABLE 1-continued

| Cpd | Name | Structure |
|---|---|---|
| 58 | 3-chloro-N-(1-methylpiperidin-4-yl)-4-(1-(4-(trifluoromethyl)benzyl)piperidin-4-yloxy)benzamide | 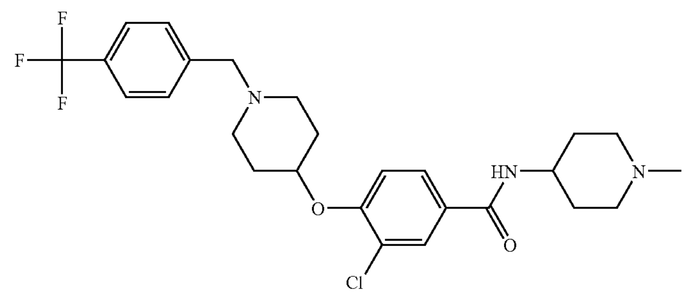 |
| 59 | N-(1-benzylpiperidin-4-yl)-3-fluoro-4-(1-(3-(trifluoromethyl)benzyl)piperidin-4-yloxy)benzamide | 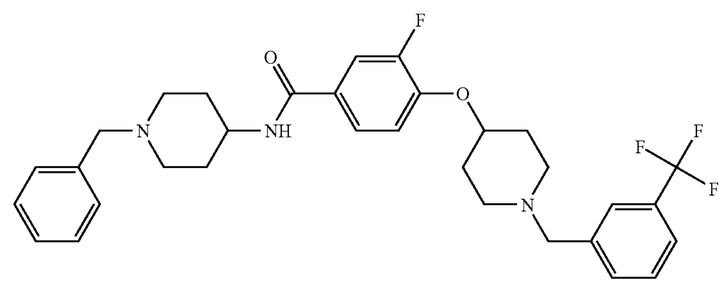 |
| 60 | N-(1-benzylpiperidin-4-yl)-3-chloro-4-(1-(3-(trifluoromethyl)benzyl)piperidin-4-yloxy)benzamide | 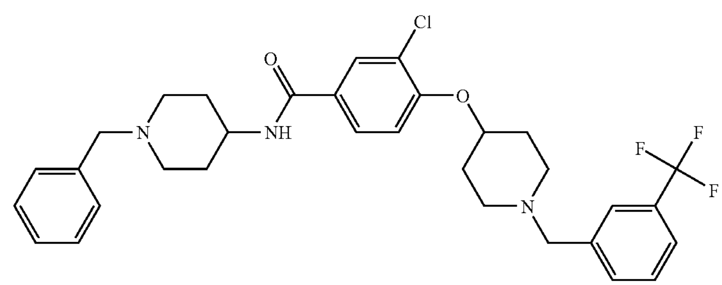 |
| 61 | N-(1-benzylpiperidin-4-yl)-3-fluoro-4-(1-(4-fluorobenzyl)piperidin-4-yloxy)benzamide | 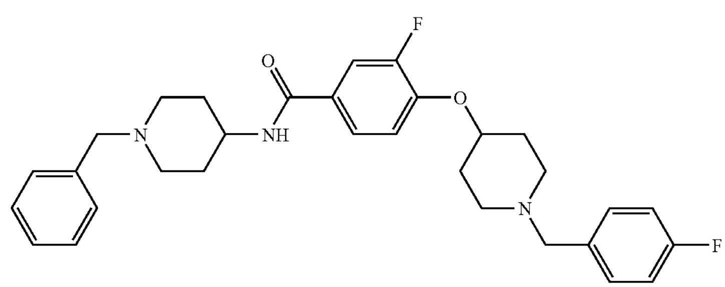 |
| 62 | N-(1-benzylpiperidin-4-yl)-3,5-dichloro-4-(1-(3-(trifluoromethyl)benzyl)piperidin-4-yloxy)benzamide | 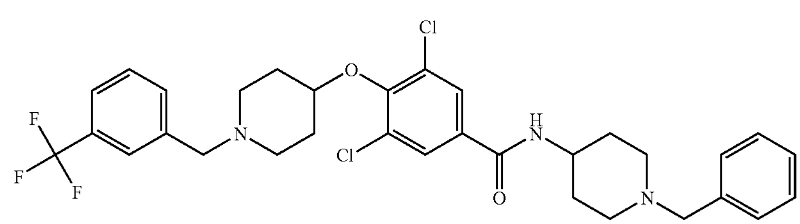 |
| 63 | N-(1-benzylpiperidin-4-yl)-4-(1-(4-trifluoromethoxy)benzyl)piperidin-4-yloxy)benzamide | 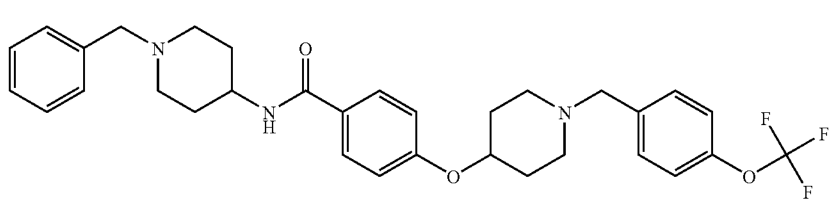 |

TABLE 1-continued

| Cpd | Name | Structure |
|-----|------|-----------|
| 64 | N-(1-benzylpiperidin-4-yl)-4-(1-(4-chlorobenzyl)piperidin-4-yloxy)-3-fluorobenzamide | 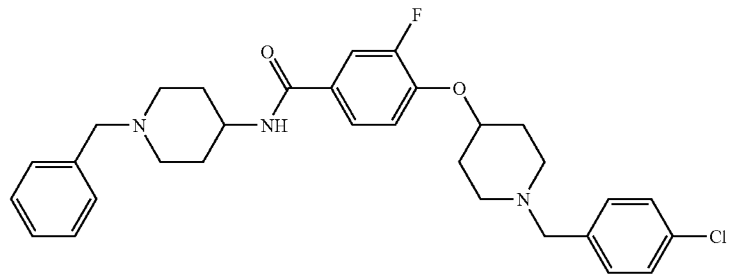 |
| 65 | N-(1-benzylpiperidin-4-yl)-3-chloro-4-(1-(4-chlorobenzyl)piperidin-4-yloxy)benzamide | 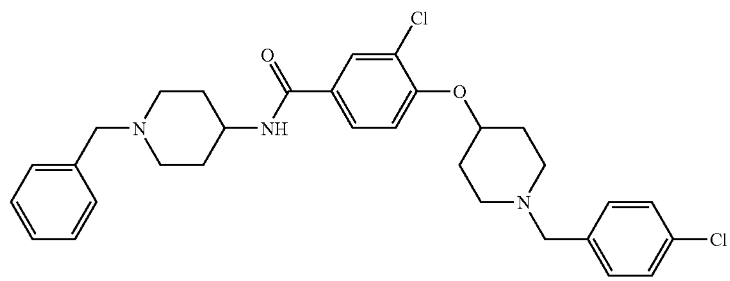 |
| 66 | 3-chloro-4-(1-(4-chlorobenzyl)piperidin-4-yloxy)-N-(1-(4-fluorobenzyl)piperidin-4-yl)benzamide | 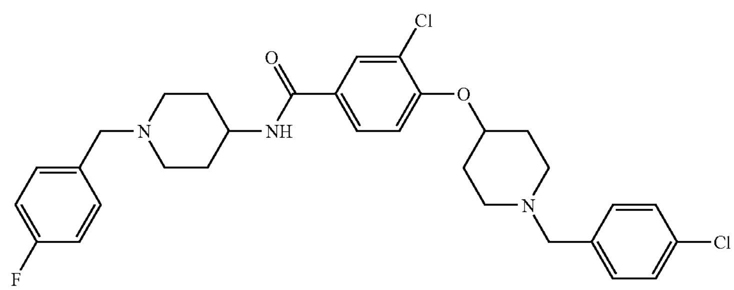 |
| 67 | N-(1-benzylpiperidin-4-yl)-3-chloro-4-(1-(4-cyanobenzyl)piperidin-4-yloxy)benzamide | 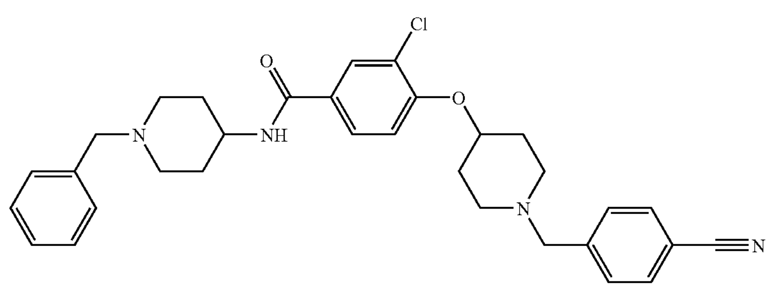 |
| 68 | 3-chloro-N-(1-(4-fluorobenzyl)piperidin-4-yl)-4-(1-(4-methylbenzyl)piperidin-4-yloxy)benzamide | 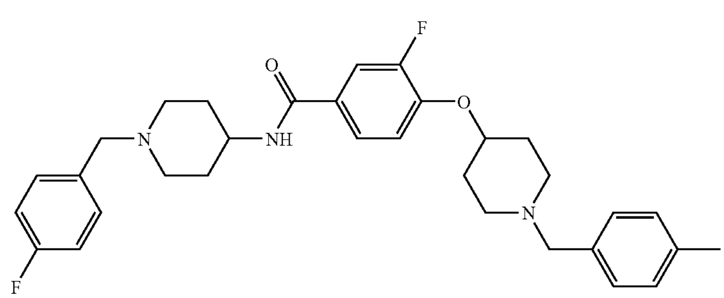 |

TABLE 1-continued

| Cpd | Name | Structure |
|---|---|---|
| 69 | N-(1-benzylpiperidin-4-yl)-4-(1-(3,4-difluorobenzyl)piperidin-4-yloxy)-3-fluorobenzamide | 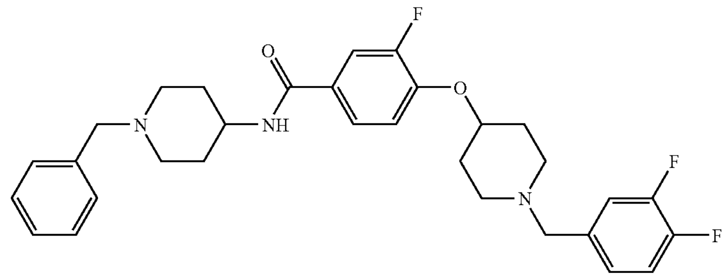 |
| 70 | N-(1-(4-chlorobenzyl)piperidin-4-yl)-4-(1-(4-cyanobenzyl)piperidin-4-yloxy)-3-fluorobenzamide | 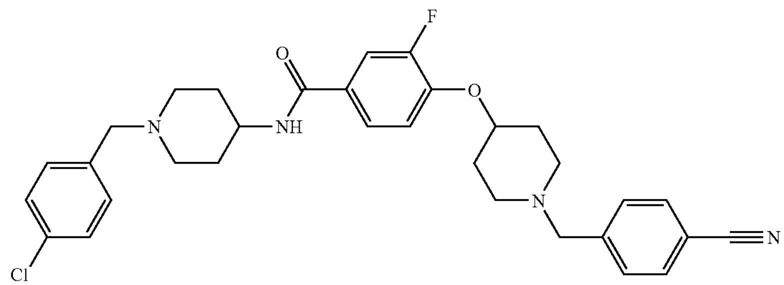 |
| 71 | N-(1-(4-chlorobenzyl)piperidin-4-yl)-4-(1-(3,4-difluorobenzyl)piperidin-4-yloxy)-3-fluorobenzamide | 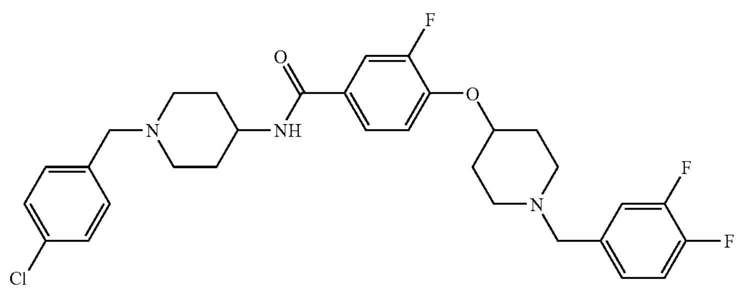 |
| 72 | N-(1-(4-chlorobenzyl)piperidin-4-yl)-4-(1-(4-chlorobenzyl)piperidin-4-yloxy)-3-fluorobenzamide | 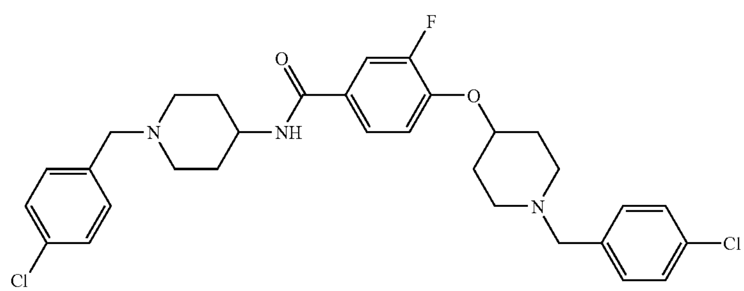 |
| 73 | N-(1-(4-chlorobenzyl)piperidin-4-yl)-3-fluoro-4-(1-(4-methylbenzyl)piperidin-4-yloxy)benzamide | 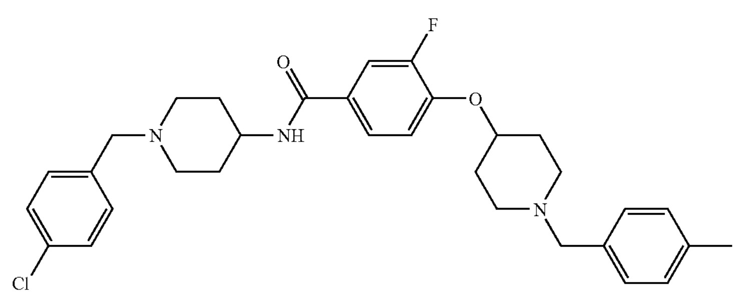 |

TABLE 1-continued

| Cpd | Name | Structure |
|---|---|---|
| 74 | N-(1-benzylpiperidin-4-yl)-3-chloro-4-(1-(3,4-difluorobenzyl)pipendin-4-yloxy)benzamide | 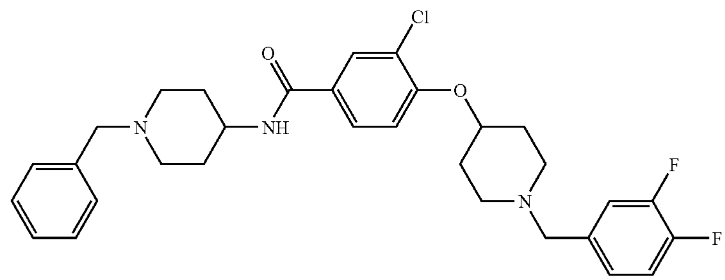 |
| 75 | N-(1-benzylpiperidin-4-yl)-3,5-dichloro-4-(1-(4-chlorobenzyl)piperidin-4-yloxy)benzamide | 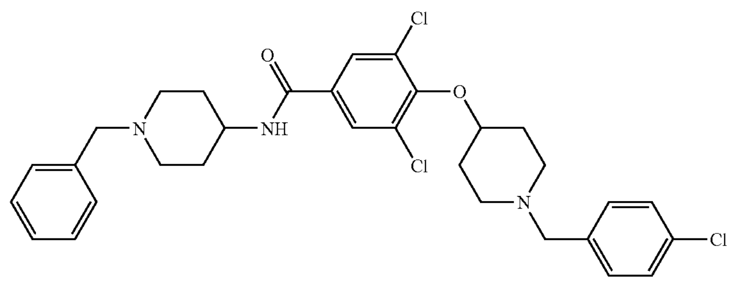 |
| 76 | N-(1-benzylpiperidin-4-yl)-3,5-dichloro-4-(1-(3,4-difluorobenzyl)piperidin-4-yloxy)benzamide | 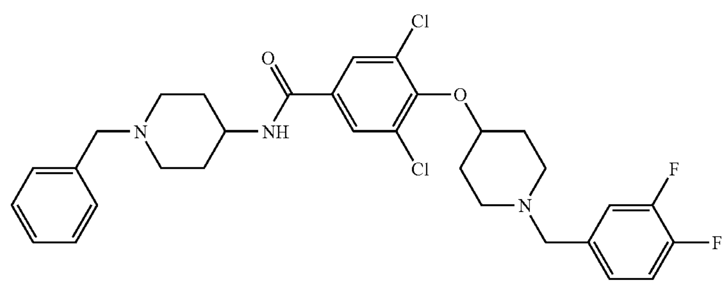 |
| 77 | N-(1-benzylpiperidin-4-yl)-3,5-dichloro-4-(1-(4-cyanobenzyl)piperidin-4-yloxy)benzamide | 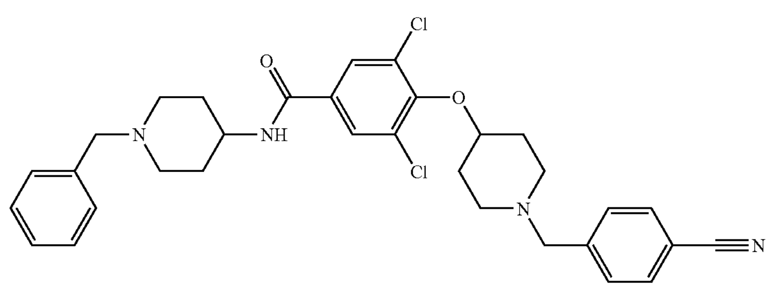 |
| 78 | tert-butyl 4-(4-(1-(4-cyanobenzyl)piperidin-4-yloxy)benzamido)piperidine-1-carboxylate | 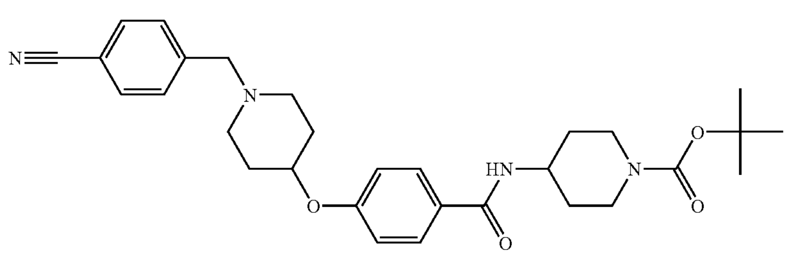 |

TABLE 1-continued

| Cpd | Name | Structure |
|---|---|---|
| 79 | 4-(1-(4-cyanobenzyl)piperidin-4-yloxy)-N-(piperidin-4-yl)benzamide | 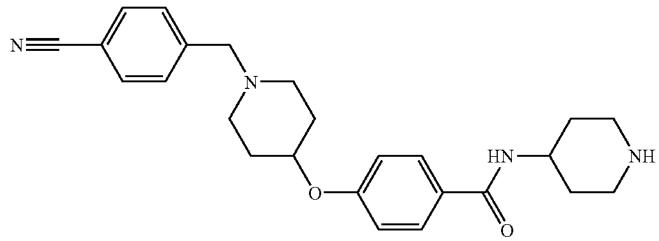 |
| 80 | N-(1-(4-chlorobenzyl)piperidin-4-yl)-4-(1-(3,4-dichlorobenzyl)piperidin-4-yloxy)-3-fluorobenzamide | 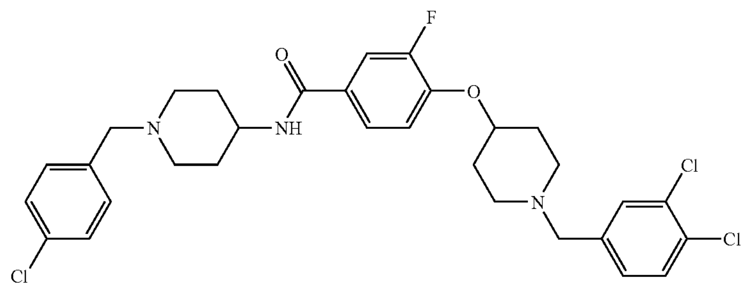 |
| 81 | N-(1-(4-chlorobenzyl)piperidin-4-yl)-4-(1-(4-cyanophenyl)piperidin-4-yloxy)-3-fluorobenzamide | 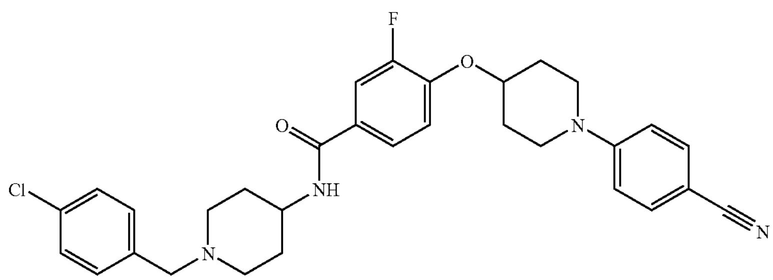 |
| 82 | N-(1-benzylpiperidin-4-yl)-4-(1-(3,4-dichlorobenzyl)piperidin-4-yloxy)-3-fluorobenzamide | 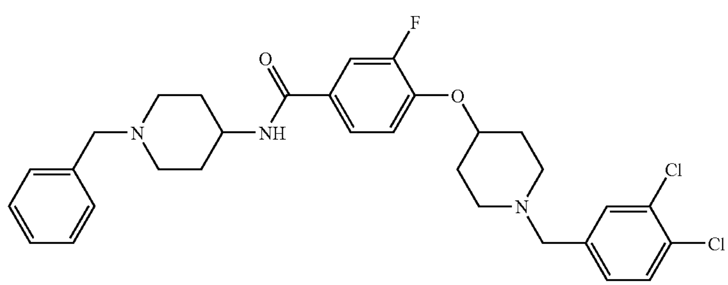 |
| 83 | 4-(1-(4-cyanobenzyl)piperidin-4-yloxy)-N-(1-(pyridin-4-ylmethyl)piperidin-4-yl)benzamide | 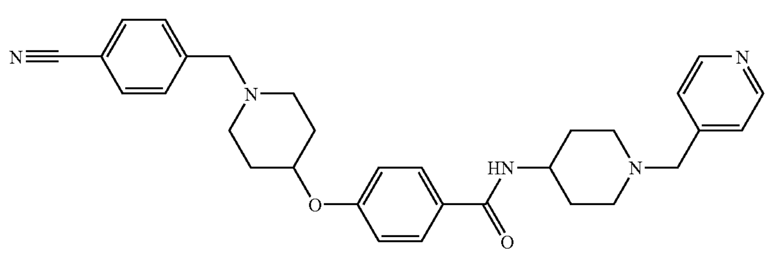 |

TABLE 1-continued

| Cpd | Name | Structure |
|---|---|---|
| 84 | N-(1-benzylpiperidin-4-yl)-3-chloro-4-(1-(3,4-dichlorobenzyl)piperidin-4-yloxy)benzamide | 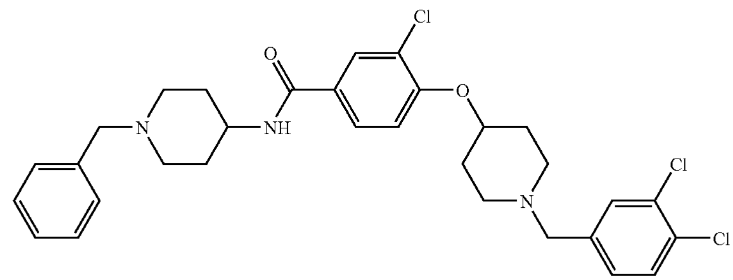 |
| 85 | 4-(1-(4-cyanobenzyl)piperidin-4-yloxy)-N-(1-(pyridin-2-ylmethyl)piperidin-4-yl)benzamide | 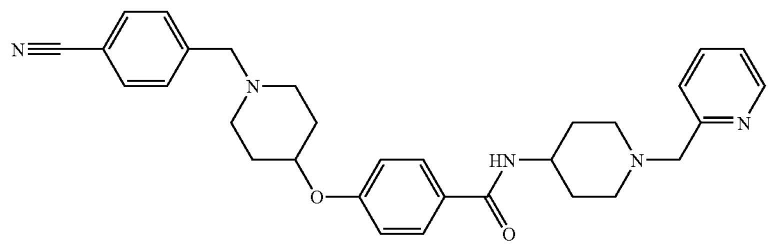 |
| 86 | N-(1-benzylpiperidin-4-yl)-3-(1-(pyridin-2-yl)piperidin-4-yloxy)benzamide | 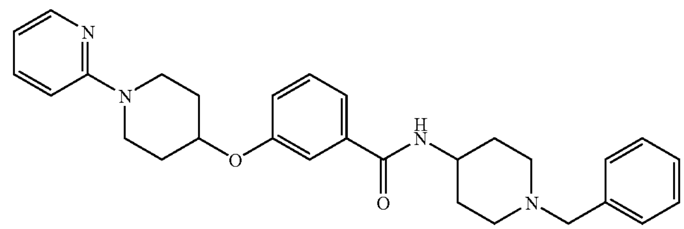 |
| 87 | N-(1-(pyridin-4-ylmethyl)piperidin-4-yl)-3-(1-(4-(trifluoromethyl)phenyl)piperidin-4-yloxy)benzamide | 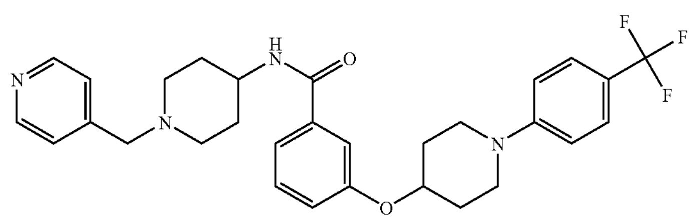 |
| 88 | N-(1-(pyridin-4-ylmethyl)piperidin-4-yl)-3-(1-(4-cyanophenyl)piperidin-4-yloxy)benzamide | 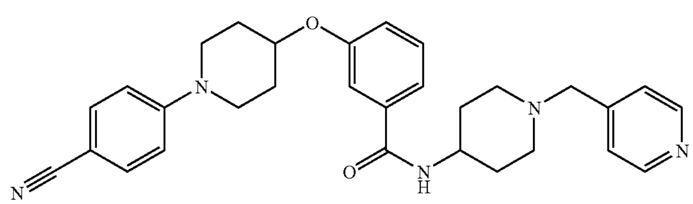 |
| 89 | N-(1-benzylpiperidin-4-yl)-3-(1-(3-cyanobenzyl)piperidin-4-yloxy)benzamide | 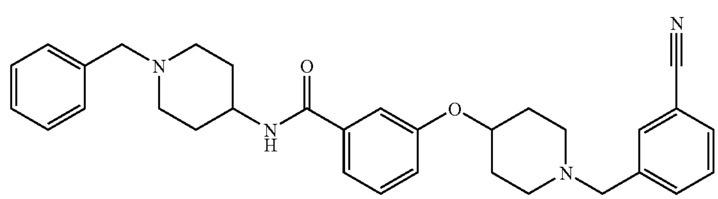 |
| 90 | tert-butyl 4-(4-(1-benzylpiperidin-4-ylcarbamoyl)-2-chlorophenoxy)piperidine-1-carboxylate | 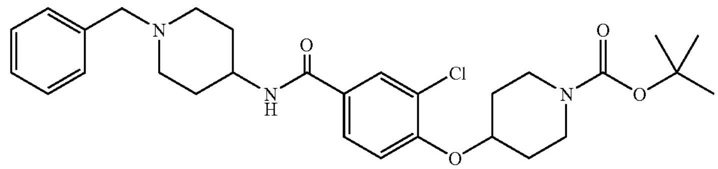 |

TABLE 1-continued

| Cpd | Name | Structure |
|---|---|---|
| 91 | N-(1-benzylpiperidin-4-yl)-3-chloro-4-(1-pivaloylpiperidin-4-yloxy)benzamide | 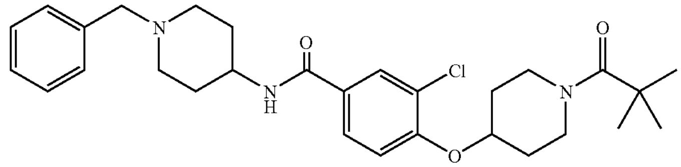 |
| 92 | tert-butyl 4-(4-(1-benzylpiperidin-4-ylcarbamoyl)-2-fluorophenoxy)piperidine-1-carboxylate | 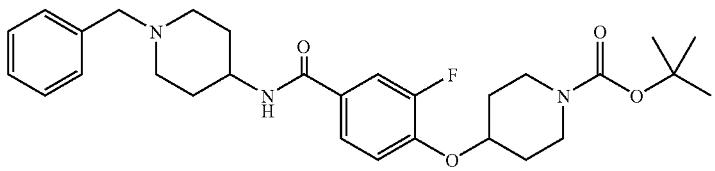 |
| 93 | N-(1-benzylpiperidin-4-yl)-3-chloro-4-(piperidin-4-yloxy)benzamide | 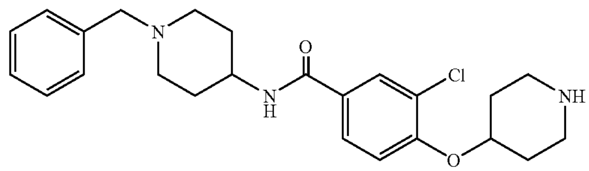 |

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in compounds of the invention can be hypervalent, e.g., an N-oxide or tetrasubstituted ammonium salt. On occasion a moiety may be defined, for example, as $(A)_a$-B—, wherein a is 0 or 1. In such instances, when a is 0 the moiety is B— and when a is 1 the moiety is A-B—.

As used herein, the term "alkyl" includes alkyl, alkenyl and alkynyl groups of a designed number of carbon atoms, desirably from 1 to about 12 carbons (i.e., inclusive of 1 and 12). The term "$C_m$-$C_n$ alkyl" means an alkyl group having from m to n carbon atoms (i.e., inclusive of m and n). The term "$C_m$-$C_n$ alkyl" means an alkyl group having from m to n carbon atoms. For example, "$C_1$-$C_6$ alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "$C_0$ alkyl"), the group is simply a single covalent bond if it is a divalent radical or is a hydrogen atom if it is a monovalent radical. For example, the moiety "—($C_0$-$C_6$ alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 12 carbons.

The term "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like.

The term "aryl" represents an aromatic carbocyclic ring system having a single ring (e.g., phenyl) which is optionally fused to other aromatic hydrocarbon rings or non-aromatic hydrocarbon rings. "Aryl" includes ring systems having multiple condensed rings and in which at least one is aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, 2,3-dihydrobenzofuranyl and 6,7,8,9-tetrahydro-5H-benzo[a]cycloheptenyl. The aryl groups herein are unsubstituted or, when specified as "optionally substituted", can unless stated otherwise be substituted in one or more substitutable positions with various groups, as described below.

The term "heteroaryl" refers to an aromatic ring system containing at least one heteroatom selected from nitrogen, oxygen and sulfur in an aromatic ring. The heteroaryl may be fused to one or more cycloalkyl or heterocycloalkyl rings. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments of the invention, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" refers to a non-aromatic ring or ring system containing at least one heteroatom that is preferably selected from nitrogen, oxygen and sulfur, wherein said heteroatom is in a non-aromatic ring. The heterocycloalkyl may be saturated (i.e., a heterocycloalkyl) or partially unsaturated (i.e., a heterocycloalkenyl). The heterocycloalkyl ring is optionally fused to other heterocycloalkyl rings and/or non-aromatic hydrocarbon rings and/or phenyl rings. In certain embodiments of the invention, the heterocycloalkyl groups have from 3 to 7 members in a single ring. In other embodiments of the invention, heterocycloalkyl groups have 5 or 6 members in a single ring. Examples of heterocycloalkyl groups include, for example, azabicyclo[2.2.2]octyl (in each case also "quinuclidinyl" or a quinuclidine derivative), azabicyclo[3.2.1]octyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butryolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as described below.

The term "cycloalkyl" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., bridged systems) to other cycloalkyl rings. Preferred cycloalkyl groups have from 3 to 7 members in a single ring. More preferred cycloalkyl groups have 5 or 6 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "electron withdrawing group" means a group that withdraws electron density from the structure to which it is attached than would a similarly-attached hydrogen atom. For example, electron withdrawing groups can be selected from the group consisting of halo, cyano, —($C_1$-$C_4$ fluoroalkyl), —O—($C_1$-$C_4$ fluoroalkyl), acyl groups (e.g., —C(O)—H, —C(O)-alkyl), carboxylate groups (e.g., carboxylic acids and esters), carboxamide groups, cyano groups, sulfonate groups (including sulfonic acid and sulfonic esters), and nitro groups.

The term "substituted," when used to modify a specified group or radical, means that one or more hydrogen atoms of the specified group or radical are each, independently of one another, replaced with the same or different substituent groups as defined below.

Substituent groups for substituting for hydrogens on saturated carbon atoms in the specified group or radical are, unless otherwise specified, —$R^{60}$, halo, —$O^-M^+$, =O, —$OR^{70}$, —$SR^{70}$, —$S^-M^+$, =S, —$NR^{80}R^{80}$, =$NR^{70}$, =N—$OR^{70}$, trihalomethyl, —$CF_3$, —CN, —OCN, —SCN, —NO, —$NO_2$, =$N_2$, —$N_3$, —$SO_2R^{70}$, —$SO_2O^-M^+$, —$SO_2OR^{70}$, —$OSO_2R^{70}$, —$OSO_2O^-M^+$, —$OSO_2OR^{70}$, —P(O)($O^-$)$_2$($M^+$)$_2$, —P(O)($OR^{70}$)$O^-M^+$, —P(O)($OR^{70}$)$_2$, —C(O)$R^{70}$, —C(S)$R^{70}$, —C(N$R^{70}$)$R^{70}$, —C(O)$O^-M^+$, C(O)$OR^{70}$, —C(S)$OR^{70}$, —C(O)N$R^{80}R^{80}$, —C(N$R^{70}$)N$R^{80}R^{80}$, —OC(O)$R^{70}$, —OC(S)$R^{70}$, —OC(O)$O^-M^+$, —OC(O)$OR^{70}$, —OC(S)$OR^{70}$, —N$R^{70}$C(O)$R^{70}$, —N$R^{70}$C(S)$R^{70}$, —N$R^{70}$CO$_2^-M^+$, —N$R^{70}$CO$_2R^{70}$, —N$R^{70}$C(S)$OR^{70}$, —N$R^{70}$C(O)N$R^{80}R^{80}$, N$R^{70}$C(N$R^{70}$)$R^{70}$ and —N$R^{70}$C(N$R^{70}$)N$R^{80}R^{80}$. Each $R^{60}$ is independently selected from the group consisting of alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —$O^-M^+$, =O, —$OR^{71}$, —$SR^{71}$, —$S^-M^+$, =S, —$NR^{81}R^{81}$, =$NR^{71}$, =N—$OR^{71}$, trihalomethyl, —$CF_3$, —CN, —OCN, —SCN, —NO, —$NO_2$, =$N_2$, —$N_3$, —$SO_2R^{71}$, —$SO_2O^-M^+$, —$SO_2OR^{71}$, —$OSO_2R^{71}$, —$OSO_2O^-M^+$, —$OSO_2OR^{71}$, —P(O)($O^-$)$_2$($M^+$)$_2$, —P(O)($OR^{71}$)$O^-M^+$, —P(O)($OR^{71}$)$_2$, —C(O)$R^{71}$, —C(S)$R^{71}$, —C(N$R^{71}$)$R^{71}$, —C(O)$O^-M^+$, —C(O)$OR^{71}$, —C(S)$OR^{71}$, —C(O)N$R^{81}R^{81}$, —C(N$R^{71}$)N$R^{81}R^{81}$, —OC(O)$R^{71}$, —OC(S)$R^{71}$, —OC(O)$O^-M^+$, —OC(O)$OR^{71}$, —OC(S)$OR^{71}$, —N$R^{71}$C(O)$R^{71}$, —N$R^{71}$C(S)$R^{71}$, —N$R^{71}$CO$_2^-M^+$, —N$R^{71}$CO$_2R^{71}$, —N$R^{71}$C(S)$OR^{71}$, —N$R^{71}$C(O)N$R^{81}R^{81}$, —N$R^{71}$C(N$R^{71}$)$R^{71}$ and —N$R^{71}$C(N$R^{71}$)N$R^{81}R^{81}$. Each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $R^{71}$ is independently hydrogen or $R^{61}$, in which $R^{61}$ is alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —$O^-M^+$, =O, —$OR^{72}$, —$SR^{72}$, $S^-M^+$, =S, —$NR^{82}R^{82}$, =$NR^{72}$, =N—$OR^{72}$, trihalomethyl, —$CF_3$, —CN, —OCN, —SCN, —NO, —$NO_2$, =$N_2$, —$N_3$, —$SO_2R^{71}$, —$SO_2O^-M^+$, —$SO_2OR^{72}$, —$OSO_2R^{72}$, —$OSO_2O^-M^+$, —$OSO_2OR^{72}$, —$P(O)(O^-)_2(M^+)_2$, —$P(O)(OR^{72})O^-M^+$, —$P(O)(OR^{72})_2$, —$C(O)R^{72}$, —$C(S)R^{72}$, —$C(NR^{72})R^{72}$, —$C(O)O^-M^+$, —$C(O)OR^{72}$, —$C(S)OR^{72}$, —$C(O)NR^{82}R^{82}$, —$C(NR^{72})NR^{82}R^{82}$, —$OC(O)R^{72}$, —$OC(S)R^{72}$, —$OC(O)O^-M^+$, —$OC(O)OR^{72}$, —$OC(S)OR^{72}$, —$NR^{72}C(O)R^{72}$, —$NR^{72}C(S)R^{72}$, —$NR^{72}CO_2^-M^+$, —$NR^{72}CO_2R^{72}$, —$NR^{72}C(S)OR^{72}$, —$NR^{72}C(O)NR^{82}R^{82}$, —$NR^{72}C(NR^{72})R^{72}$ and —$NR^{72}C(NR^{72})NR^{82}R^{82}$; and each $R^{81}$ is independently $R^{71}$ or alternatively, two $R^{81}$s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution. Each $R^{72}$ is independently hydrogen, ($C_1$-$C_6$ alkyl) or ($C_1$-$C_6$ fluoroalkyl); each $R^{82}$ is independently $R^{72}$ or alternatively, two $R^{82}$s, taken together with the nitrogen atom to which they are bonded, form a 5-, 6- or 7-membered heterocycloalkyl which may optionally include 1, 2, 3 or 4 of the same or different additional heteroatoms selected from the group consisting of O, N and S, of which N may have —H or $C_1$-$C_3$ alkyl substitution. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means e.g. that one of the counter ions for such divalent alkali earth ions can be an ionized form of a compound of the invention and the other a typical counter ion such as chloride, or two ionized compounds of the invention can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4-methyl-piperazin-1-yl and N-morpholinyl.

Substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

Substituent groups for hydrogens on nitrogen atoms in "substituted" heteroalkyl and cycloheteroalkyl groups are, unless otherwise specified, —$R^{60}$, —$O^-M^+$, —$OR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In a preferred embodiment, a group that is substituted has 1, 2, 3, or 4 substituents, 1, 2, or 3 substituents, 1 or 2 substituents, or 1 substituent.

The term "pharmaceutically acceptable salts" or "a pharmaceutically acceptable salt thereof" refer to salts prepared from pharmaceutically acceptable non-toxic acids or bases including inorganic acids and bases and organic acids and bases. If the compound used in the present invention is basic, salts may be prepared from pharmaceutically acceptable non-toxic acids. Such salts may be, for example, acid addition salts of at least one of the following acids: benzenesulfonic acid, citric acid, α-glucoheptonic acid, D-gluconic acid, glycolic acid, lactic acid, malic acid, malonic acid, mandelic acid, phosphoric acid, propanoic acid, succinic acid, sulfuric acid, tartaric acid (d, l, or dl), tosic acid (toluenesulfonic acid), valeric acid, palmitic acid, pamoic acid, sebacic acid, stearic acid, lauric acid, acetic acid, adipic acid, carbonic acid, 4-chlorobenzenesulfonic acid, ethanedisulfonic acid, ethylsuccinic acid, fumaric acid, galactaric acid (mucic acid), D-glucuronic acid, 2-oxo-glutaric acid, glycerophosphoric acid, hippuric acid, isethionic acid (ethanolsulfonic acid), lactobionic acid, maleic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, hydriodic acid, hydrobromic acid, hydrochloric acid, methanesulfonic acid, nicotinic acid, nitric acid, orotic acid, oxalic acid, picric acid, L-pyroglutamic acid, saccharine, salicylic acid, gentisic acid, and/or 4-acetamidobenzoic acid.

"Prodrug" refers to a derivative of an active compound (drug) that requires a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Other specific examples of suitable progroups and their respective promoieties will be apparent to those of skill in the art.

The compounds of the present invention can be made using procedures familiar to the person of ordinary skill in the art and as described herein. For example, compounds of structural formulae (I)-(XVI) can be prepared according to Scheme 1, below:

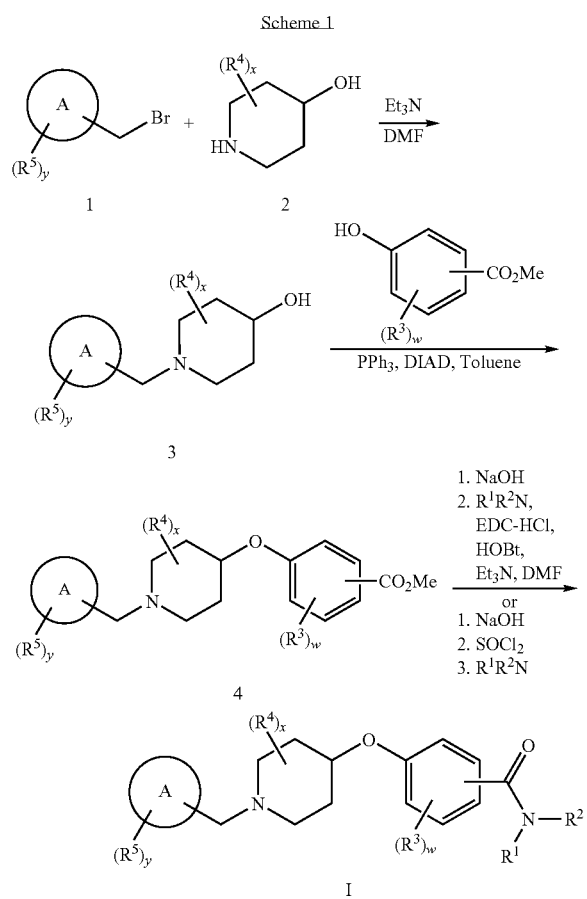

Referring to Scheme 1, bromides 1, for example, can be coupled with 4-hydroxypiperidines 2 to provide 1-substituted 4-hydroxypiperidine 3. Substituted 4-hydroxypiperidine 3 can be subjected to Mitsinobu conditions, e.g., with appropriate phenols to give coupled products 4. The ester group of 4 is saponified, for example, converted to the corresponding carboxylic acid and coupled with an appropriate amine to yield amine to give compounds of structural formula (I).

One of ordinary skill in the art can adapt the reaction sequence of Scheme 1 to fit the desired target molecule. For example, a benzyl bromide can be used as a starting material to afford compounds of structural formula (I) in which the ring system denoted by "A" is a phenyl. Similarly, a (heteroaryl)methyl bromide may be used as a starting material to afford compounds of structural formula (I) in which the ring system denoted by "A" is a heteroaryl. Alternatively, reductive amination of an aryl or heteroaryl aldehyde, for example, with the nitrogen of azacycloalkyl 2 would also afford 3. In certain situations one of ordinary skill in the art will use different reagents to effect one or more of the individual steps or to use protected versions of certain of the $R^1$, $R^2$, $R^3$, $R^4$ and $R^5$ substituents. An example of the synthesis of a compound of the present invention is provided below in Example 1.

The compounds of structural formulae (I)-(XVI) may be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like.

Another aspect of the invention is a pharmaceutical formulation comprising a pharmaceutically acceptable carrier, diluent or excipient, and compound as described above with reference to structural formulae (I)-(XVI). In one embodiment according to this aspect of the invention, the compound is as described above with reference to structural formulae (I)-(XVI), but is not N-(1-benzylpiperidin-4-yl)-3-methoxy-4-(1-(furan-2-yl)piperidin-4-yloxy)benzamide.

In the pharmaceutical compositions according to this aspect of the invention, one or more compounds of structural formulae (I)-(XVI) may be present in association with one or more pharmaceutically acceptable carriers, diluents or excipients, and, if desired, other active ingredients. The pharmaceutical compositions containing compounds of structural formulae (I)-(XVI) may be in a form suitable for oral use, for example, as tablets, troches, lozenges, aqueous or oily suspensions, dispersible powders or granules, emulsion, hard or soft capsules, or syrups or elixirs. In one embodiment according to this aspect of the invention, the compound is as described above with reference to structural formulae (I)-(XVI), but is not N-(1-benzylpiperidin-4-yl)-3-methoxy-4-(1-(furan-2-yl)piperidin-4-yloxy)benzamide.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of structural formulae (I)-(XVI) can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of structural formula (I)-(XVI) can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Compounds suitable for use in the pharmaceutical compositions according to this aspect of the invention include compounds of Table 1, above, as well as compounds of Table 2, below. These compounds can be made according to the general scheme described above, for example using a procedure similar to that described below in Example 1.

TABLE 2

| Cpd | Name | Structure |
|---|---|---|
| 1 | N-(1-benzylpiperidin-4-yl)-3-chloro-4-(1-(4-methoxybenzyl)piperidin-4-yloxy)benzamide | 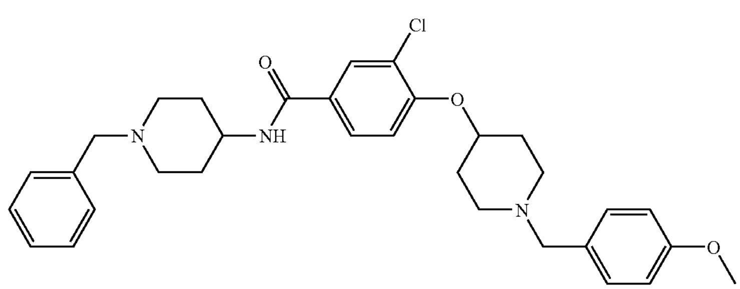 |

TABLE 2-continued

| Cpd | Name | Structure |
|---|---|---|
| 2 | N-(1-benzylpiperidin-4-yl)-4-(1-benzylpiperidin-4-yloxy)-3-methoxybenzamide | 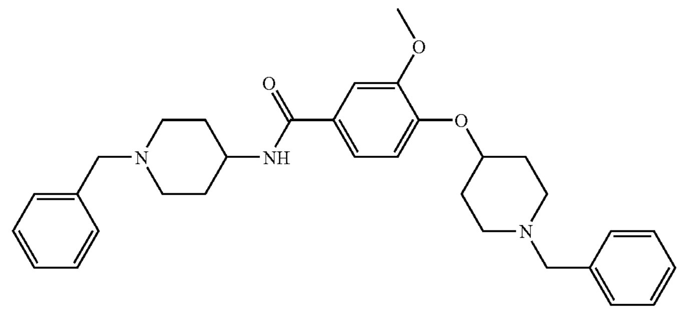 |
| 3 | N-(1-benzylpiperidin-4-yl)-4-(1-(furan-2-ylmethyl)piperidin-4-yloxy)benzamide | 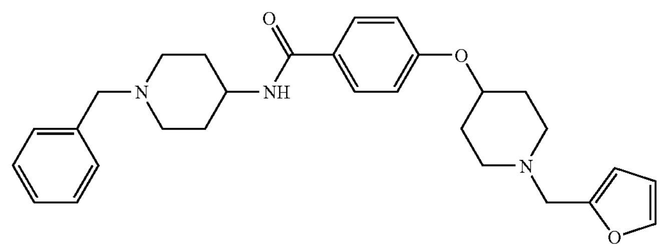 |
| 4 | N-(1-benzylpiperidin-4-yl)-4-(1-((1-methyl-1H-imidazol-5-yl)methyl)piperidin-4-yloxy)benzamide | 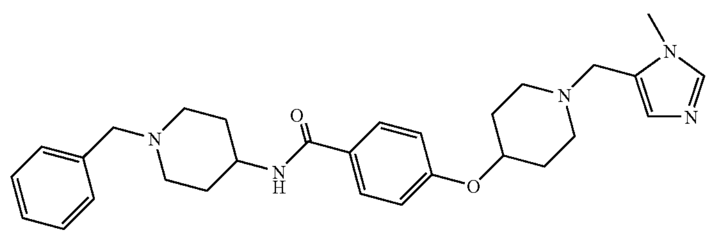 |
| 5 | N-(1-benzylpiperidin-4-yl)-3-chloro-4-(1-((1-methyl-1H-imidazol-5-yl)methyl)piperidin-4-yloxy)benzamide | 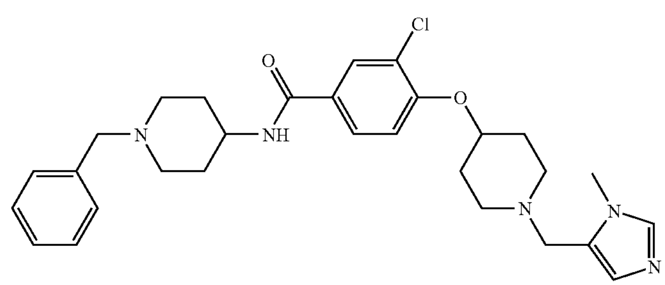 |
| 6 | N-(1-benzylpiperidin-4-yl)-3-chloro-4-(1-(pyridin-4-ylmethyl)piperidin-4-yloxy)benzamide | 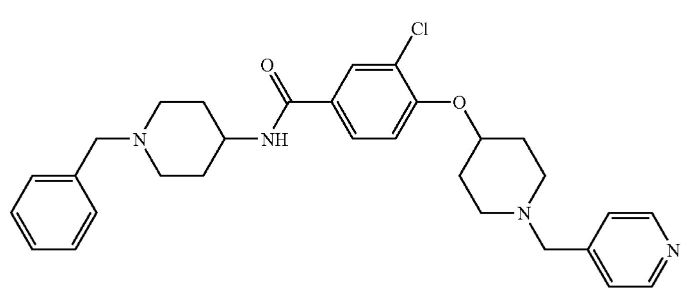 |

TABLE 2-continued

| Cpd | Name | Structure |
|---|---|---|
| 7 | N-(1-benzylpiperidin-4-yl)-3-methoxy-4-(1-(3-phenylpropyl)piperidin-4-yloxy)benzamide | 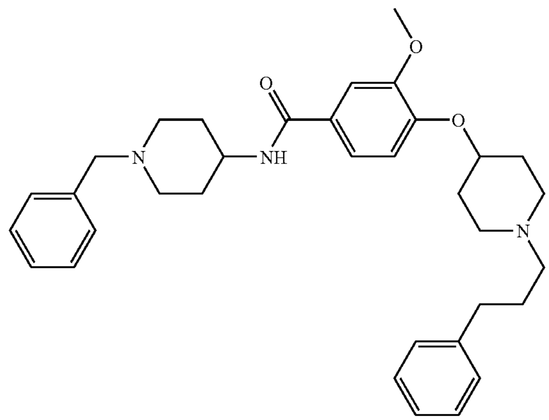 |
| 8 | N-(1-benzylpiperidin-4-yl)-3-methoxy-4-(1-(thiophen-2-yl)piperidin-4-yloxy)benzamide | 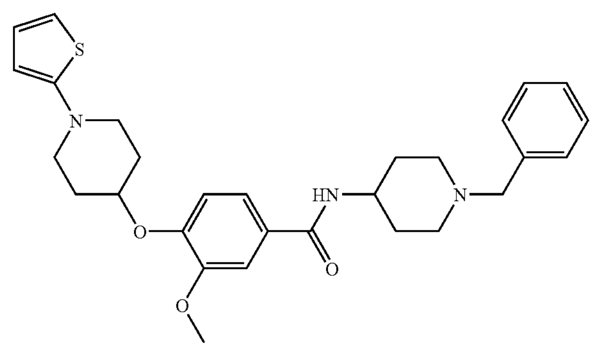 |
| 9 | N-(1-benzylpiperidin-4-yl)-3-methoxy-4-(1-(methylsulfonyl)piperidin-4-yloxy)benzamide | 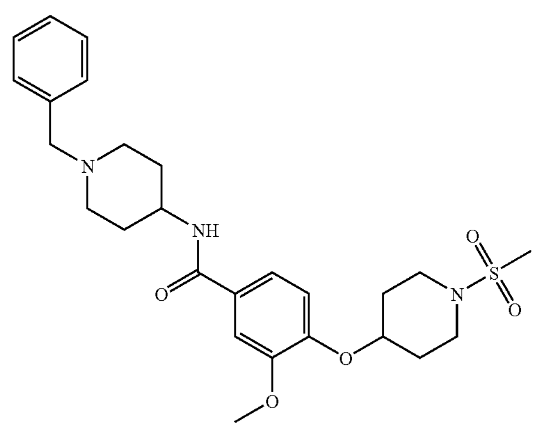 |
| 10 | N-(1-benzylpiperidin-4-yl)-3-chloro-4-(1-(thiophen-2-yl)piperidin-4-yloxy)benzamide | 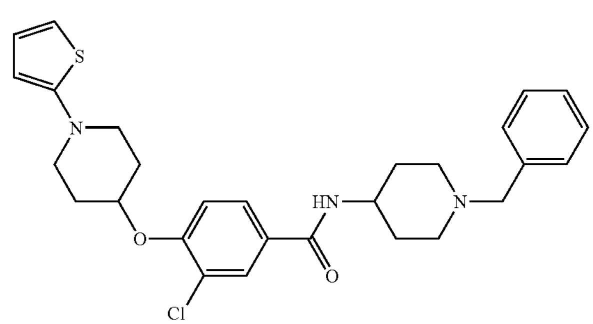 |

TABLE 2-continued

| Cpd | Name | Structure |
|---|---|---|
| 11 | N-(1-benzylpiperidin-4-yl)-3-chloro-4-(1-(furan-2-yl)piperidin-4-yloxy)benzamide | 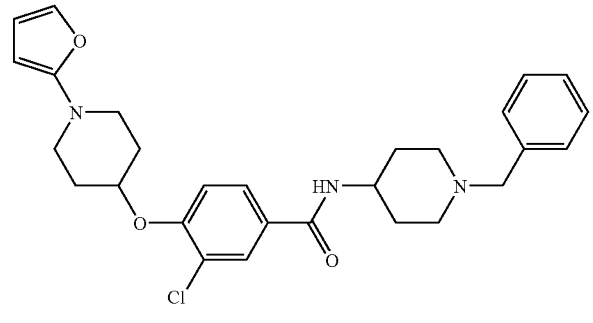 |
| 12 | N-(1-benzylpiperidin-4-yl)-3-methoxy-4-(1-(furan-2-yl)piperidin-4-yloxy)benzamide | 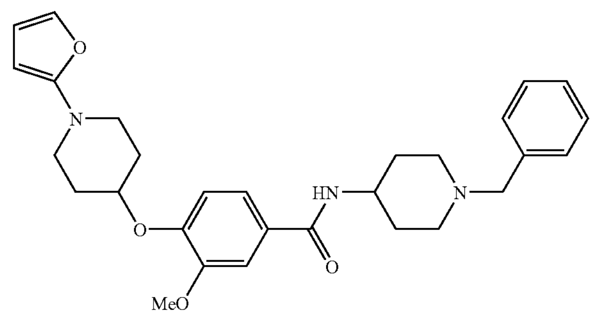 |
| 13 | N-(1-benzylpiperidin-4-yl)-3-(1-benzylpiperidin-4-yloxy)benzamide | 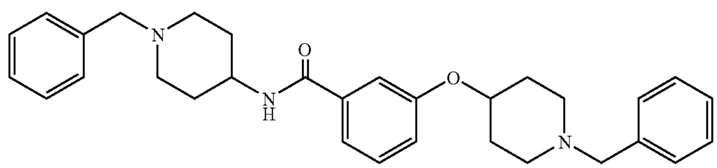 |

Another aspect of the invention relates to pharmaceutical composition comprising a compound having structural formula (XVII):

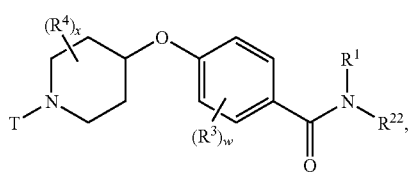

(XVII)

or a pharmaceutically acceptable salt, solvate, hydrate, or N-oxide thereof, and at least one pharmaceutically acceptable carrier, diluent or excipient, wherein $R^1$ and $R^{22}$, together with the nitrogen to which they are attached, form an optionally substituted monocyclic heterocycloalkyl; or $R^1$ is H and $R^{22}$ is selected from —($C_2$-$C_4$ alkyl)-(morpholin-4-yl) and —($C_2$-$C_4$ alkyl)-NH—C(O)O—($C_1$-$C_6$ alkyl), and all other variables are as described above with reference to structural formulae (I)-(XVI).

In one embodiment according to this aspect of the invention, $R^1$ and $R^{22}$, together with the nitrogen to which they are attached, form an optionally substituted monocyclic heterocycloalkyl. The heterocycloalkyl can be, for example, piperidine or piperazine. In certain embodiments according to this aspect of the invention, the heterocycloalkyl is piperazine substituted at its 4-position with —C(O)O—($C_1$-$C_6$ alkyl), —($C_0$-$C_4$)-Het or —($C_0$-$C_4$)—Ar. For example, the piperazine may be substituted at its 4-position with —C(O)O-tBu, -optionally-substituted pyridinylmethyl, optionally-substituted phenyl or optionally-substituted pyridinyl.

In another embodiment according to this aspect of the invention, $R^1$ is H and $R^{22}$ is selected from —($C_2$-$C_4$ alkyl)-(morpholin-4-yl) and —($C_2$-$C_4$ alkyl)-NH—C(O)O—($C_1$-$C_6$ alkyl). However, when w and x are zero, y is 1 and $R^5$ is methoxy substituted para to the benzyl methylene, $R^{22}$ is not —($C_2$-$C_4$ alkyl)-(morpholin-4-yl); and when w is 1, x and y are zero, and $R^3$ is methoxy substituted ortho to the ether oxygen, $R^{22}$ is not —($C_2$-$C_4$ alkyl)-(morpholin-4-yl). In certain embodiments of the invention, $R^{22}$ is —($C_2$-$C_4$ alkyl)-NH—C(O)O—($C_1$-$C_6$ alkyl). The $C_1$-$C_6$ alkyl can be, for example, a tert-butyl group.

The pharmaceutical compositions according to this aspect of the invention can be formulated and administered as described above with respect to the pharmaceutical compositions of structural formulae (I)-(XVI), above.

Compounds suitable for use in the pharmaceutical compositions according to this aspect of the invention include compounds of Table 3, below. These compounds can be made according to the general scheme described above, for example using a procedure similar to that described below in Example 1.

TABLE 3

| Cpd | Name | Structure |
|---|---|---|
| 94 | tert-butyl 3-(3-methoxy-4-(1-(4-(trifluoromethyl)benzyl)piperidin-4-yloxy)benzamido)propylcarbamate | 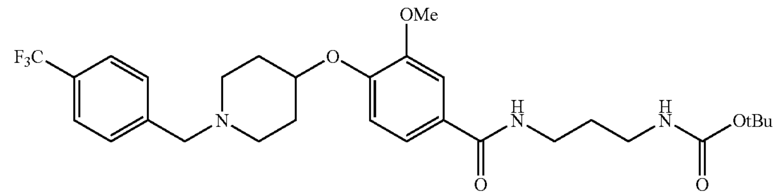 |
| 95 | tert-butyl 3-(4-(1-(4-(trifluoromethyl)benzyl)piperidin-4-yloxy)benzamido)propylcarbamate | 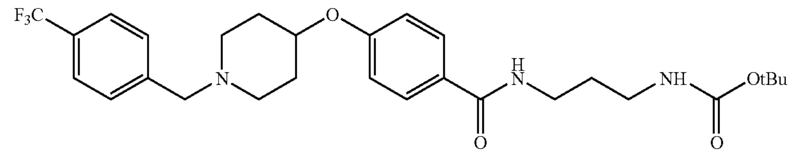 |
| 96 | tert-butyl 4-(4-(1-(4-methoxybenzyl)piperidin-4-yloxy)benzoyl)piperazine-1-carboxylate | 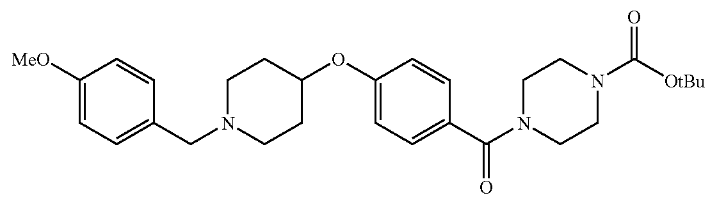 |
| 97 | tert-butyl 3-(3-chloro-4-(1-(4-methoxybenzyl)piperidin-4-yloxy)benzamido)propylcarbamate | 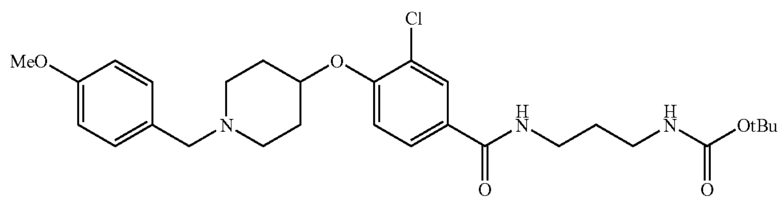 |
| 98 | 4-(1-(4-chlorobenzyl)piperidin-4-yloxy)-4-methoxy-N-(3-morpholinopropyl)benzamide | 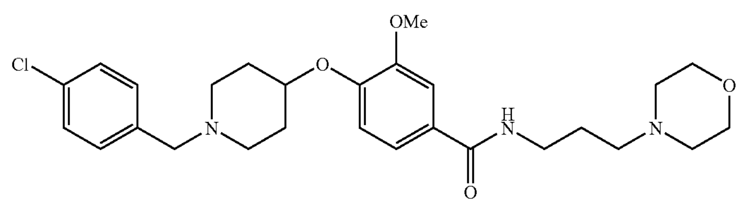 |
| 99 | tert-butyl 4-(4-(1-benzylpiperidin-4-yloxy)benzoyl)piperazine-1-carboxylate | 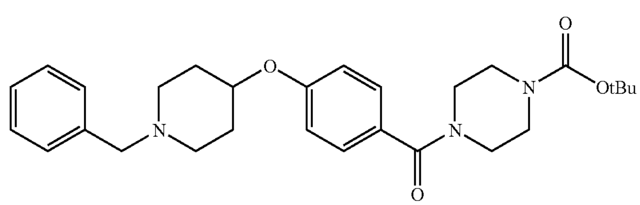 |
| 100 | 4-(1-(4-chlorobenzyl)piperidin-4-yloxy)-N-(3-morpholinopropyl)benzamide | 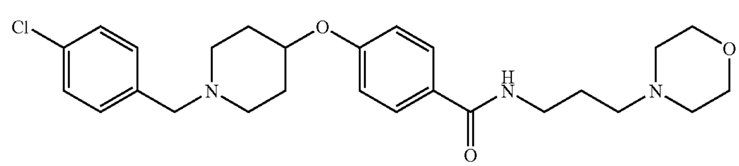 |
| 101 | 3-chloro-4-(1-(4-methoxybenzyl)piperidin-4-yloxy)-N-(3-morpholinopropyl)benzamide | 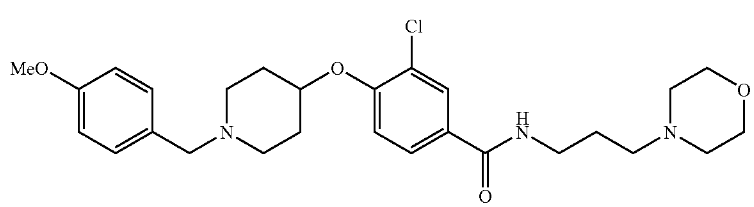 |

TABLE 3-continued

| Cpd | Name | Structure |
|---|---|---|
| 102 | tert-butyl 3-(4-(1-benzylpiperidin-4-yloxy)-3-chlorobenzamido)propylcarbamate | 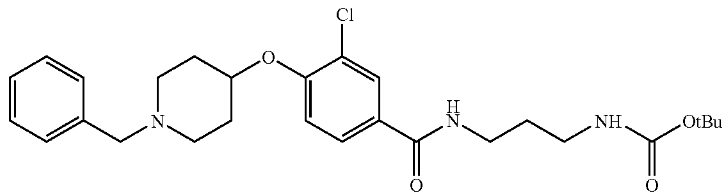 |
| 103 | (4-(1-benzylpiperidin-4-yloxy)phenyl)(4-phenylpiperazin-1-yl)methanone | 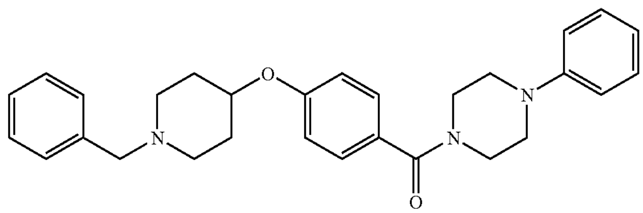 |
| 104 | 4-(1-(4-methylbenzyl)piperidin-4-yloxy)-N-(3-morpholinopropyl)benzamide | 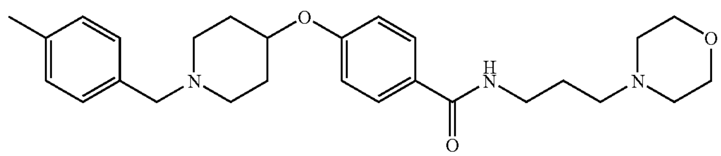 |
| 105 | (4-(1-benzylpiperidin-4-yloxy)phenyl)(4-(pyridin-2-ylmethyl)piperazin-1-yl)methanone | 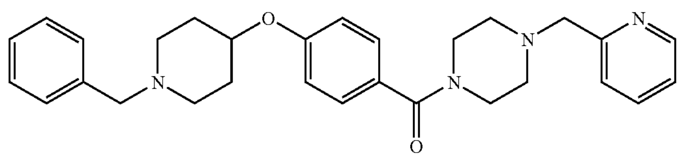 |

While not intending to be bound by theory, the inventors surmise that compounds of structural formulae (I)-(XVII) are mimics of adiponectin which act as adiponectin receptor agonists, thereby activating the AMPK pathway. Activation of the AMPK pathway has the effect of increasing glucose uptake, decreasing glycogen synthesis and increasing fatty acid oxidation, thereby reducing glycogen, intracellular triglyceride and fatty acid concentration and causing an increase in insulin sensitivity. Because they activate the AMPK pathway, compounds of structural formulae (I)-(XVII) should also inhibit the inflammatory processes which occur during the early phases of atherosclerosis. Accordingly, compounds of structural formulae (I)-(XVII) can be useful in the treatment of type II diabetes and in the treatment and prevention of atherosclerosis, cardiovascular disease, obesity and non-alcoholic fatty liver disease.

Accordingly, another aspect of the invention is a method of activating the AMPK pathway. According to this aspect of the invention, a method for activating the AMPK pathway in a cell includes contacting the cell with an effective amount of a compound, pharmaceutically acceptable salt, prodrug, solvate, hydrate, N-oxide or composition described above. Data demonstrating activation of the AMPK pathway are provided below in Example 3.

Another aspect of the invention is a method of increasing fatty acid oxidation in a cell. According to this aspect of the invention, a method of increasing fatty acid oxidation in a cell includes contacting the cell with an effective amount of a compound, pharmaceutically acceptable salt, prodrug, solvate, hydrate, N-oxide or composition described above. Data demonstrating an increase in phosphorylated acetyl Co-A carboxylase (PACC) caused by certain compounds of the present invention are provided below in Example 3. Acetyl Co-A carboxylase (ACC) catalyzes the formation of malonyl Co-A, a potent inhibitor of fatty acid oxidation; phosphorylation of ACC greatly reduces its catalytic activity, thereby reducing the concentration of malonyl Co-A and increasing the rate of fatty acid oxidation. Because compounds of the invention can increase the rate of phosphorylation of ACC, they can reduce the inhibition of fatty acid oxidation and therefore increase its overall rate.

Another aspect of the invention is a method of decreasing glycogen concentration in a cell. According to this aspect of the invention, a method of decreasing glycogen concentration in a cell includes contacting the cell with an effective amount of a compound, pharmaceutically acceptable salt, prodrug, solvate, hydrate, N-oxide or composition described above. Data demonstrating a decrease of glycogen concentration caused by certain compounds of the present invention are provided below in Example 4.

Another aspect of the invention is a method of increasing glucose uptake in a cell. According to this aspect of the invention, a method of increasing glucose uptake in a cell includes contacting the cell with an effective amount of a compound, pharmaceutically acceptable salt, prodrug, solvate, hydrate, N-oxide or composition described above. Data demonstrating increase of glucose uptake caused by certain compounds of the present invention are provided below in Example 5.

Another aspect of the invention is a method of reducing triglyceride levels in a subject. According to this aspect of the invention, a method of reducing triglyceride levels in a subject includes administering to the subject an effective amount of a compound, pharmaceutically acceptable salt, prodrug, solvate, hydrate, N-oxide or composition described above.

Another aspect of the invention is a method of increasing the insulin sensitivity of a subject. According to this aspect of the invention, a method of increasing insulin sensitivity of a subject includes administering to the subject an effective amount of a compound, pharmaceutically acceptable salt, prodrug, solvate, hydrate, N-oxide or composition described above.

Another aspect of the invention is a method of treating type II diabetes. According to this aspect of the invention, a method of treating type II diabetes in a subject in need of such treatment includes administering to the subject an effective amount of a compound, pharmaceutically acceptable salt, prodrug, solvate, hydrate, N-oxide or composition described above.

Another aspect of the invention is a method of treating or preventing atherosclerosis or cardiovascular disease. According to this aspect of the invention, a method of treating or preventing atherosclerosis or cardiovascular disease in a subject includes administering to the subject an effective amount of a compound, pharmaceutically acceptable salt, prodrug, solvate, hydrate, N-oxide or composition described above.

In another aspect, the compounds of the invention, as activators of the AMPK pathway, the invention comprises modulating the AMPK pathway (either in vitro or in vivo) by contacting a cell with a compound, pharmaceutically acceptable salt, prodrug, solvate, hydrate, N-oxide or composition described above, or administering a compound, pharmaceutically acceptable salt, prodrug, solvate, hydrate, N-oxide or composition described above to a mammal (e.g., a human) in an amount sufficient to modulate the AMPK activity and study the effects thereby induced. Such methods are useful for studying the AMPK pathway and its role in biological mechanisms and disease states both in vitro and in vivo.

The following examples are intended to further illustrate certain preferred embodiments of the invention and are not intended to limit the scope of the invention.

EXAMPLES

Example 1

Synthesis of N-(1-benzylpiperidin-4-yl)-3-chloro-4-(1-(4-methoxybenzyl)-piperidin-4-yloxy)benzamide a. 1-(4-Methoxybenzyl)piperidin-4-ol To a stirred solution of 4-hydroxypiperidine (0.97 g, 9.60 mmol) in anhydrous dimethylformamide (20 mL) at 0° C. was added 1-(bromomethyl)-4-methoxybenzene (1.93 g, 9.60 mmol) and triethylamine (2.16 g, 21.4 mmol). The reaction mixture was then warmed to room temperature and stirred overnight. After this time the mixture was concentrated under reduced pressure and the resulting residue was dissolved in ethyl acetate (40 mL), washed with water (20 mL), then brine (20 mL) and dried over sodium sulfate. The drying agent was filtered off and the filtrate concentrated under reduced pressure. The residue obtained was purified by flash chromatography (silica gel, 0-5% methanol/methylene chloride) to afford 1-(4-methoxybenzyl)piperidin-4-ol as a brown oil (1.70 g, 80%). $^1$H-NMR (CDCl$_3$, 300 MHz): δ 7.27 (d, J=7.8 Hz, 2H), 6.86 (d, J=7.8 Hz, 2H), 3.79 (s, 3H), 3.76 (m, 1H), 3.55 (s, 2H), 2.81 (m, 2H), 2.29 (m, 2H), 1.96 (m, 2H), 1.64 (m, 3H); MS (ESI): 222.1 (M+H).

b. Methyl 3-chloro-4-(1-(4-methoxybenzyl)piperidin-4-yloxy)benzoate

To a stirred solution of 1-(4-methoxybenzyl)piperidin-4-ol (0.33 g, 1.49 mmol) in toluene (10 mL) at room temperature was added triphenylphosphine (0.44 g, 1.67 mmol) and methyl 3-chloro-4-hydroxybenzoate (0.42 g, 2.25 mmol). The reaction was stirred at room temperature for 5 min. After this time, diisopropyl azodicarboxylate (0.33 g, 1.67 mmol) was added dropwise and the reaction was stirred at room temperature overnight. The mixture was concentrated under reduced pressure and the resulting residue was purified by flash chromatography (silica gel, methylene chloride/methanol/30% ammonium hydroxide=25/1/0.05) to afford methyl 3-chloro-4-(1-(4-methoxybenzyl)piperidin-4-yloxy)benzoate as a white solid (0.05 g, 10%). MS (ESI): 390.1 (M+1).

c. 3-Chloro-4-(1-(4-methoxybenzyl)piperidin-4-yloxy)benzoic Acid

To a stirred solution of methyl 3-chloro-4-(1-(4-methoxybenzyl)piperidin-4-yloxy)benzoate (0.04 g, 0.10 mmol) in methanol (0.5 mL) at room temperature was added 2 N sodium hydroxide (0.25 mL, 0.50 mmol) and the resulting mixture was stirred at room temperature overnight. After this time 2 N hydrochloric acid (0.3 mL, 0.60 mmol) was added and the mixture was concentrated under reduced pressure to afford 3-chloro-4-(1-(4-methoxybenzyl)piperidin-4-yloxy)benzoic acid as a crude solid which was used without further purification. MS (ESI): 376.1 (M+1).

d. N-(1-Benzylpiperidin-4-yl)-3-chloro-4-(1-(4-methoxybenzyl)-piperidin-4-yloxy)-benzamide To a stirred mixture of 3-chloro-4-(1-(4-methoxybenzyl) piperidin-4-yloxy)benzoic acid in anhydrous dimethylformamide (0.5 mL) was added triethylamine (0.03 g, 0.30 mmol), 1-hydroxybenzotriazole hydrate (0.02 g, 0.15 mmol), 1-(3-dimethylaminopropyl)-3-ethylcarbodiimide hydrochloride (0.03 g, 0.15 mmol) and 1-benzylpiperidin-4-amine (0.03 mg, 0.15 mmol). The mixture was stirred at room temperature overnight and then concentrated under reduced pressure. The residue obtained was purified by flash chromatography (silica gel, methylene chloride/methanol/30% ammonium hydroxide=15/1/0.05) to afford N-(1-benzylpiperidin-4-yl)-3-chloro-4-(1-(4-methoxybenzyl)-piperidin-4-yloxy)-benzamide as a white solid (0.01 g, 18%). $^1$H-NMR (CDCl$_3$, 300 MHz): δ 7.76 (m, 1H), 7.60 (m, 1H), 7.30 (m, 7H), 6.94 (m, 1H), 6.87 (m, 2H), 5.83 (d, J=7.2 Hz, 1H), 4.52 (m, 1H), 3.97 (m, 1H), 3.80 (s, 3H), 3.54 (s, 4H), 2.86 (m, 4H), 2.11 (m, 8H), 1.58 (m, 4H); LCMS: >98%; MS (ESI): 548.2 (M+1), 546.2 (M−1).

Example 2

$^1$H-NMR and Mass Spectral Data

The following compounds were prepared using methods analogous to those described in Example 1 and in Scheme 1.

Compound 14: N-(1-benzylpiperidin-4-yl)-4-(1-benzylpiperidin-4-yloxy)-3-chlorobenzamide. $^1$H NMR (CDCl$_3$, 300 MHz) δ 7.74 (s, 1H), 7.59 (d, J=7.8 Hz, 1H), 7.32 (m, 10H), 6.94 (d, J=7.8 Hz, 1H), 5.83 (d, J=7.1 Hz, 1H), 4.47 (m, 1H), 3.96 (m, 1H), 3.58 (s, 4H), 2.85 (m, 2H), 2.71 (m, 2H), 2.38 (m, 2H), 2.19 (m, 2H), 1.96 (m, 6H), 1.57 (m, 2H) ppm; MS (ES) 518.2 (M+H).

Compound 15: N-(1-benzylpiperidin-4-yl)-3-chloro-4-(1-((2,3-dihydrobenzo[b][1,4]dioxin-6-yl)methyl)piperidin-4-yloxy)benzamide. $^1$H NMR (CDCl$_3$, 300 MHz) δ 7.74 (s, 1H), 7.60 (d, J=7.8 Hz, 1H), 7.28 (m, 4H), 6.93 (d, J=7.8 Hz, 1H), 6.82 (m, 4H), 5.82 (d, J=6.9 Hz, 1H), 4.47 (m, 1H), 4.24 (s, 4H), 3.96 (m, 1H), 3.52 (s, 2H), 3.44 (s, 2H), 2.84 (m, 2H), 2.70 (m, 2H), 2.37 (m, 2H), 2.17 (m, 2H), 1.95 (m, 6H), 1.61 (m, 2H) ppm; MS (ES) 576.1 (M+H).

Compound 16: N-(1-benzylpiperidin-4-yl)-4-(1-(4-tert-butylbenzyl)piperidin-4-yloxy)-3-chlorobenzamide. $^1$H NMR (CDCl$_3$, 300 MHz) δ 7.74 (s, 1H), 7.60 (d, J=7.8 Hz, 1H), 7.30 (m, 9H), 6.93 (d, J=7.8 Hz, 1H), 5.84 (d, J=7.2 Hz, 1H), 4.48 (m, 1H), 3.96 (m, 1H), 3.52 (s, 4H), 2.86 (m, 2H), 2.72 (m, 2H), 2.40 (m, 2H), 2.18 (m, 2H), 1.94 (m, 6H), 1.57 (m, 2H), 1.32 (s, 9H) ppm; MS (ES) 574.3 (M+H).

Compound 17: N-(1-benzylpiperidin-4-yl)-3-chloro-4-(1-(4-(trifluoromethyl)phenyl)piperidin-4-yloxy)benzamide. $^1$H NMR (CDCl$_3$, 300 MHz) δ 7.76 (m, 1H), 7.67 (m, 1H), 7.48 (m, 2H), 7.33 (m, 5H), 6.97 (m, 3H), 5.84 (d, J=8.1 Hz, 1H), 4.68 (m, 1H), 3.97 (m, 1H), 3.56 (m, 4H), 3.35 (m, 2H), 2.87 (m, 2H), 2.19 (m, 2H), 2.03 (m, 6H), 1.59 (m, 2H) ppm; MS (ES) 572.2 (M+H).

Compound 18: N-(1-benzylpiperidin-4-yl)-3-chloro-4-(1-(4-(trifluoromethyl)benzoyl)piperidin-4-yloxy)benzamide. $^1$H NMR (CDCl$_3$, 300 MHz) δ 7.77 (m, 1H), 7.65 (m, 3H), 7.53 (m, 2H), 7.30 (m, 5H), 6.95 (d, J=9.0 Hz, 1H), 5.92 (d, J=7.2 Hz, 1H), 4.76 (m, 1H), 4.04 (m, 2H), 3.70 (m, 2H), 3.51 (s, 2H), 3.42 (m, 1H), 2.85 (m, 2H), 2.16 (m, 2H), 2.07-1.78 (m, 6H), 1.54 (m, 2H) ppm; MS (ES) 600.8 (M+H).

Compound 19: N-(1-benzylpiperidin-4-yl)-3-chloro-4-(1-(4-fluorobenzyl)piperidin-4-yloxy)benzamide. $^1$H NMR (CDCl$_3$, 300 MHz) δ 7.74 (m, 1H), 7.60 (m, 1H), 7.31 (m, 7H), 6.98 (m, 3H), 5.85 (d, J=8.1 Hz, 1H), 4.48 (m, 1H), 3.97 (m, 1H), 3.50 (m, 4H), 2.85 (m, 2H), 2.68 (m, 2H), 2.36 (m, 2H), 2.16 (m, 2H), 1.97 (m, 6H), 1.54 (m, 2H) ppm; MS (ES) 536.2 (M+H).

Compound 20: N-(1-benzylpiperidin-4-yl)-3-fluoro-4-(1-(4-tert-butylbenzyl)piperidin-4-yloxy)benzamide. $^1$H NMR (CDCl$_3$, 300 MHz) δ 7.46 (m, 2H), 7.31 (m, 9H), 6.97 (m, 1H), 5.84 (d, J=8.1 Hz, 1H), 4.39 (m, 1H), 3.98 (m, 1H), 3.51 (m, 4H), 2.85 (m, 2H), 2.74 (m, 2H), 2.31 (m, 2H), 2.17 (m, 2H), 2.07-1.69 (m, 6H), 1.54 (m, 2H), 1.31 (s, 9H) ppm; MS (ES) 558.6 (M+H).

Compound 21: N-(1-benzylpiperidin-4-yl)-3-fluoro-4-(1-(1-phenylethyl)piperidin-4-yloxy)benzamide. $^1$H NMR (CDCl$_3$, 300 MHz) δ 7.44 (m, 2H), 7.31 (m, 10H), 6.94 (m, 3H), 5.82 (d, J=7.8 Hz, 1H), 4.32 (m, 1H), 3.97 (m, 1H), 3.51 (s, 2H), 3.46 (m, 1H), 2.85 (m, 2H), 2.72 (m, 2H), 2.21 (m, 4H), 2.04-1.63 (m, 6H), 1.54 (m, 2H), 1.38 (d, J=6.6 Hz, 3H) ppm; MS (ES) 516.5 (M+H).

Compound 22: N-(1-benzylpiperidin-4-yl)-3-chloro-4-(1-(4-fluorobenzoyl)piperidin-4-yloxy)benzamide. $^1$H NMR (CDCl$_3$, 300 MHz) δ 7.77 (m, 1H), 7.63 (m, 1H), 7.38 (m, 2H), 7.31 (m, 5H), 7.10 (m, 2H), 6.95 (m, 1H), 5.93 (d, J=7.8 Hz, 1H), 4.74 (m, 1H), 3.97 (m, 1H), 3.72 (m, 2H), 3.52 (m, 4H), 2.86 (m, 2H), 2.17 (m, 2H), 1.97 (m, 8H), 1.55 (m, 2H) ppm; MS (ES) 550.8 (M+H).

Compound 23: N-(1-benzylpiperidin-4-yl)-3-fluoro-4-(1-(4-(trifluoromethyl)phenyl)piperidin-4-yloxy)benzamide. $^1$H NMR (CDCl$_3$, 300 MHz) δ 7.49 (m, 4H), 7.31 (m, 5H), 7.02 (m, 1H), 6.94 (d, J=8.4 Hz, 2H), 5.84 (d, J=8.1 Hz, 1H), 4.60 (m, 1H), 3.97 (m, 1H), 3.60 (m, 2H), 3.52 (s, 2H), 3.26 (m, 2H), 2.85 (m, 2H), 2.18 (m, 2H), 2.06 (m, 6H), 1.54 (m, 2H) ppm; MS (ES) 556.6 (M+H).

Compound 24: N-(1-benzylpiperidin-4-yl)-3-chloro-4-(1-(2-(trifluoromethyl)benzyl)piperidin-4-yloxy)benzamide. $^1$H NMR (CDCl$_3$, 300 MHz) δ 7.99 (m, 1H), 7.75 (m, 1H), 7.61 (m, 2H), 7.52 (m, 1H), 7.30 (m, 4H), 7.27 (m, 2H), 6.95 (d, J=9.0 Hz, 1H), 5.83 (d, J=7.5 Hz, 1H), 4.48 (m, 1H), 3.97 (m, 1H), 3.69 (m, 2H), 3.53 (s, 2H), 2.86 (m, 2H), 2.76 (m, 2H), 2.39 (m, 2H), 2.19 (m, 2H), 1.90 (m, 6H), 1.59 (m, 2H) ppm; MS (ES) 586.1 (M+H).

Compound 25: 3-fluoro-N-(1-phenylpiperidin-4-yl)-4-(1-(4-(trifluoromethyl)phenyl)piperidin-4-yloxy)benzamide. $^1$H NMR (CDCl$_3$, 300 MHz) δ 7.52 (m, 4H), 7.25 (m, 2H), 6.97 (m, 6H), 5.88 (d, J=6.3 Hz, 1H), 4.60 (m, 1H), 4.13 (m, 1H), 3.65 (m, 4H), 3.26 (m, 2H), 2.93 (m, 2H), 2.02 (m, 6H), 1.64 (m, 2H) ppm; MS (ES) 542.1 (M+H).

Compound 26: tert-butyl 4-(3-fluoro-4-(1-(4-(trifluoromethyl)phenyl)piperidin-4-yloxy)benzamido)piperidine-1-carboxylate. $^1$H NMR (CDCl$_3$, 300 MHz) δ 7.54 (m, 4H), 7.03 (m, 1H), 6.93 (m, 2H), 6.11 (d, J=7.5 Hz, 1H), 4.60 (m, 1H), 4.42 (m, 2H), 4.20 (m, 1H), 3.60 (m, 2H), 3.26 (m, 2H), 2.96 (m, 2H), 2.08 (m, 2H), 1.98 (m, 4H), 1.40 (m, 2H), 1.46 (s, 9H) ppm; MS (ES) 566.1 (M+H).

Compound 27: 3-fluoro-N-(1-(4-fluorobenzyl)piperidin-4-yl)-4-(1-(4-(trifluoromethyl)phenyl)piperidin-4-yloxy)benzamide. $^1$H NMR (CDCl$_3$, 300 MHz) δ 7.49 (m, 4H), 7.28 (m, 2H), 6.99 (m, 5H), 5.86 (d, J=6.9 Hz, 1H), 4.59 (m, 1H), 3.98 (m, 1H), 3.60 (m, 2H), 3.48 (s, 2H), 3.27 (m, 2H), 2.84 (m, 2H), 2.17 (m, 2H), 2.04 (m, 6H), 1.54 (m, 2H) ppm; MS (ES) 574.6 (M+H).

Compound 28: 3-fluoro-N-(1-(pyridin-4-ylmethyl)piperidin-4-yl)-4-(1-(4-(trifluoromethyl)phenyl)piperidin-4-yloxy)benzamide. $^1$H NMR (CDCl$_3$, 300 MHz) δ 8.55 (m, 2H), 7.50 (m, 4H), 7.28 (m, 2H), 7.03 (m, 1H), 6.95 (d, J=8.7 Hz, 1H), 5.86 (d, J=7.5 Hz, 1H), 4.60 (m, 1H), 3.99 (m, 1H), 3.60 (m, 2H), 3.52 (s, 2H), 3.26 (m, 2H), 2.83 (m, 2H), 2.21 (m, 2H), 2.03 (m, 6H), 1.54 (m, 2H) ppm; MS (ES) 557.5 (M+H).

Compound 29: 3-fluoro-N-(1-(pyridin-3-ylmethyl)piperidin-4-yl)-4-(1-(4-(trifluoromethyl)phenyl)piperidin-4-yloxy)benzamide. $^1$H NMR (CDCl$_3$, 300 MHz) δ 8.54 (m, 2H), 7.65 (m, 1H), 7.49 (m, 4H), 7.24 (m, 1H), 7.04 (m, 1H), 6.94 (m, 1H), 5.85 (d, J=7.5 Hz, 1H), 4.60 (m, 1H), 3.98 (m, 1H), 3.60 (m, 2H), 3.53 (s, 2H), 3.26 (m, 2H), 2.84 (m, 2H), 2.20 (m, 2H), 2.02 (m, 6H), 1.57 (m, 2H) ppm; MS (ES) 557.5 (M+H).

Compound 30: 3-fluoro-N-(1-pivaloylpiperidin-4-yl)-4-(1-(4-(trifluoromethyl)phenyl)piperidin-4-yloxy)benzamide. $^1$H NMR (CDCl$_3$, 300 MHz) δ 7.51 (m, 4H), 7.02 (m, 1H), 6.94 (d, J=8.7 Hz, 2H), 6.16 (d, J=7.5 Hz, 1H), 4.60 (m, 1H), 4.42 (m, 2H), 4.20 (m, 1H), 3.60 (m, 2H), 3.26 (m, 2H), 2.96 (m, 2H), 2.08 (m, 2H), 1.98 (m, 4H), 1.40 (m, 2H), 1.28 (s, 9H) ppm; MS (ES) 550.5 (M+H).

Compound 31: 3-fluoro-N-(1-(4-fluorobenzoyl)piperidin-4-yl)-4-(1-(4-(trifluoromethyl)phenyl)piperidin-4-yloxy)benzamide. $^1$H NMR (CDCl$_3$, 300 MHz) δ 7.56-7.38 (m, 6H), 7.06 (m, 3H), 6.95 (d, J=8.9 Hz, 1H), 5.98 (d, J=8.1 Hz, 1H), 4.61 (m, 1H), 4.23 (m, 1H), 3.60 (m, 2H), 3.28 (m, 2H), 3.10 (m, 2H), 2.18-1.82 (m, 6H), 1.48 (m, 4H) ppm; MS (ES) 588.5 (M+H).

Compound 32: 3-fluoro-N-(1-(pyridin-2-ylmethyl)piperidin-4-yl)-4-(1-(4-(trifluoromethyl)phenyl)piperidin-4-yloxy)benzamide. $^1$H NMR (CDCl$_3$, 300 MHz) δ 8.57 (m, 1H), 7.65 (m, 1H), 7.49 (m, 4H), 7.38 (d, J=7.8 Hz, 1H), 7.17 (m, 1H), 7.05 (m, 1H), 6.95 (d, J=8.7 Hz, 1H), 5.83 (d, J=7.8 Hz, 1H), 4.60 (m, 1H), 3.99 (m, 1H), 3.67 (s, 2H), 3.59 (m, 2H), 3.26 (m, 2H), 2.88 (m, 2H), 2.28 (m, 2H), 2.04 (m, 6H), 1.62 (m, 2H) ppm; MS (ES) 557.7 (M+H).

Compound 33: methyl 4-((4-(3-fluoro-4-(1-(4-(trifluoromethyl)phenyl)piperidin-4-yloxy)benzamido)piperidin-1-yl)methyl)benzoate. $^1$H NMR (CDCl$_3$, 300 MHz) δ 7.99 (m, 2H), 7.44 (m, 6H), 7.03 (m, 1H), 6.94 (d, J=8.7 Hz, 1H), 5.84 (d, J=7.2 Hz, 1H), 4.60 (m, 1H), 3.98 (m, 1H), 3.90 (s, 2H), 3.61 (m, 2H), 3.56 (s, 3H), 3.26 (m, 2H), 2.84 (m, 2H), 2.20 (m, 2H), 2.03 (m, 6H), 1.58 (m, 2H) ppm; MS (ES) 614.6 (M+H).

Compound 34: 3-fluoro-N-(1-(isopropylsulfonyl)piperidin-4-yl)-4-(1-(4-(trifluoromethyl)phenyl)piperidin-4-yloxy)benzamide. $^1$H NMR (CDCl$_3$, 300 MHz) δ 7.50 (m, 4H), 7.02 (m, 1H), 6.94 (d, J=8.1 Hz, 1H), 6.14 (m, 1H), 4.61 (m, 1H), 4.13 (m, 1H), 3.90 (m, 2H), 3.60 (m, 2H), 3.24 (m, 3H), 3.03 (m, 2H), 2.13-1.91 (m, 6H), 1.62 (m, 2H), 1.35 (m, 6H) ppm; MS (ES) 572.5 (M+H).

Compound 35: 4-((4-(3-fluoro-4-(1-(4-(trifluoromethyl)phenyl)piperidin-4-yloxy)benzamido)piperidin-1-yl)methyl)benzoic acid. $^1$H NMR (CD$_3$OD, 300 MHz) δ 8.02 (m, 2H), 7.62 (m, 2H), 7.48 (m, 4H), 7.24 (m, 1H), 7.06 (m, 2H), 4.72 (m, 1H), 4.01 (m, 3H), 3.65 (m, 2H), 3.28 (m, 2H), 2.74 (m, 2H), 2.12-1.73 (m, 10H) ppm; MS (ES) 600.6 (M+H).

Compound 36: 4-(1-(4-tert-butylbenzyl)piperidin-4-yloxy)-3-fluoro-N-(1-phenylpiperidin-4-yl)benzamide. $^1$H NMR (CD$_3$OD, 300 MHz) δ 7.63 (m, 2H), 7.45 (m, 2H), 7.35 (m, 2H), 7.22 (m, 3H), 6.99 (m, 2H), 6.83 (m, 1H), 4.66 (m, 1H), 3.98 (m, 3H), 3.70 (m, 2H), 3.10 (m, 2H), 2.82 (m, 4H), 2.03 (m, 6H), 1.79 (m, 2H), 1.31 (s, 9H) ppm; MS (ES) 544.6 (M+H).

Compound 37: N-(1-benzylpiperidin-4-yl)-3-fluoro-4-(1-(pyridin-4-ylmethyl)piperidin-4-yloxy)benzamide. $^1$H NMR (CDCl$_3$, 300 MHz) δ 8.54 (m, 2H), 7.46 (m, 4H), 7.28 (m, 7H), 6.98 (m, 1H), 5.86 (d, J=8.1 Hz, 1H), 4.43 (m, 1H), 3.97 (m, 1H), 3.53 (s, 4H), 2.86 (m, 2H), 2.71 (m, 2H), 2.34 (m, 2H), 2.19 (m, 2H), 2.06-1.68 (m, 6H), 1.55 (m, 2H) ppm; MS (ES) 503.1 (M+H).

Compound 38: N-(1-benzylpiperidin-4-yl)-3-fluoro-4-(1-(pyridin-3-ylmethyl)piperidin-4-yloxy)benzamide. $^1$H NMR (CDCl$_3$, 300 MHz) δ 8.52 (m, 2H), 7.67 (m, 1H), 7.46 (m, 2H), 7.31 (m, 6H), 6.97 (m, 1H), 5.84 (d, J=7.2 Hz, 1H), 4.42 (m, 1H), 3.97 (m, 1H), 3.53 (m, 4H), 2.86 (m, 2H), 2.71 (m, 2H), 2.34 (m, 2H), 2.18 (m, 2H), 2.08-1.68 (m, 6H), 1.55 (m, 2H) ppm; MS (ES) 503.5 (M+H).

Compound 39: N-(1-benzylpiperidin-4-yl)-3-fluoro-4-(1-(pyridin-2-ylmethyl)piperidin-4-yloxy)benzamide. $^1$H NMR (CDCl$_3$, 300 MHz) δ 8.57 (m, 2H), 7.58 (m, 2H), 7.31 (m, 6H), 7.19 (m, 1H), 6.98 (m, 1H), 5.83 (d, J=7.2 Hz, 1H), 4.41 (m, 1H), 3.96 (m, 1H), 3.53 (m, 4H), 2.86 (m, 2H), 2.70 (m, 2H), 2.33 (m, 2H), 2.18 (m, 2H), 2.07-1.69 (m, 6H), 1.55 (m, 2H) ppm; MS (ES) 503.5 (M+H).

Compound 40: 3-fluoro-N-(1-isonicotinoylpiperidin-4-yl)-4-(1-(4-(trifluoromethyl)phenyl)piperidin-4-yloxy)benzamide. $^1$H NMR (CDCl$_3$, 300 MHz) δ 8.70 (m, 2H), 7.49 (m, 4H), 7.26 (m, 2H), 7.03 (m, 1H), 6.94 (d, J=8.7 Hz, 1H), 5.99 (d, J=7.8 Hz, 1H), 4.72 (m, 1H), 4.61 (m, 1H), 4.22 (m, 1H), 3.60 (m, 3H), 3.26 (m, 3H), 2.99 (m, 1H), 2.21-1.91 (m, 6H), 1.56 (m, 2H) ppm; MS (ES) 571.4 (M+H).

Compound 41: N-(1-benzylpiperidin-4-yl)-4-(1-(4-cyanobenzyl)piperidin-4-yloxy)-3-fluorobenzamide. $^1$H NMR (CDCl$_3$, 300 MHz) δ 7.63 (m, 3H), 7.47 (m, 5H), 7.31 (m, 3H), 6.98 (m, 1H), 5.82 (d, J=7.8 Hz, 1H), 4.43 (m, 1H), 3.99 (m, 1H), 3.54 (m, 4H), 2.85 (m, 2H), 2.70 (m, 2H), 2.34 (m, 2H), 2.18 (m, 2H), 2.08-1.72 (m, 6H), 1.56 (m, 2H) ppm; MS (ES) 527.5 (M+H).

Compound 42: N-(1-benzylpiperidin-4-yl)-3-fluoro-4-(1-(4-methylbenzyl)piperidin-4-yloxy)benzamide. $^1$H NMR (CDCl$_3$, 300 MHz) δ 7.46 (m, 2H), 7.29 (m, 7H), 7.13 (m, 2H), 6.97 (m, 1H), 5.846 (d, J=7.5 Hz, 1H), 4.41 (m, 1H), 3.97 (m, 1H), 3.53 (s, 4H), 2.87 (m, 2H), 2.75 (m, 2H), 2.34 (m, 5H), 2.19 (m, 2H), 2.08-1.82 (m, 6H), 1.57 (m, 2H) ppm; MS (ES) 516.6 (M+H).

Compound 43: N-(1-(4-cyanobenzyl)piperidin-4-yl)-3-fluoro-4-(1-(4-(trifluoromethyl)phenyl)piperidin-4-yloxy)benzamide. $^1$H NMR (CDCl$_3$, 300 MHz) δ 7.61 (m, 2H), 7.49 (m, 6H), 6.98 (m, 3H), 5.84 (m, 1H), 4.61 (m, 1H), 3.99 (m, 1H), 3.570 (m, 4H), 3.26 (m, 2H), 2.82 (m, 2H), 2.22 (m, 2H), 2.02 (m, 6H), 1.58 (m, 2H) ppm; MS (ES) 581.5 (M+H).

Compound 44: 4-(1-(4-cyanophenyl)piperidin-4-yloxy)-3-fluoro-N-(1-(pyridin-4-ylmethyl)piperidin-4-yl)benzamide. $^1$H NMR (CDCl$_3$, 300 MHz) δ 8.54 (m, 3H), 7.7 (m, 3H), 7.03 (m, 1H), 6.88 (m, 2H), 5.84 (d, J=7.5 Hz, 1H), 4.63 (m, 1H), 3.98 (m, 1H), 3.63 (m, 2H), 3.52 (s, 2H), 3.357 (m, 2H), 2.83 (m, 2H), 2.21 (m, 2H), 2.01 (m, 6H), 1.58 (m, 2H) ppm; MS (ES) 514.6 (M+H).

Compound 45: N-(1-(4-cyanobenzyl)piperidin-4-yl)-4-(1-(4-cyanophenyl)piperidin-4-yloxy)-3-fluorobenzamide. $^1$H NMR (CDCl$_3$, 300 MHz) δ 7.64 (m, 4H), 7.47 (m, 4H), 7.01 (m, 1H), 6.87 (m, 2H), 5.95 (d, J=7.8 Hz, 1H), 4.63 (m, 1H), 3.99 (m, 1H), 3.64 (m, 2H), 3.56 (s, 2H), 3.34 (m, 2H), 2.82 (m, 2H), 2.20 (m, 2H), 2.03 (m, 6H), 1.55 (m, 2H) ppm; MS (ES) 538.7 (M+H).

Compound 46: N-(1-benzylpiperidin-4-yl)-3-(1-(4-(trifluoromethyl)phenyl)piperidin-4-yloxy)benzamide. $^1$H NMR (CDCl$_3$, 300 MHz): δ 7.47 (d, 1H), 7.37-7.23 (m, 4H), 7.05 (d, 2H), 6.94 (d, 2H), 6.04 (d, 1H), 4.95 (m, 1H), 4.00 (m, 1H), 3.60 (m, 2H), 3.56 (s, 2H), 3.24 (m, 2H), 2.91 (m, 2H), 2.21 (m, 2H), 1.90-2.12 (m, 6H), 1.65 (m, 2H); LCMS (m/z): 538 (MH$^+$).

Compound 47: N-(1-benzylpiperidin-4-yl)-2-chloro-4-(1-(4-(trifluoromethyl)phenyl)piperidin-4-yloxy)benzamide. $^1$H NMR (CDCl$_3$, 300 MHz): δ 7.60 (d, 1H), 7.67 (d, 2H), 7.25-7.48 (m, 6H), 6.94 (d, 2H), 6.86 (d, 1H), 6.25 (d, 1H), 4.55 (m, 1H), 4.05 (m, 1H), 3.52-3.60 (m, 2H), 3.58 (s, 2H), 3.28 (m, 2H), 2.86 (m, 2H), 1.90-2.27 (m, 8H), 1.64 (m, 2H); LCMS (m/z): 573 (MH$^+$).

Compound 48: N-(1-benzylpiperidin-4-yl)-3-(1-(4-cyanophenyl)piperidin-4-yloxy)benzamide. $^1$H NMR (CDCl$_3$, 300 MHz): δ 748-7.25 (m, 10H), 7.02 (m, 1H), 6.86 (d, 2H), 6.32 (d, 1H), 4.61 (m, 1H), 4.05 (m, 1H), 3.73 (s, 2H), 3.31 (m, 2H), 3.05 (m, 2H), 2.40 (m, 2H), 2.04 (m, 4H), 1.87 (m, 4H); LCMS (m/z): 495 (MH$^+$).

Compound 49: N-(1-benzylpiperidin-4-yl)-2-chloro-4-(1-(4-cyanophenyl)piperidin-4-yloxy)benzamide. $^1$H NMR (CDCl$_3$, 300 MHz): δ 7.63 (d, 2H), 7.47 (d, 2H), 6.80-7.56 (m, 7H), 6.94 (d, 1H), 6.50 (d, 1H), 4.59 (m, 1H), 4.18 (m, 1H), 4.11 (d, 2H), 3.51 (m, 2H), 3.40 (m, 2H), 3.12 (m, 2H), 2.80 (m, 2H), 2.42 (m, 2H), 2.20 (m, 4H), 2.01 (m, 2H); LCMS (m/z): 530 (MH$^+$).

Compound 50: N-(1-benzylpiperidin-4-yl)-3-(1-(4-cyanobenzyl)piperidin-4-yloxy)benzamide. $^1$H NMR (CDCl$_3$, 300 MHz): δ 7.58 (m, 2H), 7.42 (m, 2H), 7.23-7.33 (m, 8H), 7.0 (m, 1H), 6.16 (d, 1H), 4.40 (m, 1H), 4.05 (m, 1H), 3.58 (s, 2H), 3.55 (s, 2H), 2.91 (m, 2H), 2.11-2.39 (m, 4H), 1.52-2.0 (m, 8H); LCMS (m/z): 509 (MH$^+$).

Compound 51: N-(1-benzylpiperidin-4-yl)-2-chloro-4-(1-(4-cyanobenzyl)piperidin-4-yloxy)benzamide. $^1$H NMR (CDCl$_3$, 300 MHz): δ 7.63 (d, 1H), 7.58 (m, 2H), 7.32-7.25 (m, 5H), 6.87 (d, 1H), 6.80 (m, 1H), 6.31 (d, 1H), 4.35 (m, 1H), 4.01 (m, 1H), 3.57 (s, 2H), 3.55 (s, 2H), 2.89 (m, 2H), 2.58 (m, 2H), 2.30 (m, 4H), 2.00 (m, 4H), 1.81 (m, 2H), 1.67 (m, 2H); LCMS (m/z): 544 (MH$^+$).

Compound 52: N-(1-benzylpiperidin-4-yl)-3-(1-(4-(trifluoromethyl)benzyl)piperidin-4-yloxy)benzamide. $^1$H NMR (CDCl$_3$, 300 MHz): δ 7.76 (d, 2H), δ 7.45 (d, 2H), δ 7.38-7.26 (m, 8H), δ 7.02 (d, 1H), δ 6.21 (d, 1H), δ 4.40 (m, 1H), δ 4.05 (m, 1H), δ 3.66 (s, 2H), δ 3.58 (s, 2H), δ 3.0 (m, 2H), δ 2.70 (m, 2H), δ 2.30 (m, 4H), δ 1.85 (m, 4H), δ 1.61 (m, 2H); LCMS (m/z): 552 (MH$^+$).

Compound 53: N-(1-benzylpiperidin-4-yl)-3-(1-(pyridin-4-yl)piperidin-4-yloxy)benzamide. $^1$H NMR (CDCl$_3$, 300 MHz): δ 8.21 (d, 2H), δ 7.24-7.39 (m, 8H), δ 7.02 (d, 1H), δ 6.67 (d, 2H), δ 6.28 (d, 1H), δ 4.63 (m, 1H), δ 4.05 (m, 1H), δ 3.66 (m, 2H), δ 3.54 (s, 2H), δ 3.35 (m, 2H), δ 2.91 (m, 2H), δ 2.22 (m, 2H), δ 1.95 (m, 4H), δ 1.61 (m, 2H), δ 1.22 (m, 2H); LCMS (m/z): 471 (MH$^+$).

Compound 54: N-(1-Benzylpiperidin-4-yl)-3-chloro-4-[1-(4-trifluoromethoxybenzyl)piperidin-4-yloxy]benzamide. $^1$H NMR (DMSO-d$_6$, 300 MHz): δ 8.16 (d, J=7.8 Hz, 1H), 7.89 (d, J=2.1 Hz, 1H), 7.74 (d, J=8.4 Hz, 1H), 7.41 (d, J=8.4 Hz, 2H), 7.28 (m, 6H), 4.62 (br s, 2H), 3.73 (br s, 2H), 3.51 (s, 2H), 3.45 (s, 2H), 2.79 (d, J=11.7 Hz, 2H), 2.61 (br s, 2H), 2.31 (t, J=7.8 Hz, 2H), 1.95 (m, 4H), 1.72 (m, 4H), 1.55 (m, 2H); LCMS (m/z): 602 (MH$^+$).

Compound 55: N-(1-Benzylpiperidin-4-yl)-3-fluoro-4-[1-(4-trifluoromethylbenzyl)piperidin-4-yloxy]benzamide. $^1$H NMR (DMSO-d$_6$, 300 MHz): δ 8.12 (d, J=7.8 Hz, 1H), 7.65 (m, 3H), 7.52 (d, J=8.7 Hz, 2H), 7.28 (m, 5H), 4.53 (br s, 2H), 3.73 (br s, 1H), 3.58 (s, 2H), 3.44 (s, 2H), 2.79 (d, J=10.5 Hz, 2H), 2.65 (br s, 2H), 2.28 (t, J=8.4 Hz, 2H), 1.99 (t, J=9.9 Hz, 4H), 1.72 (m, 4H), 1.55 (m, 2H); LCMS (m/z): 570 (MH$^+$).

Compound 56: N-(1-Benzylpiperidin-4-yl)-3-chloro-4-[1-(4-trifluoromethylbenzyl)piperidin-4-yloxy]benzamide. $^1$H NMR (DMSO-d$_6$, 300 MHz): δ 8.17 (d, J=7.2 Hz, 1H), 7.89 (d, J=1.2 Hz, 1H), 7.75 (d, J=8.4 Hz, 1H), 7.66 (d, J=7.8 Hz, 2H), 7.52 (d, J=8.1 Hz, 2H), 7.28 (m, 5H), 4.63 (br s, 2H), 3.71 (br s, 1H), 3.58 (s, 2H), 3.44 (s, 2H), 2.79 (d, J=11.4 Hz, 2H), 2.62 (br s, 2H), 2.32 (t, J=8.1 Hz, 2H), 1.98 (m, 4H), 1.72 (m, 4H), 1.55 (m, 2H); LCMS (m/z): 586 (MH$^+$).

Compound 57: N-(1-Benzylpiperidin-4-yl)-3-fluoro-4-[1-(4-trifluoromethoxybenzyl)piperidin-4-yloxy]benzamide. $^1$H NMR (DMSO-d$_6$, 300 MHz): δ 8.11 (d, J=7.5 Hz, 1H), 7.64 (m, 2H), 7.42 (d, J=8.4 Hz, 1H), 7.28 (m, 7H), 4.52 (br s, 1H), 3.71 (br s, 1H), 3.51 (s, 2H), 3.45 (s, 2H), 2.79 (d, J=10.5 Hz, 2H), 2.64 (br s, 2H), 2.26 (t, J=9.3 Hz, 2H), 1.97 (m, 4H), 1.72 (m, 4H), 1.54 (m, 2H); LCMS (m/z): 586 (MH$^+$).

Compound 58: N-(1-Methylpiperidin-4-yl)-3-chloro-4-[1-(4-trifluoromethylbenzyl)piperidin-4-yloxy]benzamide. $^1$H NMR (DMSO-d$_6$, 300 MHz): δ 8.16 (d, J=7.8 Hz, 1H), 7.91 (s, 1H), 7.75 (d, J=9.0 Hz, 1H), 7.66 (d, J=7.8 Hz, 2H), 7.53 (d, J=7.8 Hz, 2H), 7.24 (d, J=8.4 Hz, 1H), 4.63 (br s, 1H), 3.68 (br s, 1H), 3.58 (s, 2H), 2.76 (d, J=11.7 Hz, 2H), 2.62 (br s, 2H), 2.33 (t, J=8.7 Hz, 2H), 1.92 (m, 4H), 1.73 (m, 4H), 1.55 (m, 2H); LCMS (m/z): 510 (MH$^+$).

Compound 59: N-(1-Benzylpiperidin-4-yl)-3-fluoro-4-[1-(3-trifluoromethylbenzyl)piperidin-4-yloxy]benzamide. $^1$H NMR (DMSO-d$_6$, 300 MHz): δ 8.12 (d, J=7.5 Hz, 1H), 7.59 (m, 7H), 7.28 (m, 4H), 4.53 (d, J=4.2 Hz, 2H), 3.71 (br s, 1H), 3.58 (s, 2H), 3.44 (s, 2H), 2.79 (d, J=10.5 Hz, 2H), 2.63 (br s, 2H), 2.28 (t, J=9.3 Hz, 2H), 2.01 (m, 4H), 1.72 (m, 4H), 1.54 (m, 2H); LCMS (m/z): 570 (MH$^+$).

Compound 60: N-(1-Benzylpiperidin-4-yl)-3-chloro-4-[1-(3-trifluoromethylbenzyl)piperidin-4-yloxy]benzamide. $^1$H NMR (DMSO-d$_6$, 300 MHz): δ 8.17 (d, J=7.8 Hz, 1H), 7.90 (d, J=1.8 Hz, 1H), 7.75 (dd, J=1.8 and 8.5 Hz, 1H), 7.58 (m, 5H), 7.28 (m, 5H), 4.62 (br s, 1H), 3.71 (br s, 1H), 3.58 (s, 2H), 3.44 (s, 2H), 2.79 (d, J=11.4 Hz, 2H), 2.62 (br s, 2H), 2.33 (t, J=8.7 Hz, 2H), 1.98 (m, 4H), 1.71 (m, 4H), 1.56 (m, 2H); LCMS (m/z): 586 (MH$^+$).

Compound 61: N-(1-Benzylpiperidin-4-yl)-3-fluoro-4-[1-(4-fluorobenzyl)piperidin-4-yloxy]benzamide. $^1$H NMR (DMSO-d$_6$, 300 MHz): δ 8.11 (d, J=7.8 Hz, 1H), 7.64 (m, 3H), 7.21 (m, 7H), 7.11 (t, J=8.7 Hz, 2H), 4.51 (br s, 1H), 3.72 (br s, 1H), 3.46 (s, 2H), 3.45 (s, 2H), 2.80 (d, J=11.4 Hz, 2H), 2.62 (br s, 2H), 2.24 (t, J=9.3 Hz, 2H), 1.97 (m, 4H), 1.71 (m, 4H), 1.56 (m, 2H); LCMS (m/z): 520 (MH$^+$).

Compound 62: N-(1-Benzylpiperidin-4-yl)-3,5-dichloro-4-[1-(3-trifluoromethylbenzyl)piperidin-4-yloxy]benzamide. $^1$H NMR (DMSO-d$_6$, 300 MHz): δ 8.36 (d, J=7.5 Hz, 1H), 7.91 (s, 2H), 7.58 (m, 4H), 7.28 (m, 4H), 4.31 (br s, 1H), 3.70 (br s, 1H), 3.57 (s, 2H), 3.45 (s, 2H), 2.77 (t, J=12.6 Hz, 4H), 2.15 (t, J=9.9 Hz, 2H), 1.89 (m, 8H), 1.55 (m, 3H); LCMS (m/z): 620 (MH$^+$).

Compound 63: N-(1-Benzylpiperidin-4-yl)-4-[1-(4-trifluoromethoxybenzyl)piperidin-4-yloxy]benzamide. $^1$H NMR (DMSO-d$_6$, 300 MHz): δ 8.02 (d, J=7.5 Hz, 1H), 7.75 (d, J=8.1 Hz, 2H), 7.41 (d, J=8.1 Hz, 2H), 7.28 (m, 6H), 6.95 (d, J=8.7 Hz, 2H), 4.46 (br s, 1H), 3.71 (br s, 1H), 3.50 (s, 2H), 3.44 (s, 2H), 2.79 (d, J=11.4 Hz, 2H), 2.64 (m, 2H), 2.25 (t, J=9.3 Hz, 2H), 1.61 (m, 6H); LCMS (m/z): 568 (MH$^+$).

Compound 64: N-(1-Benzylpiperidin-4-yl)-3-fluoro-4-[1-(4-chlorobenzyl)piperidin-4-yloxy]benzamide. $^1$H NMR (DMSO-d$_6$, 300 MHz): δ 8.12 (d, J=7.5 Hz, 1H), 7.64 (m, 2H), 7.37-7.21 (m, 9H), 4.51 (br s, 1H), 3.71 (br s, 1H), 3.47 (s, 2H), 3.44 (s, 2H), 2.79 (d, J=10.8 Hz, 2H), 2.62 (m, 2H), 2.25 (t, J=10.5 Hz, 2H), 1.95 (m, 4H), 1.71 (m, 4H), 1.55 (t, J=11.5 Hz, 2H); LCMS (m/z): 536 (MH$^+$).

Compound 65: N-(1-Benzylpiperidin-4-yl)-3-chloro-4-[1-(4-chlorobenzyl)piperidin-4-yloxy]benzamide. $^1$H NMR (DMSO-d$_6$, 300 MHz): δ 8.17 (d, J=7.5 Hz, 1H), 7.90 (d, J=2.4 Hz, 1H), 7.74 (dd, J=2.1 and 8.5 Hz, 1H), 7.28 (m, 9H), 4.61 (br s, 1H), 3.71 (br s, 2H), 3.47 (s, 2H), 3.45 (s, 2H), 2.80 (d, J=11.1 Hz, 2H), 2.60 (m, 2H), 2.29 (t, J=9.0 Hz, 2H), 1.95 (m, 4 H), 1.72 (m, 4H), 1.55 (m, 2H); LCMS (m/z): 552 (MH$^+$).

Compound 66: N-[1-(4-Fluorobenzyl)piperidin-4-yl]-3-chloro-4-[1-(4-chlorobenzyl)piperidin-4-yloxy]benzamide. $^1$H NMR (DMSO-d$_6$, 300 MHz): δ 8.17 (d, J=7.5 Hz, 1H), 8.11 (s, 1H), 7.89 (d, J=2.1 Hz, 1H), 7.74 (dd, J=2.1 and 8.5 Hz, 1H), 7.32 (m, 5H), 7.23 (d, J=8.7 Hz, 1H), 7.12 (t, J=8.7 Hz, 2H), 4.61 (br s, 1H), 3.70 (br s, 1H), 3.47 (s, 2H), 3.44 (s, 2H), 2.79 (d, J=11.7 Hz, 2H), 2.60 (m, 2H), 2.29 (t, J=8.1 Hz, 2H), 1.97 (m, 4H), 1.72 (m, 4H), 1.55 (m, 2H); LCMS (m/z): 570 (MH$^+$).

Compound 67: N-(1-Benzylpiperidin-4-yl)-3-chloro-4-[1-(4-cyanobenzyl)piperidin-4-yloxy]benzamide. $^1$H NMR (DMSO-d$_6$, 300 MHz): δ 8.18 (d, J=7.8 Hz, 1H), 7.90 (d, J=2.4 Hz, 1H), 7.76 (m, 3H), 7.51 (d, J=8.1 Hz, 2H), 7.28 (m, 5H), 4.63 (br s, 1H), 3.70 (br s, 1H), 3.58 (s, 2H), 3.45 (s, 2H), 2.80 (d, J=11.4 Hz, 2H), 2.61 (m, 2H), 2.32 (t, J=8.1 Hz, 2H), 1.95 (m, 4H), 1.72 (m, 4H), 1.55 (m, 2H); LCMS (m/z): 543 (MH$^+$).

Compound 68: N-[1-(4-Fluorobenzyl)piperidin-4-yl]-3-chloro-4-[1-(4-methylbenzyl)piperidin-4-yloxy]benzamide (as the formate salt). $^1$H NMR (DMSO-d$_6$, 300 MHz): δ 8.41 (d, J=7.5 Hz, 1H), 7.92 (d, J=1.8 Hz, 1H), 7.77 (d, J=9.0 Hz, 1H), 7.53 (m, 2H), 7.41-7.28 (m, 7H), 4.29 (m, 4H), 3.34 (m, 5H), 3.06 (m, 4H), 2.33 (s, 3H), 2.06 (s, 4H), 1.99 (m, 1H), 1.74 (m, 3H); LCMS (m/z): 550 (MH$^+$).

Compound 69: N-(1-Benzylpiperidin-4-yl)-3-fluoro-4-[1-(3,4-difluorobenzyl)piperidin-4-yloxy]benzamide. $^1$H NMR (DMSO-d$_6$, 300 MHz): δ 8.12 (d, J=7.5 Hz, 1H), 7.64 (m, 2H), 7.28 (m, 7H), 7.13 (m, 1H), 4.52 (br s, 1H), 3.71 (br s, 1H), 3.47 (s, 2H), 3.44 (s, 2H), 2.80 (d, J=11.4 Hz, 2H), 2.62 (m, 2H), 2.26 (t, J=8.7 Hz, 2H), 1.95 (m, 4H), 1.68 (m, 6H); LCMS (m/z): 538 (MH$^+$).

Compound 70: N-[1-(4-Chlorobenzyl)piperidin-4-yl]-3-fluoro-4-[1-(4-cyanobenzyl)piperidin-4-yloxy]benzamide. $^1$H NMR (DMSO-d$_6$, 300 MHz): δ 8.11 (d, J=7.8 Hz, 1H), 7.77 (d, J=8.4 Hz, 2H), 7.64 (m, 2H), 7.50 (d, J=8.1 Hz, 2H), 7.31 (m, 5H), 4.53 (br s, 1H), 3.70 (br s, 1H), 3.57 (s, 2H), 3.44 (s, 2H), 2.78 (d, J=11.7 Hz, 2H), 2.63 (m, 2H), 2.28 (t, J=8.7 Hz, 2H), 1.96 (m, 4H), 1.72 (m, 4H), 1.56 (m, 2H); LCMS (m/z): 561 (MH$^+$).

Compound 71: N-[1-(4-Chlorobenzyl)piperidin-4-yl]-3-fluoro-4-[1-(3,4-difluorobenzyl)piperidin-4-yloxy]benzamide. ¹H NMR (DMSO-d₆, 300 MHz): δ 8.11 (d, J=7.8 Hz, 1H), 7.64 (m, 2H), 7.34 (m, 7H), 7.14 (m, 1H), 4.52 (br s, 1H), 3.70 (br s, 1H), 3.47 (s, 2H), 3.44 (s, 2H), 2.78 (d, J=12.0 Hz, 2H), 2.63 (m, 2H), 2.26 (t, J=10.2 Hz, 2H), 1.97 (m, 4H), 1.72 (m, 4H), 1.55 (m, 2H); LCMS (m/z): 572 (MH⁺).

Compound 72: N-[1-(4-Chlorobenzyl)piperidin-4-yl]-3-fluoro-4-[1-(4-chlorobenzyl)piperidin-4-yloxy]benzamide. ¹H NMR (DMSO-d₆, 300 MHz): δ 8.13 (d, J=7.5 Hz, 1H), 7.64 (m, 2H), 7.34 (m, 9H), 4.52 (br s, 1H), 3.71 (br s, 1H), 3.47 (s, 2H), 3.44 (s, 2H), 2.77 (d, J=11.4 Hz, 2H), 2.63 (m, 2H), 2.24 (t, J=9.0 Hz, 2H), 1.96 (m, 4H), 1.72 (m, 4H), 1.55 (m, 2H); LCMS (m/z): 570 (MH⁺).

Compound 73: N-[1-(4-Chlorobenzyl)piperidin-4-yl]-3-fluoro-4-[1-(4-methylbenzyl)piperidin-4-yloxy]benzamide. ¹H NMR (DMSO-d₆, 300 MHz): δ 8.12 (d, J=7.5 Hz, 1H), 7.63 (t, J=11.9 Hz, 2H), 7.32 (m, 5H), 7.12 (m, 4H), 4.50 (br s, 1H), 3.73 (br s, 1H), 3.44 (s, 2H), 3.42 (s, 2H), 2.77 (d, J=11.4 Hz, 2H), 2.61 (m, 2H), 2.26 (s, 3H), 2.22 (t, J=12.6 Hz, 2H), 1.96 (m, 4H), 1.65 (m, 6H); LCMS (m/z): 550 (MH⁺).

Compound 74: N-(1-Benzylpiperidin-4-yl)-3-chloro-4-[1-(3,4-difluorobenzyl)piperidin-4-yloxy]benzamide. ¹H NMR (DMSO-d₆, 300 MHz): δ 8.17 (d, J=7.5 Hz, 1H), 7.90 (d, J=2.1 Hz, 1H), 7.75 (d, J=8.4 Hz, 1H), 7.28 (m, 8H), 7.14 (m, 1H), 4.62 (br s, 1H), 3.70 (br s, 1H), 3.48 (s, 2H), 3.45 (s, 2H), 2.80 (d, J=11.4 Hz, 2H), 2.60 (m, 2H), 2.30 (t, J=8.7 Hz, 2H), 1.95 (m, 4H), 1.71 (m, 4H), 1.56 (m, 2H); LCMS (m/z): 554 (MH⁺).

Compound 75: N-(1-Benzylpiperidin-4-yl)-3,5-dichloro-4-[1-(4-chlorobenzyl)piperidin-4-yloxy]benzamide. ¹H NMR (DMSO-d₆, 300 MHz): δ 8.36 (d, J=7.8 Hz, 1H), 7.91 (s, 2H), 7.28 (m, 8H), 7.14 (m, 1H), 4.30 (br s, 1H), 3.70 (br s, 1H), 3.45 (s, 4H), 2.77 (m, 4H), 2.10 (t, J=10.5 Hz, 2H), 2.00 (t, J=10.5 Hz, 2H), 1.88 (m, 2H), 1.77 (m, 4H); LCMS (m/z): 586 (MH⁺).

Compound 76: N-(1-Benzylpiperidin-4-yl)-3,5-dichloro-4-[1-(3,4-difluorobenzyl)piperidin-4-yloxy]benzamide. ¹H NMR (DMSO-d₆, 300 MHz): δ 8.36 (d, J=7.8 Hz, 1H), 7.91 (s, 2H), 7.28 (m, 6H), 7.13 (m, 1H), 4.30 (m, 1H), 3.70 (m, 1H), 3.45 (s, 4H), 2.77 (m, 4H), 2.12 (t, J=9.6 Hz, 2H), 2.00 (t, J=11.1 Hz, 2H), 1.81 (m, 8H), 1.55 (m, 3H); LCMS (m/z): 588 (MH⁺).

Compound 77: N-(1-Benzylpiperidin-4-yl)-3,5-dichloro-4-[1-(4-cyanobenzyl)piperidin-4-yloxy]benzamide (as the formate salt). ¹H NMR (DMSO-d₆, 300 MHz): δ 8.36 (d, J=7.2 Hz, 1H), 7.76 (d, J=8.1 Hz, 2H), 7.49 (d, J=8.1 Hz, 2H), 7.28 (m, 5H), 4.31 (m, 1H), 3.70 (m, 1H), 3.56 (s, 2H), 3.45 (s, 2H), 2.77 (t, J=11.1 Hz, 4H), 2.15 (t, J=11.4 Hz, 2H), 1.99 (t, J=9.9 Hz, 2H), 1.81 (m, 5H), 1.55 (m, 3H); LCMS (m/z): 577 (MH⁺).

Compound 78: N-(1-t-Butoxycarbonylpiperidin-4-yl)-4-[1-(4-cyanobenzyl)piperidin-4-yloxy]benzamide. ¹H NMR (CDCl₃, 300 MHz): δ 7.67 (d, J=8.7 Hz, 2H), 7.59 (d, J=8.4 Hz, 2H), 7.45 (d, J=7.8 Hz, 2H), 7.25 (m, 1H), 6.89 (d, J=8.7 Hz, 2H), 5.53 (d, J=7.8 Hz, 1H), 4.40 (br s, 1H), 4.09 (m, 3H), 3.56 (s, 2H), 2.90 (t, J=10.5 Hz, 2H), 2.69 (m, 2H), 2.34 (m, 2H), 2.01 (m, 4H), 1.85 (m, 3H), 1.46 (s, 9H); LCMS (m/z): 519 (MH⁺).

Compound 79: N-(Piperidin-4-yl)-4-[1-(4-cyanobenzyl)piperidin-4-yloxy]benzamide hydrochloride. ¹H NMR (DMSO-d₆, 300 MHz): δ 8.83 (s, 3H), 8.33 (d, J=6.9 Hz, 1H), 7.88 (m, 5H), 7.03 (m, 2H), 4.84 (s, 1H), 4.43 (m, 2H), 3.38 (m, 1H), 3.28 (d, J=11.7 Hz, 3H), 3.18 (s, 2H), 2.99 9 m, 2H), 2.21 (d, J=11.1 Hz, 2H), 2.00 (m, 4H), 1.77 (m, 4H); LCMS (m/z): 419 (MH⁺).

Compound 80: N-[1-(4-Chlorobenzyl)piperidin-4-yl]-3-fluoro-4-[1-(3,4-dichlorobenzyl)piperidin-4-yloxy]benzamide. ¹H NMR (DMSO-d₆, 300 MHz): δ 8.11 (d, J=7.5 Hz, 1H), 7.64 (m, 2H), 7.54 (s, 1H), 7.31 (m, 5H), 4.51 (m, 1H), 3.72 (br s, 2H), 3.49 (s, 2H), 3.44 (s, 2H), 2.77 (d, J=12 Hz, 4H), 2.63 (m, 3H), 2.27 (t, J=8.7 Hz, 2H), 2.00 (m, 4H), 1.72 (m, 4H), 1.55 (m, 2H); LCMS (m/z): 604 (MH⁺).

Compound 81: N-[1-(4-Chlorobenzyl)piperidin-4-yl]-3-fluoro-4-[1-(4-cyanophenyl)piperidin-4-yloxy]benzamide (as the formate salt). ¹H NMR (DMSO-d₆, 300 MHz): δ 8.15 (d, J=7.5 Hz, 1H), 7.66 (t, J=9.3 Hz, 2H), 7.55 (d, J=8.7 Hz, 2H), 7.34 (m, 5H), 7.03 (d, J=9.0 Hz, 2H), 4.77 (m, 2H), 3.69 (m, 4H), 3.44 (s, 2H), 2.78 (d, J=11.1 Hz, 2H), 2.00 (m, 4H), 2.00 (m, 4H), 1.72 (m, 4H), 1.55 (m, 2H); LCMS (m/z): 547 (MH⁺).

Compound 82: N-(1-Benzylpiperidin-4-yl)-3-fluoro-4-[1-(3,4-dichlorobenzyl)piperidin-4-yloxy]benzamide. ¹H NMR (DMSO-d₆, 300 MHz): δ 8.12 (d, J=7.5 Hz, 1H), 7.64 (m, 2H), 7.53 (m, 5H), 7.27 (m, 6H), 4.53 (s, 1H), 3.72 (s, 1H), 3.44 (s, 2H), 2.79 (d, J=11.4 Hz, 2H), 2.61 (m, 2H), 2.16 (t, J=8.7 Hz, 1H), 2.02 (m, 4H), 1.69 (m, 3H), 1.38 (m, 3H); LCMS (m/z): 570 (MH⁺).

Compound 83: N-[1-(4-Pyridinylmethyl)piperidin-4-yl]-4-[1-(4-cyanobenzyl)piperidin-4-yloxy]benzamide (as the formate salt). ¹H NMR (DMSO-d₆, 300 MHz): δ 8.50 (d, J=4.8 Hz, 2H), 8.11 (s, 1H), 8.06 (d, J=7.2 Hz, 1H), 7.77 (d, J=8.4 Hz, 3H), 7.51 (d, J=7.8 Hz, 2H), 6.96 (d, J=8.7 Hz, 2H), 6.50 (s, 1H), 4.49 (s, 1H), 3.75 (s, 1H), 3.64 (s, 2H), 3.57 (s, 2H), 2.84 (d, J=11.1 Hz, 2H), 2.67 (m, 2H), 2.34 (t, J=8.7 Hz, 2H), 2.15 (m, 2H), 1.93 (br s, 2H), 1.62 (m, 4H); LCMS (m/z): 510 (MH⁺).

Compound 84: N-(1-Benzylpiperidin-4-yl)-3-chloro-4-[1-(3,4-dichlorobenzyl)piperidin-4-yloxy]benzamide. ¹H NMR (DMSO-d₆, 300 MHz): δ 8.16 (d, J=7.8 Hz, 1H), 7.90 (s, 1H), 7.75 (d, J=8.4 Hz, 1H), 7.54 (m, 3H), 7.28 (m, 5H), 4.62 (s, 1H), 3.71 (s, 1H), 3.49 (s, 2H), 3.44 (s, 2H), 2.81 (d, J=10.8 Hz, 2H), 2.61 (m, 2H), 2.31 (t, J=8.7 Hz, 2H), 1.99 (m, 4H), 1.71 (m, 4H), 1.38 (m, 3H); LCMS (m/z): 586 (MH⁺).

Compound 85: N-[1-(2-Pyridinylmethyl)piperidin-4-yl]-4-[1-(4-cyanobenzyl)piperidin-4-yloxy]benzamide (as the trifluoroacetate salt). ¹H NMR (DMSO-d₆, 300 MHz): δ 8.67 (d, J=5.7 Hz, 1H), 8.29 (d, J=6.0 Hz, 1H), 7.95 (m, 2H), 7.82 (s, 2H), 7.71 (d, J=6.3 Hz, 2H), 7.51 (m, 2H), 7.02 (s, 2H), 4.49 (s, 1H), 4.02 (m, 5H), 3.45 (d, J=12.3 Hz, 2H), 3.20 (m, 4H), 2.25 (s, 2H), 2.00 (m, 4H), 1.88 (m, 2H); LCMS (m/z): 510 (MH⁺).

Compound 86: N-(1-benzylpiperidin-4-yl)-3-(1-(pyridin-2-yl)piperidin-4-yloxy)benzamide. ¹H NMR (CDCl₃, 300 MHz): δ 8.74 (s, 1H), 8.18 (d, 1H), 8.04 (s, 1H), 7.81 (d, 1H), 7.24-7.58 (m, 6H), 7.00 (m, 2H), 6.81 (m, 2H), 4.80 (m, 1H), 4.22 (m, 1H), 4.18 (s, 2H), 3.94 (m, 4H), 3.52 (m, 2H), 2.90 (m, 2H), 2.44 (m, 2H), 2.01-2.21 (m, 6H); LCMS (m/z): 471 (MH⁺).

Compound 87: N-(1-(pyridin-4-ylmethyl)piperidin-4-yl)-3-(1-(4-(trifluoromethyl)phenyl)piperidin-4-yloxy)benzamide. ¹H NMR (CDCl₃, 300 MHz): δ 8.70 (d, 2H), δ 7.65 (d, 2H), δ 7.45 (d, 2H), δ 7.25-7.39 (m, 2H), δ 7.01 (d, 1H), δ 6.92 (d, 2H), δ 6.80 (d, 1H), δ 4.60 (m, 1H), δ 4.25 (m, 1H), δ 4.09 (s, 2H), δ 3.48 (m, 2H), δ 3.44 (m, 2H), δ 3.22 (m, 2H), δ 2.86 (m, 2H), 62.40 (m, 2H), δ 2.20 (m, 2H), δ 2.10 (m, 2H), δ 1.95 (m, 2H); LCMS (m/z): 539 (MH⁺).

Compound 88: N-(1-(pyridin-4-ylmethyl)piperidin-4-yl)-3-(1-(4-cyanophenyl)piperidin-4-yloxy)benzamide. ¹H NMR (CDCl₃, 300 MHz): δ 8.64 (d, 2H), 7.25-7.52 (m, 7H), 7.03 (d, 1H), 6.85 (d, 2H), 6.87 (d, 1H), 4.60 (m, 1H), 4.15 (m, 1H), 3.89 (s, 2H), 3.61 (m, 2H), 3.30 (m, 4H), 2.62 (m, 2H), 2.02-2.13 (m, 8H); LCMS (m/z): 496 (MH⁺).

Compound 89: N-(1-benzylpiperidin-4-yl)-3-(1-(3-cyanobenzyl)piperidin-4-yloxy)benzamide. ¹H NMR (CDCl₃, 300 MHz): δ 7.65 (s, 1H), 7.24-7.55 (m, 11H), 7.02 (d, 1H), 7.02 (d, 1H), 6.18 (d, 1H), 4.40 (m, 1H), 4.05 (m, 1H), 3.64 (s, 2H), 3.54 (s, 2H), 2.97 (m, 2H), 2.70 (m, 2H), 2.31 (m, 4H), 1.77-2.05 (m, 8H); LCMS (m/z): 510 (MH$^+$).

Example 3

Screening of Compounds Using a Competitive Binding Assay

Candidate compounds are assayed for binding to a membrane-bound adiponectin receptor by performing a competitive binding assay with adiponectin. HEK 293 cellular membrane is coated onto a COSTAR 384 plate, which is then blocked with 1% casein. Polyhistidine-tagged globular adiponectin and a candidate compound is incubated with the membrane in HEPES buffer. Unbound ligands were washed away and the degree of binding of the adiponectin was determined using horseradish peroxidase-conjugated anti-polyhistidine. Compounds that compete with adiponectin binding to the membrane (i.e., give a reduced signal compared to a control performed without a candidate compound) are chosen as hits and are further screened using the below-described functional assays to identify adiponectin receptor agonists.

Example 4

Increase in AMPK Activity and Rate of Fatty Acid Oxidation

Figure 2:
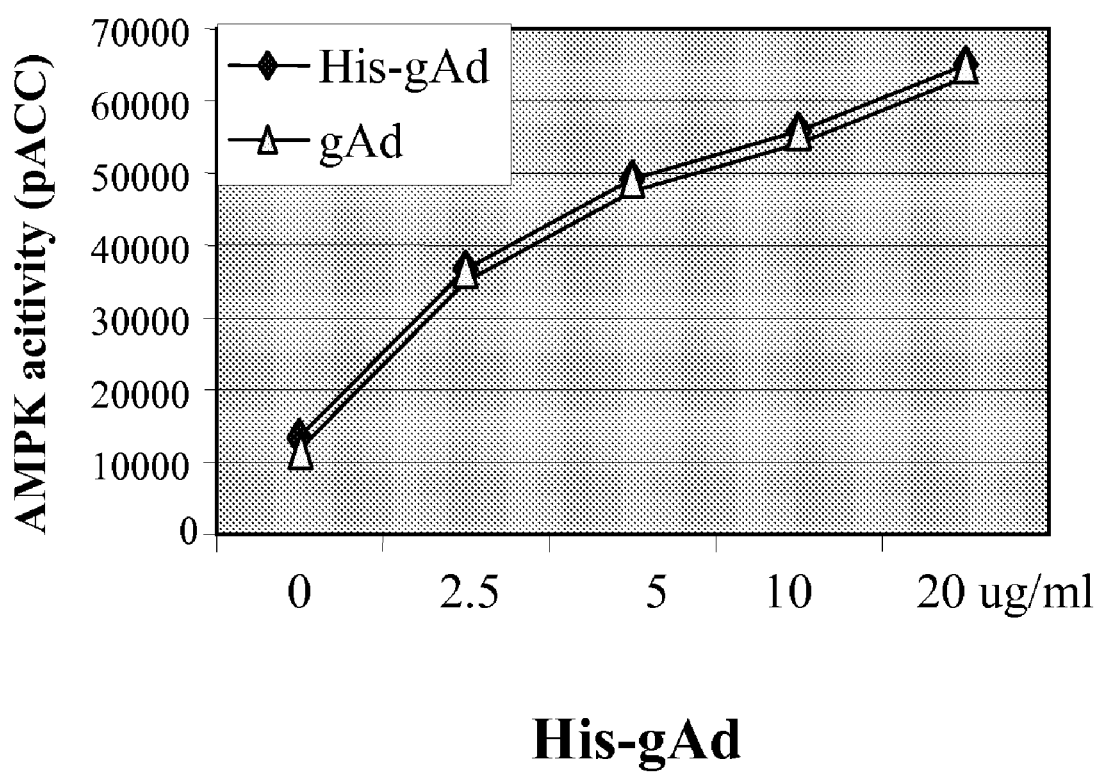
FIG. 2 is a plot of AMPK activity vs. concentration for both gAd and its polyhistidine-tagged analog.

An in-cell western assay was performed to demonstrate the activation of AMPK in human liver cells by globular adiponectin using glutathione S-transferase (GST). AMPK activity was measured by the relative concentration of phosphorylated acetyl Co-A carboxylase, which is one of the products of AMPK. As described above, an increase in pACC correlates with an increase in the rate of fatty acid oxidation. FIG. 1 is a plot of AMPK activity vs. concentration for glutathione S-transferase (GST) and its fusion protein with globular adiponectin (gAd). The presence of gAd clearly increases AMPK. FIG. 2 is a plot of AMPK activity vs. concentration for both gAd and its polyhistidine-tagged analog. The presence of the polyhistidine tag caused little difference in AMPK activity.

Compounds of Tables 1, 2 and 3 were assayed for their ability to activate AMPK using an enzyme-linked immunosorbent assay. The EC$_{50}$ values for AMPK activation for compounds 1-16 are presented in Table 4 below, in which "A" is less than 1 μM; "B" is 1-10 μM; "C" is 10-20 μM; "D" is 20-50 μM; "E" is 50-100 μM, and "F" is >100 μM:

TABLE 4

| Cpd No. | AMPK EC$_{50}$ (μM) |
|---|---|
| 1 | A |
| 2 | A |
| 3 | B |
| 4 | F |
| 5 | E |
| 6 | A |
| 7 | A |
| 8 | B |
| 9 | D |
| 10 | B |
| 11 | B |
| 12 | B |
| 13 | D |
| 14 | A |
| 15 | A |
| 16 | A |

TABLE 4-continued

| Cpd No. | AMPK EC$_{50}$ (μM) |
|---|---|
| 17 | A |
| 18 | A |
| 19 | A |
| 20 | A |
| 21 | B |
| 22 | B |
| 23 | A |
| 24 | C |
| 25 | F |
| 26 | A |
| 27 | A |
| 28 | A |
| 29 | A |
| 30 | A |
| 31 | A |
| 32 | A |
| 33 | A |
| 34 | A |
| 35 | B |
| 36 | A |
| 37 | A |
| 38 | B |
| 39 | B |
| 40 | A |
| 41 | A |
| 42 | A |
| 43 | A |
| 44 | A |
| 45 | A |
| 46 | A |
| 47 | A |
| 48 | A |
| 49 | A |
| 50 | B |
| 51 | A |
| 52 | B |
| 53 | C |
| 54 | A |
| 55 | A |
| 56 | A |
| 57 | A |
| 58 | B |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | F |
| 80 | A |
| 81 | A |
| 82 | A |
| 83 | A |
| 84 | A |
| 85 | A |
| 86 | A |
| 87 | A |
| 88 | B |
| 89 | B |
| 90 | B |
| 91 | A |
| 92 | B |
| 93 | F |
| 94 | A |

TABLE 4-continued

| Cpd No. | AMPK EC$_{50}$ (μM) |
|---|---|
| 95 | A |
| 96 | B |
| 97 | B |
| 98 | B |
| 99 | B |
| 100 | B |
| 101 | C |
| 102 | C |
| 103 | D |
| 104 | C |
| 105 | C |

Figure 3:
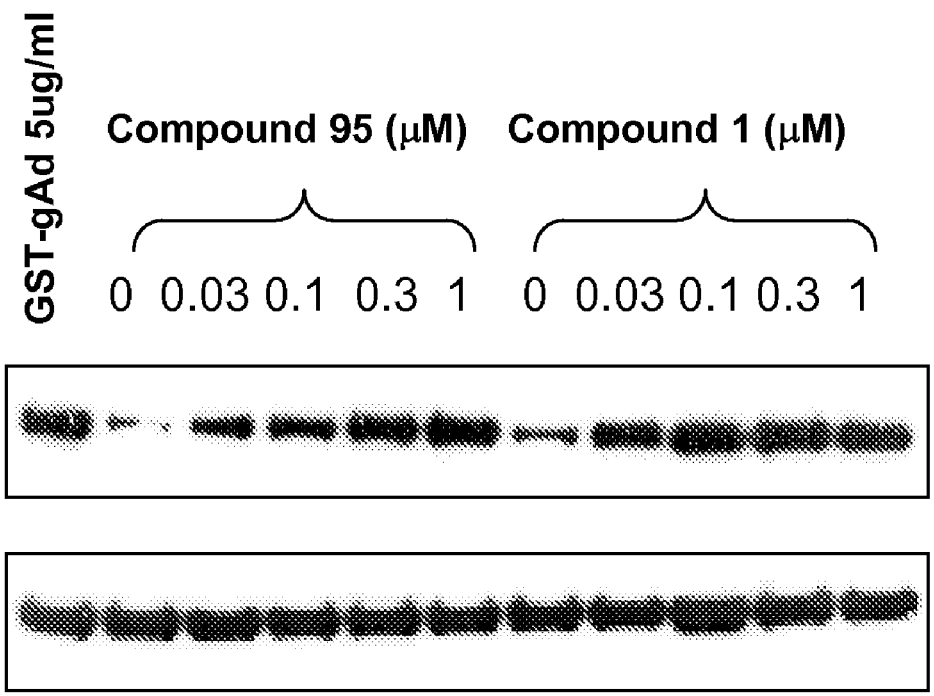
FIG. 3 is a diagram of data for compounds 1-4 in a western blot assay for AMPK activity.
Figure 3:
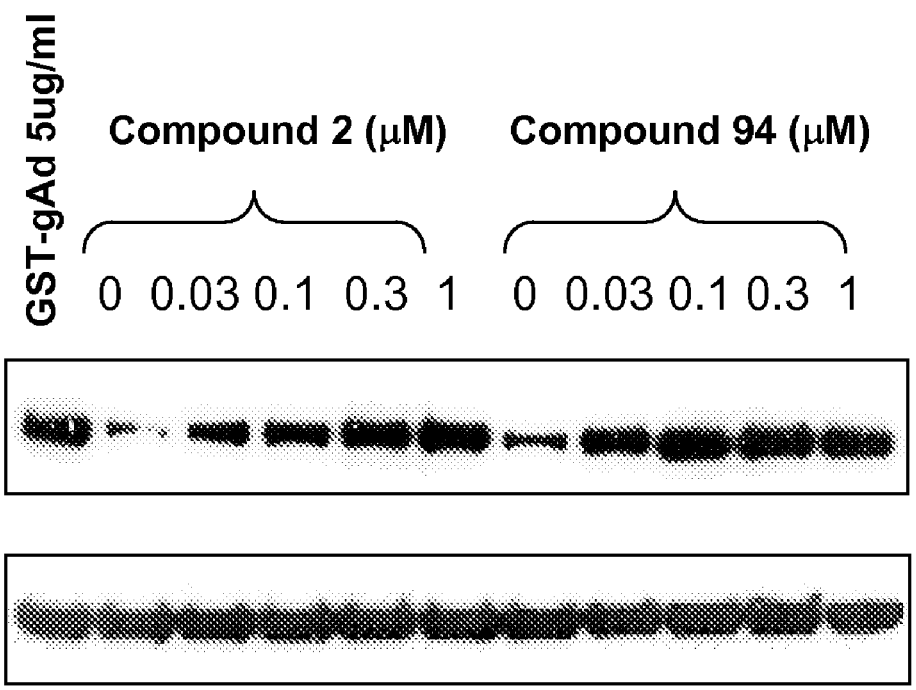

Western blot assays for AMPK activity were performed on compounds 1, 2, 94 and 95. FIG. 3 presents gel electrophoresis data for compounds 1, 2, 94 and 95 relative to GST-gAd. Each of these compounds demonstrated strong activity in the western blot assay.

Example 5

Decrease in Glycogen Concentration

Figure 4:
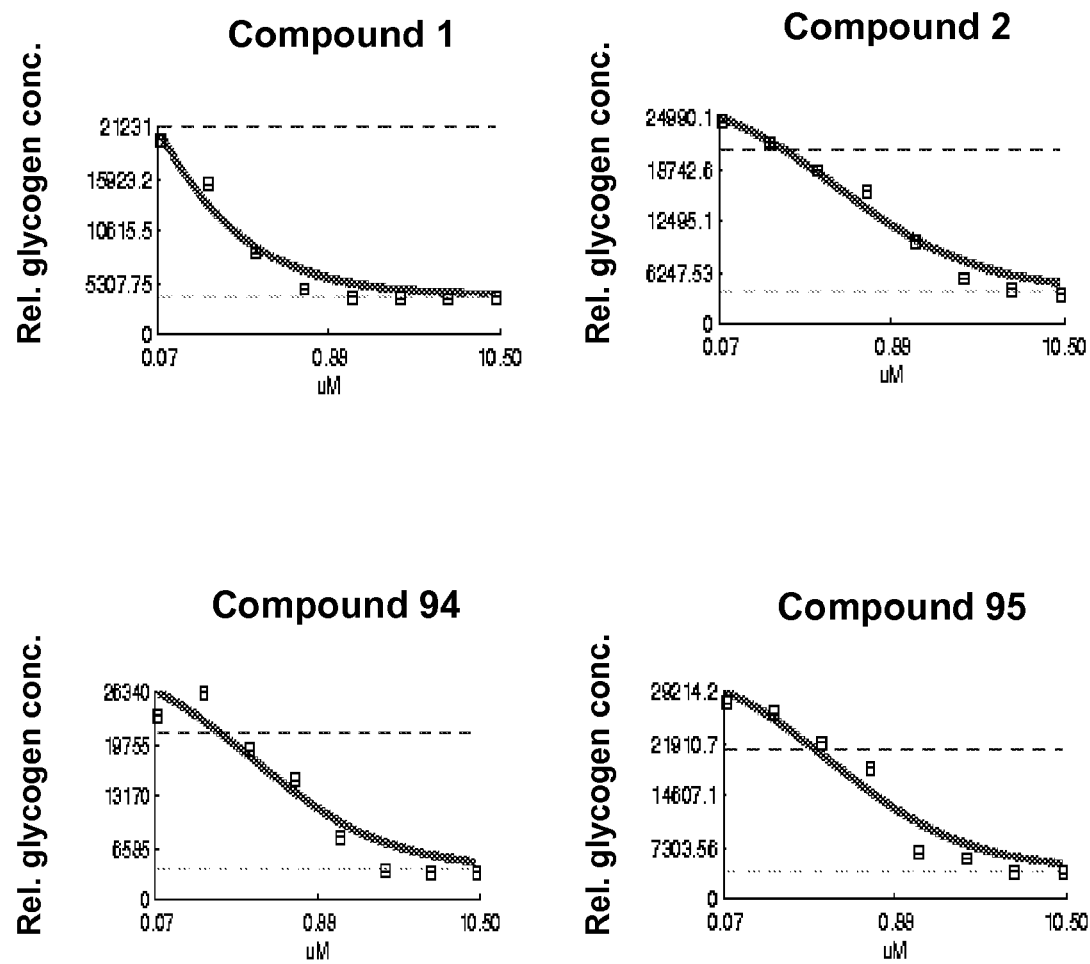
FIG. 4 is a set of plots showing reduction of glycogen content in HepG2 cells by compounds 1-4.

The ability of compounds of the present invention to reduce the glycogen content in liver cells was determined using a functional assay. Human liver cells (HepG2) were seeded in a 96 well plate and on the next day were treated with compounds 1, 2, 94 and 95 for 16 hours. The glycogen content of the cells was determined using Amplex Red. Data for compounds 1, 2, 94 and 95 are presented in FIG. 4. Each of these compounds demonstrated a sub-micromolar IC$_{50}$ value.

Example 6

Increase in Glucose Uptake

Figure 5:
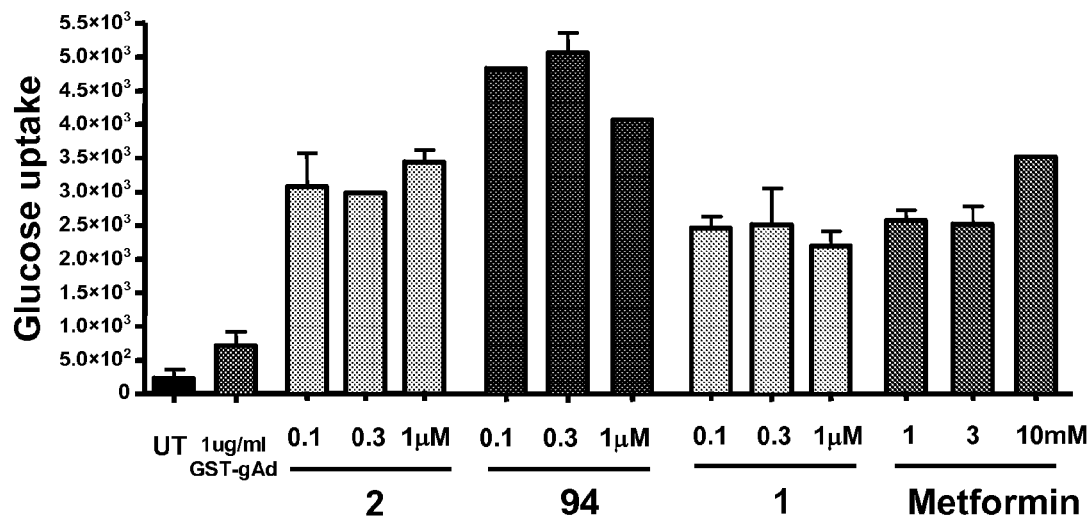
FIG. 5 is a bar graph showing glucose uptake data for compounds 1-4 relative to adiponectin.
Figure 5:
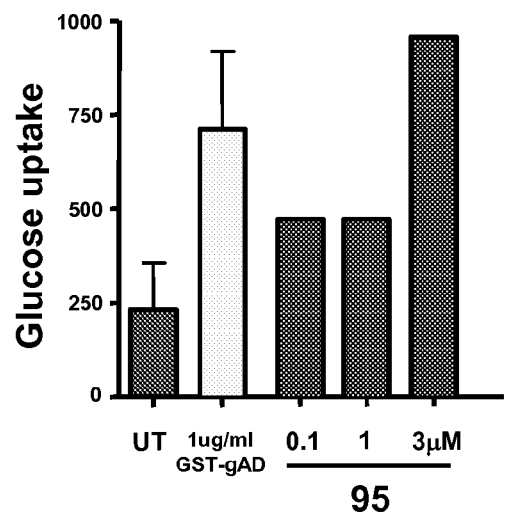

The ability of compounds of the present invention to increase glucose uptake in skeletal muscle cells was determined by a functional assay. Rat differentiated L6 myotube cells were incubated for two hours with GST-gAd and compounds 1, 2, 94 and 95, then with 2-deoxy-D-[6-$^3$H]glucose for 10 minutes. Uptake of 2-deoxy-D-[6-$^3$H]glucose was determined by liquid scintillation counting. FIG. 5 presents data for compounds 1, 2, 94 and 95, shown relative to adiponectin.

What is claimed is:
1. A compound having structural formula (I)

(I)

or a pharmaceutically acceptable salt, or N-oxide thereof, wherein
$R^1$ is H;
$R^2$ is azetidinyl, pyrrolidinyl, piperidinyl, or azepanyl, each substituted at its 1-position with an optionally substituted pyridinylmethyl, an optionally substituted furanylmethyl, an optionally substituted thienylmethyl, CO—O—(C$_0$-C$_6$ alkyl), —CO-Het, —CO—Ar or —SO$_2$—(C$_0$-C$_6$ alkyl), wherein the azetidinyl, pyrrolidinyl, piperidinyl or azepanyl groups are optionally further substituted
each $R^3$ is independently selected from —(C$_1$-C$_6$ alkyl), —(C$_1$-C$_6$ fluoroalkyl), —(C$_0$-C$_6$ alkyl)-Ar; —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$, -halogen, —NO$_2$ and —CN;
w is 0, 1, 2 or 3;
n is 0, 1, 2 or 3;
each $R^4$ is independently selected from —(C$_1$-C$_6$ alkyl), —(C$_1$-C$_6$ fluoroalkyl), —(C$_0$-C$_6$ alkyl)-Ar; —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$, -halogen, —NO$_2$ and —CN, and two $R^4$ on the same carbon optionally combine to form oxo;
x is 0, 1, 2, 3 or 4;
T is —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$; or in which
Q is —(C$_0$-C$_3$ alkyl)- in which each carbon of the (C$_0$-C$_3$ alkyl) is optionally and independently substituted with one or two R$^{16}$;
each $R^{16}$ is independently selected from —(C$_1$-C$_6$ alkyl), —(C$_1$-C$_6$ fluoroalkyl), —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$, -halogen, —NO$_2$ and —CN, and two $R^{16}$ on the same carbon optionally combine to form oxo;
the ring system denoted by "A" is a monocyclic aryl or heteroaryl;
each $R^5$ is independently selected from —(C$_1$-C$_6$ alkyl), —(C$_1$-C$_6$ fluoroalkyl), —(C$_0$-C$_6$ alkyl)-Ar; —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$, -halogen, —NO$_2$ and —CN; and
y is 0, 1, 2, 3 or 4;
in which
each L is independently selected from —NR$^9$C(O)O—, —NR$^9$C(O)—NR$^9$—, —NR$^9$C(O)S—, —NR$^9$C(O)—, —NR$^9$C(S)O—, —NR$^9$C(S)—NR$^9$—, —NR$^9$C(S)S—, —NR$^9$C(S)—, —OC(O)NR$^9$—, —SC(O)NR$^9$—, —C(S)NR$^9$—, —OC(S)NR$^9$—, —SC(S)NR$^9$—, —C(S)NR$^9$—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR$^9$C(NR$^2$)NR$^9$—, —NR$^9$SO$_2$—, —SO$_2$NR$^9$— and —NR$^9$SO$_2$NR$^9$—,
each $R^6$, $R^7$, $R^8$ and $R^{10}$ is independently selected from H, —(C$_1$-C$_6$ alkyl), —(C$_1$-C$_6$ fluoroalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl) and —(C$_0$-C$_6$ alkyl)-S(O)$_{0-2}$—(C$_0$-C$_6$ alkyl), each R$^9$ is independently selected from —H, —(C$_1$-C$_4$ alkyl) and —C(O)—(C$_1$-C$_4$ alkyl), each Ar is an optionally substituted aryl, each Het is an optionally substituted heteroaryl, each Cak is an optionally substituted cycloalkyl, each Hca is an optionally substituted heterocycloalkyl, and each alkyl is optionally substituted.

2. A compound according to claim 1, wherein

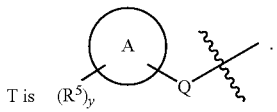

3. A compound according to claim 2, wherein Q is an unsubstituted (C$_1$-C$_3$ alkyl).

4. A compound according to claim 2, wherein Q is a (C$_1$-C$_3$ alkyl) having as its only substitution a single oxo group.

5. A compound according to claim 2, wherein Q is —CH$_2$—.

6. A compound according to claim 2, wherein Q is a single bond.

7. A compound according to claim 2, wherein Q is —CO— or —CH(CH$_3$)—.

8. A compound according to claim 2, wherein y is 0, 1, 2 or 3.

9. A compound according to claim 2, wherein y is 0.

10. A compound according to claim 2, wherein y is 1.

11. A compound according to claim 2, wherein y is 1 to 4 and at least one R$^5$ is halo, cyano, trifluoromethyl or trifluoromethoxy.

12. A compound according to claim 2, wherein the ring system denoted by "A" is a phenyl.

13. A compound according to claim 12, wherein y is 1 and R$^5$ is attached to the phenyl para to Q.

14. A compound according to claim 12 wherein y is 1 and R$^5$ is selected from the group consisting of halo, cyano, —(C$_1$-C$_4$ fluoroalkyl), —O—(C$_1$-C$_4$ fluoroalkyl), acyl, carboxylate, carboxamide and nitro.

15. A compound according to claim 14, wherein R$^5$ is selected from the group consisting of —Cl, —F, cyano, trifluoromethyl and trifluoromethoxy.

16. A compound according to claim 12, wherein the

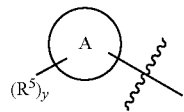

moiety is a 3,4-dihalophenyl.

17. A compound according to claim 2, wherein the ring system denoted by "A" is a monocyclic heteroaryl.

18. A compound according to claim 2, wherein the ring system denoted by "A" is a pyridyl, a thienyl, or a furanyl.

19. A compound according to claim 1, wherein the compound has the structural formula (II)

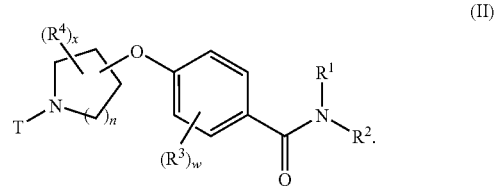

20. A compound according to claim 1, wherein the compound has the structural formula (III)

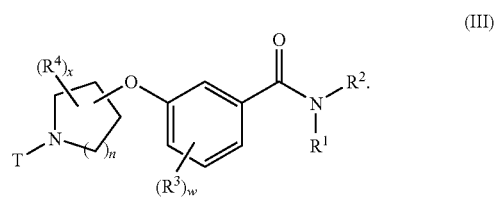

21. A compound according to claim 1, wherein the compound has the structural formula (IV)

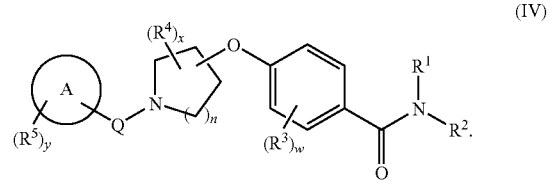

22. A compound according to claim 1, wherein the compound has the structural formula (V)

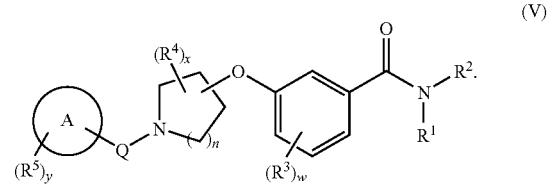

23. A compound according to claim 1, wherein n is 1 or 2.

24. A compound according to claim 1, wherein n is 2.

25. A compound according to claim 24, wherein the compound has the structural formula (VI)

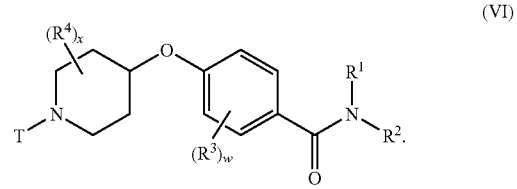

26. A compound according to claim 24, wherein the compound has the structural formula (VII)

(VII)

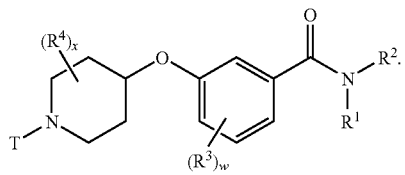

27. A compound according to claim 24, wherein the compound has the structural formula (VIII)

(VIII)

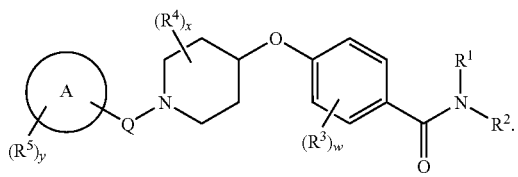

28. A compound according to claim 24, wherein the compound has the structural formula (IX)

(IX)

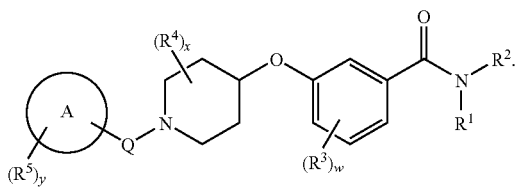

29. A compound according to claim 1, wherein $R^1$ is —H and $R^2$ is azetidinyl-3-yl, piperidinyl-4-yl, pyrrolidin-3-yl, or azepan-4-yl.

30. A compound according to claim 29, wherein $R^2$ is piperidin-4-yl.

31. A compound according to claim 29, wherein $R^2$ is pyrrolidin-3-yl.

32. A compound according to claim 1, wherein $R^2$ is substituted at its 1-position with an optionally-substituted pyridinylmethyl, an optionally-substituted furanylmethyl or an optionally-substituted thienylmethyl.

33. A compound according to claim 1, wherein $R^2$ is substituted at its 1-position with an unsubstituted pyridinylmethyl, an unsubstituted furanylmethyl or an unsubstituted thienylmethyl.

34. A compound according to claim 1, wherein $R^2$ is substituted at its 1-position with —CO—O—($C_0$-$C_6$ alkyl), —CO-Het, —CO—Ar or —SO$_2$—($C_0$-$C_6$ alkyl).

35. A compound according to claim 1, wherein w is 0, 1 or 2.

36. A compound according to claim 1, wherein w is 0.

37. A compound according to claim 1, wherein w is at least 1 and at least one $R^3$ is selected from the group consisting of halo, cyano, —($C_1$-$C_4$ fluoroalkyl), —O—($C_1$-$C_4$ fluoroalkyl), acyl, carboxylate, carboxamide and nitro.

38. A compound according to claim 1, wherein w is 1 and $R^3$ is selected from the group consisting of halo, cyano, —($C_1$-$C_4$ fluoroalkyl), —O—($C_1$-$C_4$ fluoroalkyl), acyl, carboxylate, carboxamide and nitro.

39. A compound according to claim 38, wherein $R^3$ is —Cl or —F.

40. A compound according to claim 38, wherein the compound has structural formula (X)

(X)

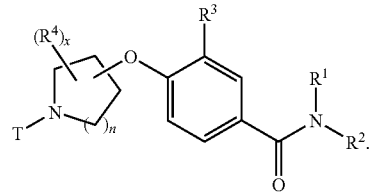

41. A compound according to claim 38, wherein the compound has structural formula (XI)

(XI)

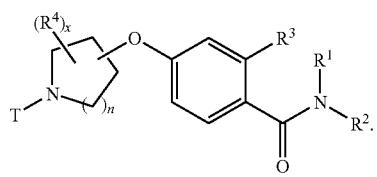

42. A compound according to claim 1, wherein x is 0, 1, 2 or 3.

43. A compound according to claim 1, wherein x is 0.

44. A compound according to claim 1, wherein x is 1 or 2.

45. A compound according to claim 1, having structural formula (XII)

(XII)

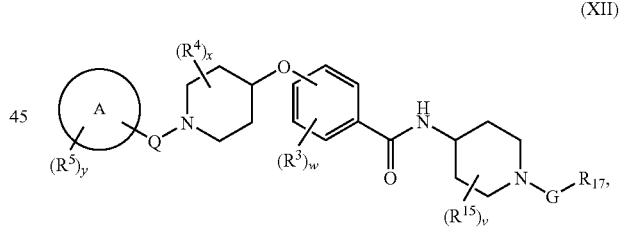

in which

Q is a bond, —CH$_2$—, —C(H)($R^{16}$)— or —C($R^{16}$)$_2$—;

G is —CH$_2$—, —C(H)($R^{16}$)— or —C($R^{16}$)$_2$—;

v is 0, 1, 2, 3 or 4;

each $R^{15}$ is independently selected from —($C_1$-$C_6$ alkyl), —($C_1$-$C_6$ fluoroalkyl), —($C_0$-$C_6$ alkyl)-Ar; —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-N$R^8R^9$, —($C_0$-$C_6$ alkyl)-O$R^{10}$, —($C_0$-$C_6$ alkyl)-S(O)$_{0-2}R^{10}$, -halogen, —NO$_2$ and —CN, and two $R^{15}$ on the same carbon optionally combine to form oxo; and $R^{17}$ is an optionally-substituted pyridinyl, an optionally-substituted furanyl, or an optionally-substituted thienyl.

46. A compound according to claim 1, having structural formula (XV)

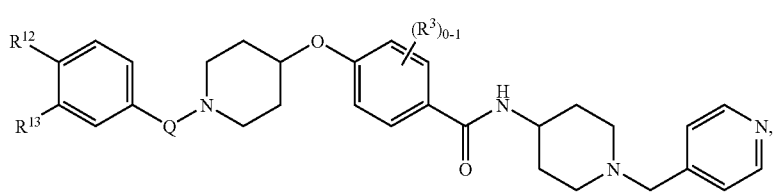

in which
Q is —CH$_2$— or a single bond;
R$^3$ is H or halo; and
R$^{12}$ and R$^{13}$ are independently H, trifluoromethyl, trifluoromethoxy, halo or cyano.

47. A compound according to claim 1, having structural formula (XVI)

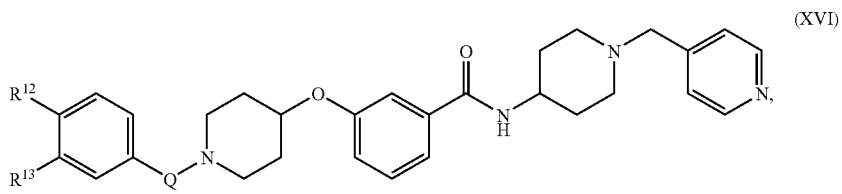

in which
Q is —CH$_2$— or a single bond; and
R$^{12}$ and R$^{13}$ are independently H, trifluoromethyl, trifluoromethoxy, halo or cyano.

48. A compound according to claim 1, wherein the compound is selected from the group consisting of:
tert-butyl 4-(3-fluoro-4-(1-(4-(trifluoromethyl)phenyl)piperidin-4-yloxy)benzamido)piperidine-1-carboxylate;
3-fluoro-N-(1-(pyridin-4-ylmethyl)piperidin-4-yl)-4-(1-(4-(trifluoromethyl)phenyl)piperidin-4-yloxy)benzamide;
3-fluoro-N-(1-(pyridin-3-ylmethyl)piperidin-4-yl)-4-(1-(4-(trifluoromethyl)phenyl)piperidin-4-yloxy)benzamide;
3-fluoro-N-(1-(pyridin-2-ylmethyl)piperidin-4-yl)-4-(1-(4-(trifluoromethyl)phenyl)piperidin-4-yloxy)benzamide;
3-fluoro-N-(1-(isopropylsulfonyl)piperidin-4-yl)-4-(1-(4-(trifluoromethyl)phenyl)piperidin-4-yloxy)benzamide;
3-fluoro-N-(1-isonicotinoylpiperidin-4-yl)-4-(1-(4-(trifluoromethyl)phenyl)piperidin-4-yloxy)benzamide;
4-(1-(4-cyanophenyl)piperidin-4-yloxy)-3-fluoro-N-(1-(pyridin-4-ylmethyl)piperidin-4-yl)benzamide;
tert-butyl 4-(4-(1-(4-cyanobenzyl)piperidin-4-yloxy)benzamido)piperidine-1-carboxylate;
4-(1-(4-cyanobenzyl)piperidin-4-yloxy)-N-(1-(pyridin-4-ylmethyl)piperidin-4-yl)benzamide;
4-(1-(4-cyanobenzyl)piperidin-4-yloxy)-N-(1-(pyridin-2-ylmethyl)piperidin-4-yl)benzamide;
N-(1-(pyridin-4-ylmethyl)piperidin-4-yl)-3-(1-(4-(trifluoromethyl)phenyl)piperidin-4-yloxy)benzamide;
N-(1-(pyridin-4-ylmethyl)piperidin-4-yl)-3-(1-(4-cyanophenyl)piperidin-4-yloxy)benzamide.

49. A pharmaceutical composition comprising:
at least one pharmaceutically acceptable carrier, diluent or excipient; and
a compound according to claim 1
or a pharmaceutically acceptable salt or N-oxide thereof.

50. A compound having structural formula (I)

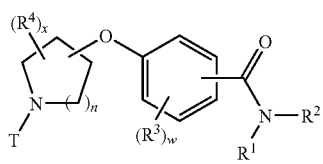

or a pharmaceutically acceptable salt, or N-oxide thereof, wherein
R$^1$ is H;
R$^2$ is -Hca;
each R$^3$ is independently selected from —(C$_1$-C$_6$ alkyl), —(C$_1$-C$_6$ fluoroalkyl), —(C$_0$-C$_6$ alkyl)-Ar; —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$, -halogen, —NO$_2$ and —CN;
w is 0, 1, 2 or 3;
n is 0, 1, 2 or 3;
each R$^4$ is independently selected from —(C$_1$-C$_6$ alkyl), —(C$_1$-C$_6$ fluoroalkyl), —(C$_0$-C$_6$ alkyl)-Ar; —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$, -halogen, —NO$_2$ and —CN, and two R$^4$ on the same carbon optionally combine to form oxo;

x is 0, 1, 2, 3 or 4;
T is

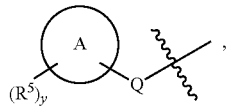

in which
Q is —($C_1$-$C_3$ alkyl)- substituted with a single oxo group;
the ring system denoted by "A" is a monocyclic aryl or heteroaryl;
each $R^5$ is independently selected from —($C_1$-$C_6$ alkyl), —($C_1$-$C_6$ fluoroalkyl), —($C_0$-$C_6$ alkyl)-Ar; —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-S(O)$_{0-2}R^{10}$, -halogen, —$NO_2$ and —CN; and
y is 0, 1, 2, 3 or 4;
in which
each L is independently selected from —$NR^9C(O)O$—, —$NR^9C(O)$—$NR^9$—, —$NR^9C(O)S$—, —$NR^9C(O)$—, —$NR^9C(S)O$—, —$NR^9C(S)$—$NR^9$—, —$NR^9C(S)S$—, —$NR^9C(S)$—, —OC(O)$NR^9$—, —SC(O)$NR^9$—, —C(S)$NR^9$—, —OC(S)$NR^9$—, —SC(S)$NR^9$—, —C(S)$NR^9$—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —$NR^9C(NR^2)NR^9$—, —$NR^9SO_2$—, —$SO_2NR^9$— and —$NR^9SO_2NR^9$—,
each $R^6$, $R^7$, $R^8$ and $R^{10}$ is independently selected from H, —($C_1$-$C_6$ alkyl), —($C_1$-$C_6$ fluoroalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl) and —($C_0$-$C_6$ alkyl)-S(O)$_{0-2}$—($C_0$-$C_6$ alkyl),
each $R^9$ is independently selected from —H, —($C_1$-$C_4$ alkyl) and —C(O)—($C_1$-$C_4$ alkyl),
each Ar is an optionally substituted aryl,
each Het is an optionally substituted heteroaryl,
each Cak is an optionally substituted cycloalkyl,
each Hca is an optionally substituted heterocycloalkyl, and
each alkyl is optionally substituted.

51. A compound according to claim 50, wherein Q is —CO—.

52. A compound according to claim 50, wherein the ring system denoted by "A" is a phenyl.

53. A compound according to claim 50, wherein y is 1 to 4 and at least one $R^5$ is halo, cyano, trifluoromethyl or trifluoromethoxy.

54. A compound according to claim 50 wherein y is 1 and $R^5$ is selected from the group consisting of halo, cyano, —($C_1$-$C_4$ fluoroalkyl), —O—($C_1$-$C_4$ fluoroalkyl), acyl, carboxylate, carboxamide and nitro.

55. A compound according to claim 50, wherein the

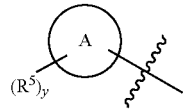

moiety is a 3,4-dihalophenyl.

56. A compound according to claim 50, wherein n is 1 or 2.

57. A compound according to claim 50, wherein $R^1$ is —H and $R^2$ is -(optionally-substituted azetidinyl), -(optionally-substituted pyrrolidinyl), -(optionally-substituted piperidinyl), or -(optionally-substituted azepanyl).

58. A compound according to claim 57 wherein $R^2$ is substituted at its 1-position with ($C_0$-$C_3$ alkyl)-Ar or ($C_0$-$C_3$ alkyl)-Het.

59. A compound according to claim 50, wherein the compound is selected from
N-(1-benzylpiperidin-4-yl)-3-chloro-4-(1-(4-(trifluoromethyl)benzoyl)piperidin-4-yloxy)benzamide; and
N-(1-benzylpiperidin-4-yl)-3-chloro-4-(1-(4-fluorobenzoyl)piperidin-4-yloxy)benzamide
or a pharmaceutically acceptable salt or N-oxide thereof.

60. A pharmaceutical composition comprising:
at least one pharmaceutically acceptable carrier, diluent or excipient; and
a compound according to claim 50 or a pharmaceutically acceptable salt or N-oxide thereof.

61. A method for increasing fatty acid oxidation in a cell, the method comprising contacting the cell with an effective amount of a compound described in claim 1, or a pharmaceutically acceptable salt or N-oxide thereof.

62. A method for decreasing glycogen concentration in a cell, the method comprising contacting the cell with an effective amount of a compound described in claim 1, or a pharmaceutically acceptable salt or N-oxide thereof.

63. A method for increasing glucose uptake in a cell, the method comprising contacting the cell with an effective amount of a compound described in claim 1, or a pharmaceutically acceptable salt or N-oxide thereof.

64. A method for reducing triglyceride levels in a subject, the method comprising administering to the subject an effective amount of a compound described in claim 1, or a pharmaceutically acceptable salt or N-oxide thereof.

65. A method for treating type II diabetes in a subject, the method comprising administering to the subject an effective amount of a compound described in claim 1, or a pharmaceutically acceptable salt or N-oxide thereof.

66. A method for treating atherosclerosis in a subject, the method comprising administering to the subject an effective amount of a compound described in claim 1, or a pharmaceutically acceptable salt or N-oxide thereof.

67. A method for activating the AMPK pathway in a cell, the method comprising contacting the cell with an effective amount of a compound described in claim 1, or a pharmaceutically acceptable salt or N-oxide thereof.

68. A method for reducing triglyceride levels in a subject, the method comprising administering to the subject an effective amount of a compound described in claim 50, or a pharmaceutically acceptable salt or N-oxide thereof.

69. A method for treating type II diabetes in a subject, the method comprising administering to the subject an effective amount of a compound described in claim 50, or a pharmaceutically acceptable salt or N-oxide thereof.

70. A method for treating atherosclerosis in a subject, the method comprising administering to the subject an effective amount of a compound described in claim 50, or a pharmaceutically acceptable salt or N-oxide thereof.

* * * * *